(12) United States Patent
Harkins, Jr.

(10) Patent No.: US 11,957,790 B1
(45) Date of Patent: Apr. 16, 2024

(54) COMBINATION LYOPHILIZATION AND DISPENSING SYRINGE ASSEMBLY AND METHODS OF USING SAME

(71) Applicant: Thomas John Harkins, Jr., Whaleville, MD (US)

(72) Inventor: Thomas John Harkins, Jr., Whaleville, MD (US)

(*) Notice: Subject to any disclaimer, the term of this patent is extended or adjusted under 35 U.S.C. 154(b) by 0 days.

(21) Appl. No.: 18/542,834

(22) Filed: Dec. 18, 2023

Related U.S. Application Data

(63) Continuation-in-part of application No. 18/348,675, filed on Jul. 7, 2023, now Pat. No. 11,890,379, which
(Continued)

(51) Int. Cl.
*A61K 9/19* (2006.01)
*F26B 5/06* (2006.01)

(52) U.S. Cl.
CPC . *A61K 9/19* (2013.01); *F26B 5/06* (2013.01)

(58) Field of Classification Search
CPC ..................................... F26B 5/06; A61K 9/19
(Continued)

(56) References Cited

U.S. PATENT DOCUMENTS

| | | |
|---|---|---|
| 3,795,986 A | 3/1974 | Sutherland |
| 3,817,259 A | 6/1974 | Strasser |

(Continued)

FOREIGN PATENT DOCUMENTS

| | | | |
|---|---|---|---|
| EP | 1269096 B1 * | 11/2005 | ................ F26B 5/06 |
| EP | 3 333 523 B1 | 12/2016 | |

(Continued)

OTHER PUBLICATIONS

Butler, CA et al., *Journal of Thermoplastic Composite Materials*, Jul. 1998, vol. 11 (4): 338-363.
(Continued)

*Primary Examiner* — Stephen M Gravini
(74) *Attorney, Agent, or Firm* — Smith Patent, LLC; Chalin A. Smith

(57) ABSTRACT

Herein described is a syringe assembly configured for the in situ lyophilization of an initial liquid preparation into a lyophilized product as well as the subsequent sealing of the lyophilized product for storage and transport, user reconstitution of the lyophilized product, and dispensing of the lyophilized product in rehydrated form to a patient in a medical setting, all in the same syringe. The combination lyophilization and dispensing syringe assemblies of the present invention greatly enhance the efficiency of the lyophilization process and find particular utility in conjunction with the dedicated lyophilization apparatus and methods described in U.S. Pat. Nos. 11,536,512 and 11,723,870. In particularly preferred embodiments, the present invention provides for shortened lyophilization cycles in a syringe barrel optionally fitted with a sealing Luer lock cap at its distal end and a vented stopper at its proximal end. During lyophilization, gas may flow out of the syringe barrel and through the stopper. After lyophilization, the stopper slid to its sealed position, thereby forming an airtight syringe whose contents are insulated from surrounding atmosphere and potential contamination. During the life cycle of the filled syringe, from seal to storage to transport, the lyophilized material is never exposed to the atmosphere. In addition, at time of use, an elongate stem may be threaded into the stopper to form a dispensing plunger in which the stopper acts as a sealing piston element In this manner, the assembly of syringe barrel, stopper and elongated stem constitute a fully functioning syringe that may be used to rehydrate and dispense the medicament of interest.

20 Claims, 73 Drawing Sheets

Related U.S. Application Data is a continuation of application No. 18/066,107, filed on Dec. 14, 2022, now Pat. No. 11,723,870, which is a continuation-in-part of application No. 17/588,349, filed on Jan. 31, 2022, now Pat. No. 11,536,512.

(60) Provisional application No. 63/474,132, filed on Jul. 21, 2022.

(58) Field of Classification Search
 USPC .......................................................... 34/284
 See application file for complete search history.

(56) References Cited

U.S. PATENT DOCUMENTS

| | | | |
|---|---|---|---|
| 4,127,947 | A | 12/1978 | Webb |
| 5,286,448 | A | 2/1994 | Childers |
| 5,522,155 | A | 6/1996 | Jones |
| 5,596,814 | A | 1/1997 | Zingle |
| 5,964,043 | A | 10/1999 | Oughton |
| 6,122,836 | A | 9/2000 | Tenedini |
| 6,199,297 | B1 | 3/2001 | Wisniewski |
| 6,290,680 | B1 | 9/2001 | Forsberg |
| 6,566,144 | B1 * | 5/2003 | Madril ............... F26B 5/06 436/177 |
| 7,086,177 | B2 | 8/2006 | Alstat |
| 9,005,183 | B2 | 4/2015 | Harkins |
| 9,222,728 | B2 | 12/2015 | Py |
| 9,435,586 | B2 | 9/2016 | Ling |
| 9,739,532 | B2 | 8/2017 | Baugh |
| 10,364,053 | B2 | 7/2019 | Wensley |
| 10,443,935 | B2 | 10/2019 | Knight |
| 10,794,632 | B2 * | 10/2020 | McCann ............... A61J 3/02 |
| D908,916 | S * | 1/2021 | Sherman ............... D24/229 |
| 11,536,512 | B1 | 12/2022 | Harkins, Jr. |
| 11,723,870 | B1 * | 8/2023 | Harkins, Jr. ......... F26B 5/06 34/284 |
| 11,890,379 | B2 * | 2/2024 | Harkins, Jr. ......... A61K 9/19 |
| 2001/0037091 | A1 * | 11/2001 | Wironen ............... A61F 2/4644 604/82 |
| 2001/0042317 | A1 * | 11/2001 | Yarborough .......... F26B 5/06 34/284 |
| 2009/0001042 | A1 | 1/2009 | Sever |
| 2014/0183094 | A1 | 7/2014 | Imai |
| 2018/0044076 | A1 | 2/2018 | Eichhorn |
| 2018/0110922 | A1 | 4/2018 | Dunki-Jacobs |
| 2020/0223604 | A1 | 7/2020 | Heinlein |
| 2022/0110829 | A1 | 4/2022 | Zwirnmann |

FOREIGN PATENT DOCUMENTS

| | | | |
|---|---|---|---|
| GB | 1011475 | | 12/1965 |
| JP | 2003528662 A | * | 9/2003 |
| JP | 2012046250 | | 3/2012 |
| JP | 2015186462 A | | 10/2015 |
| WO | WO-9527180 | | 10/1995 |
| WO | WO-9915215 A1 | | 4/1999 |
| WO | WO-0173363 A1 | * | 10/2001 ............... F26B 5/06 |
| WO | WO-2019063772 | | 4/2019 |

OTHER PUBLICATIONS

Coogan, Timothy J. et al., *Journal of Rheology*, Jul. 1, 2019, vol. 63 (4): 655-672.

\* cited by examiner

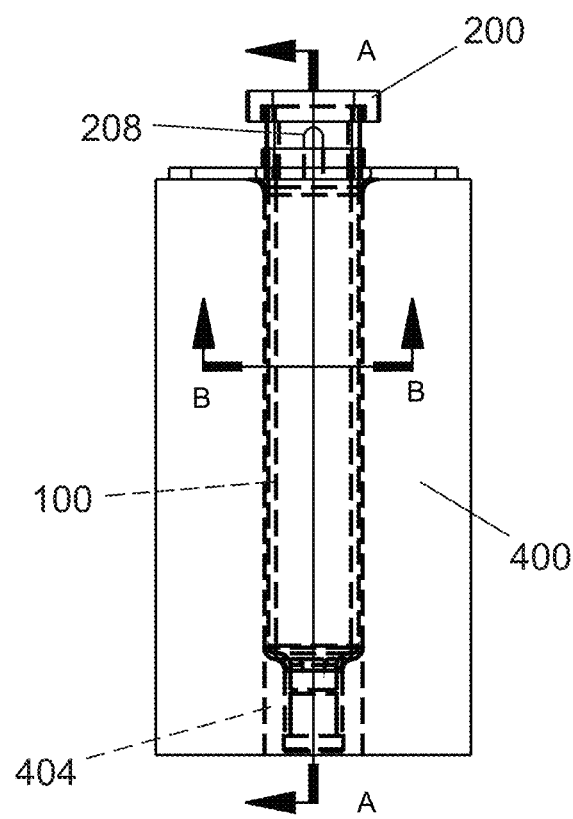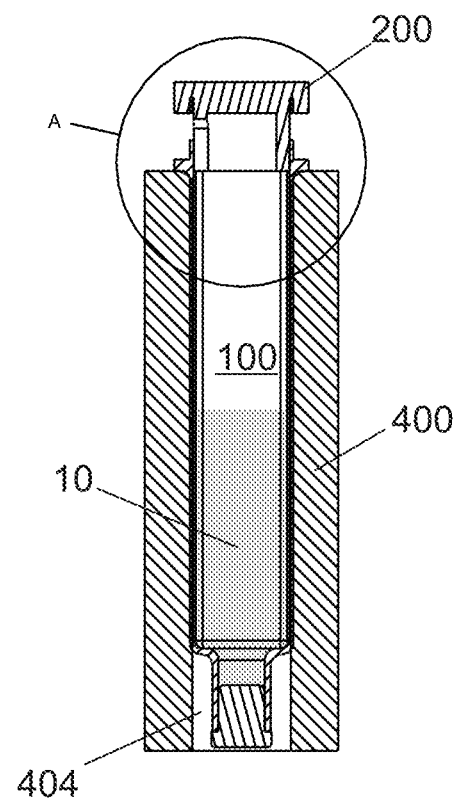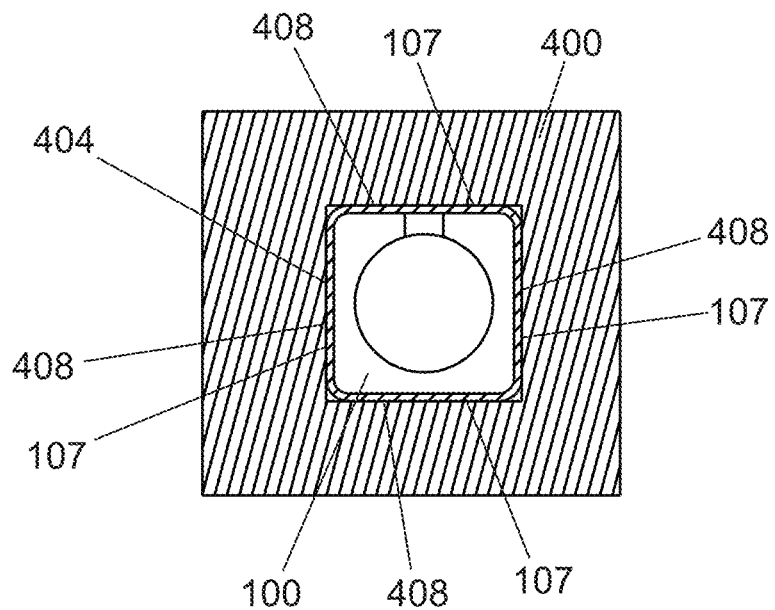
Fig. 38
Fig. 39
Fig. 40

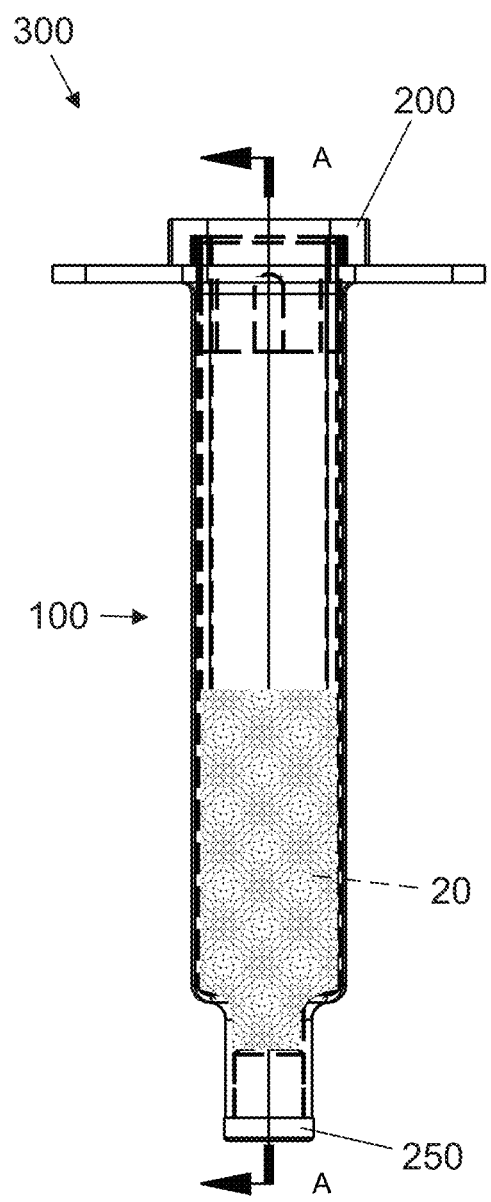
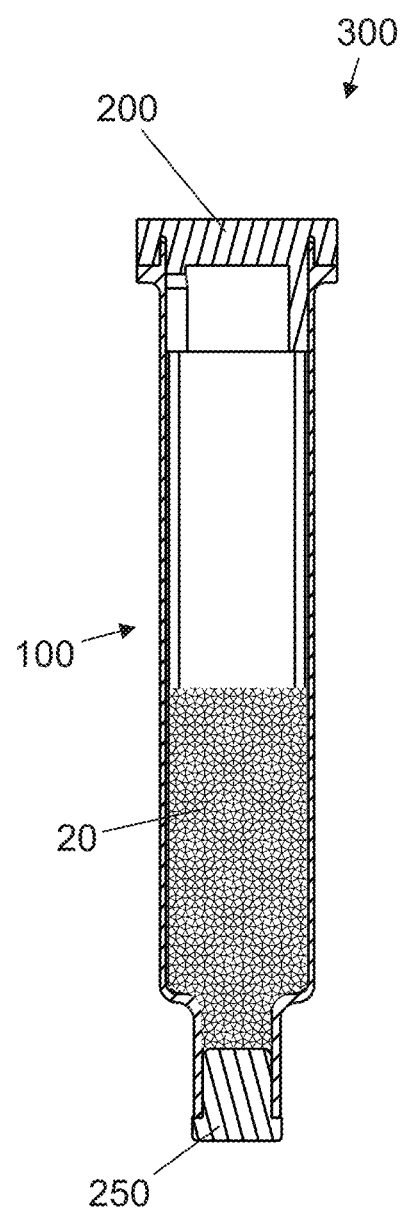
Fig. 59
Fig. 60

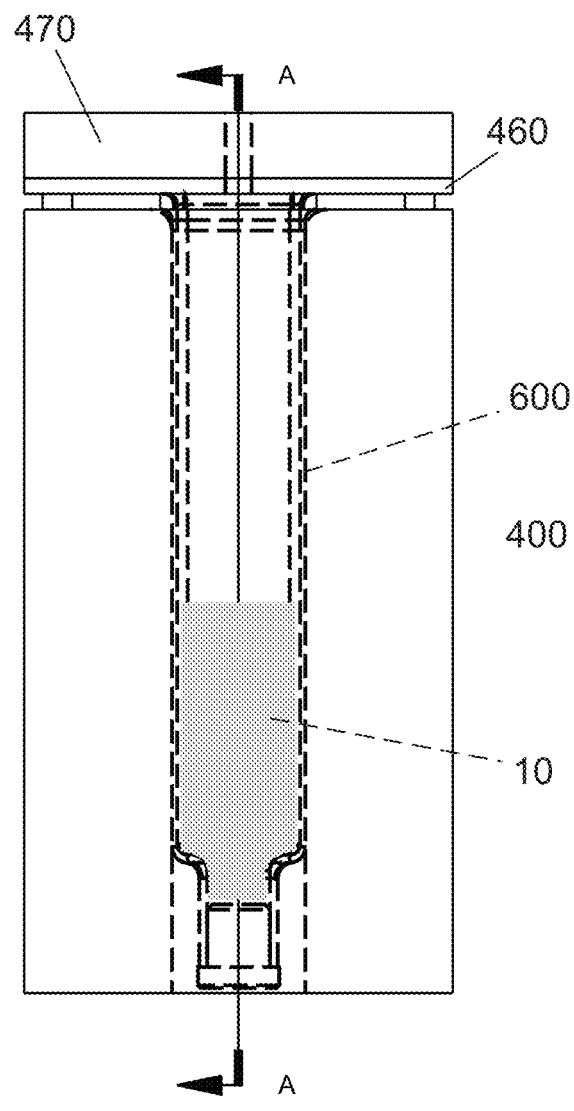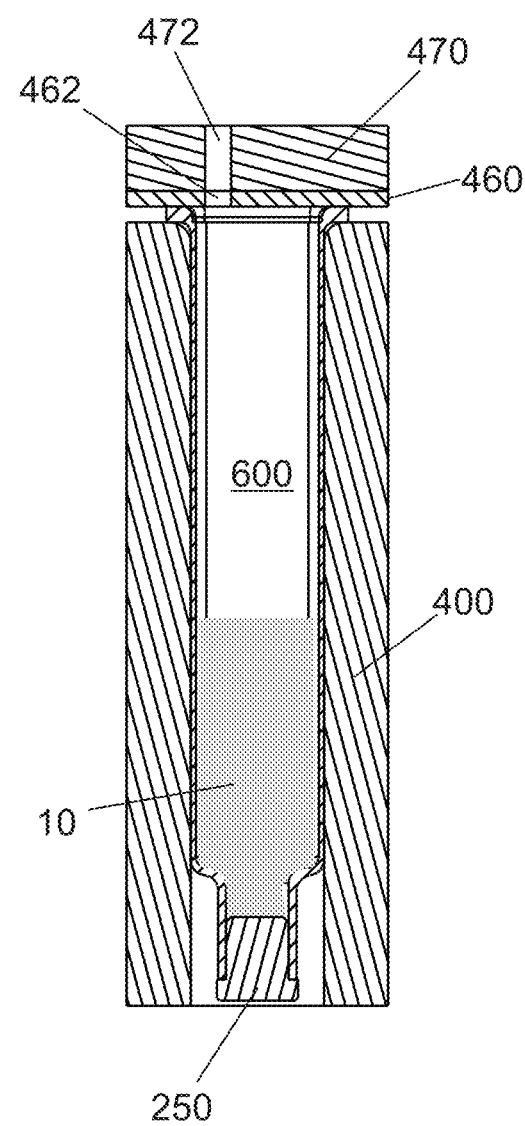
Fig. 65
Fig. 66

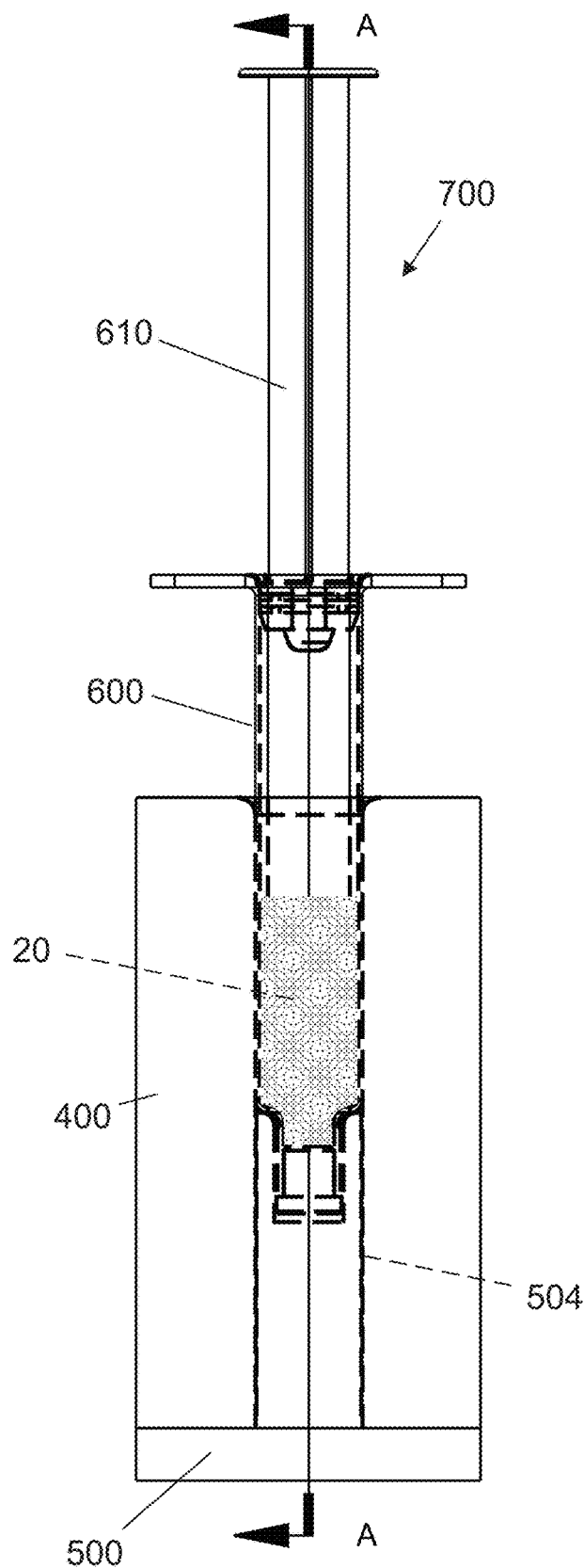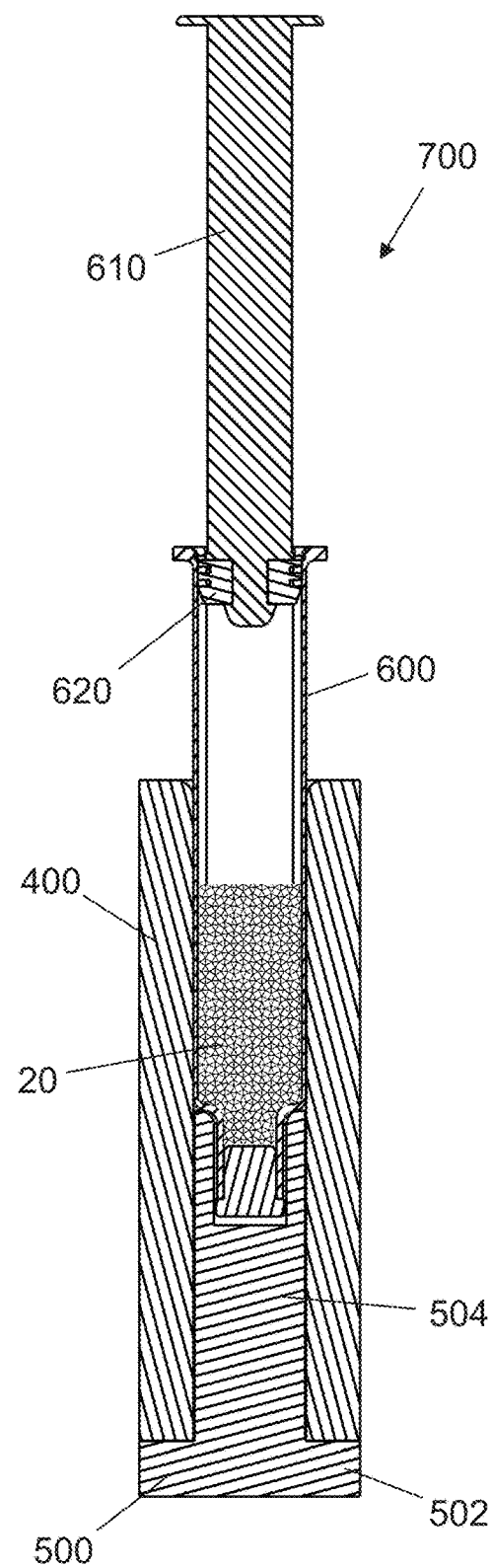
Fig. 73
Fig. 74

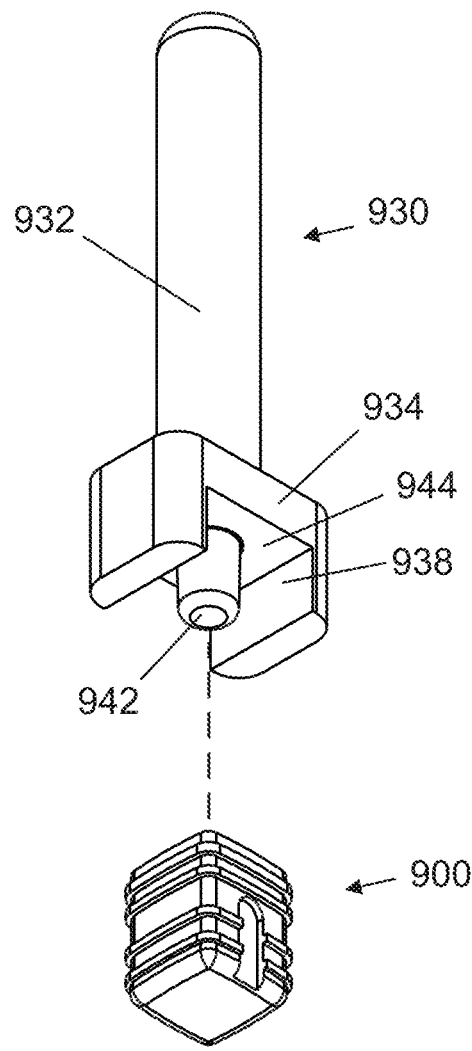
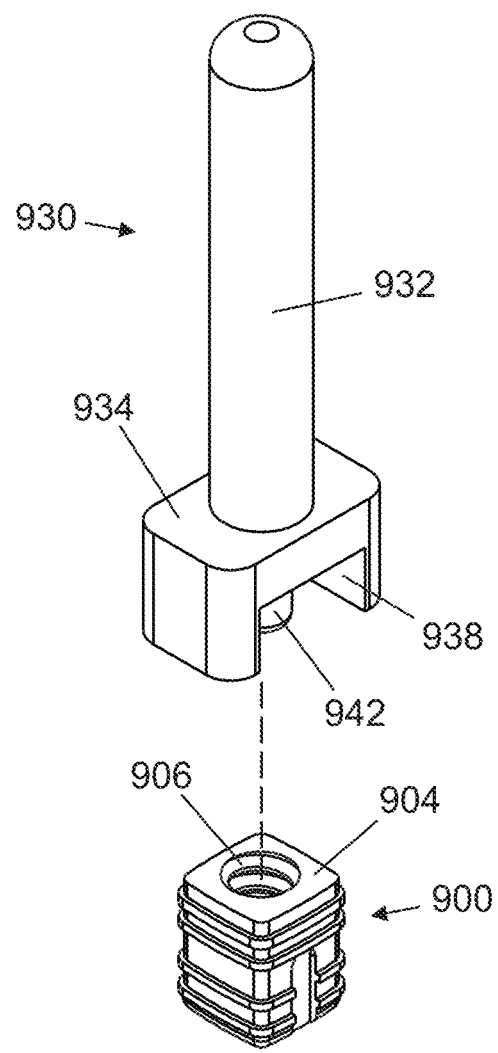
Fig. 91
Fig. 92

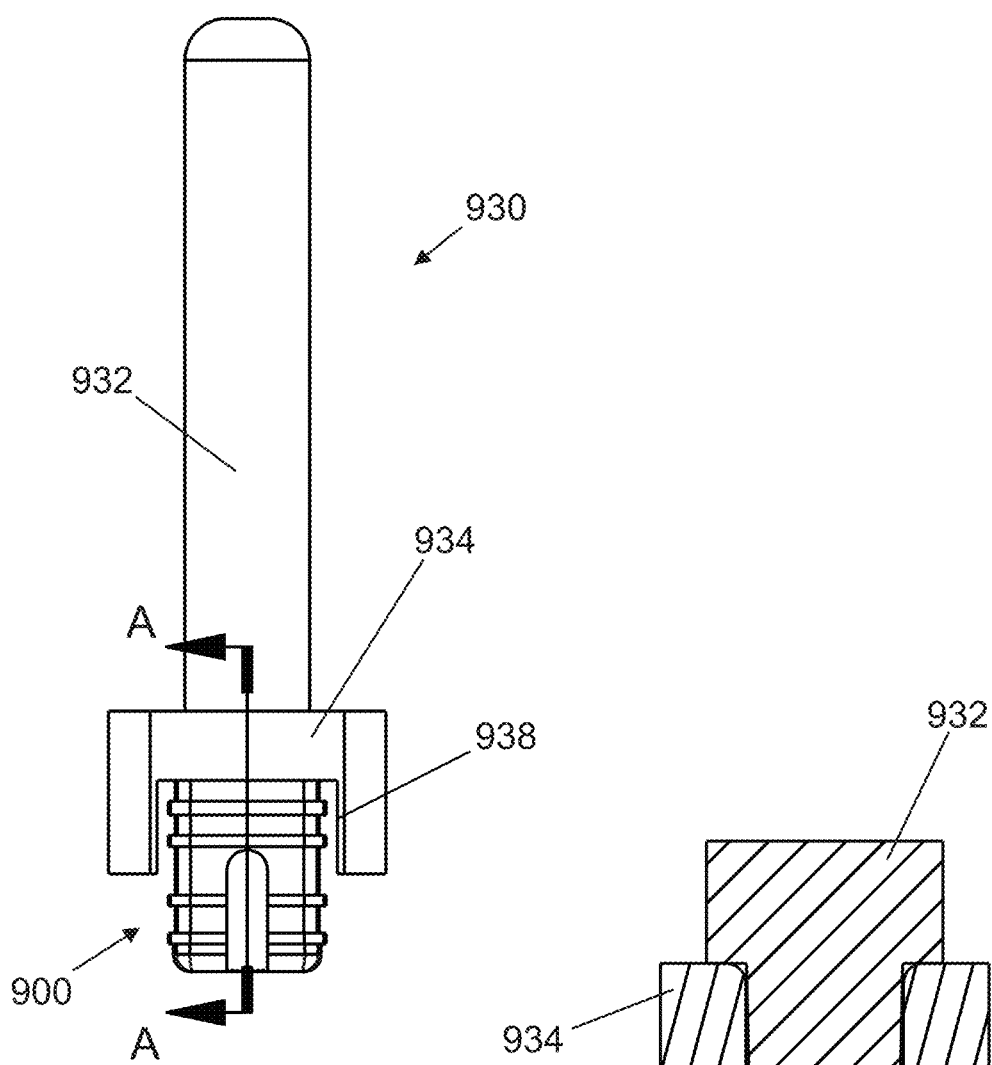
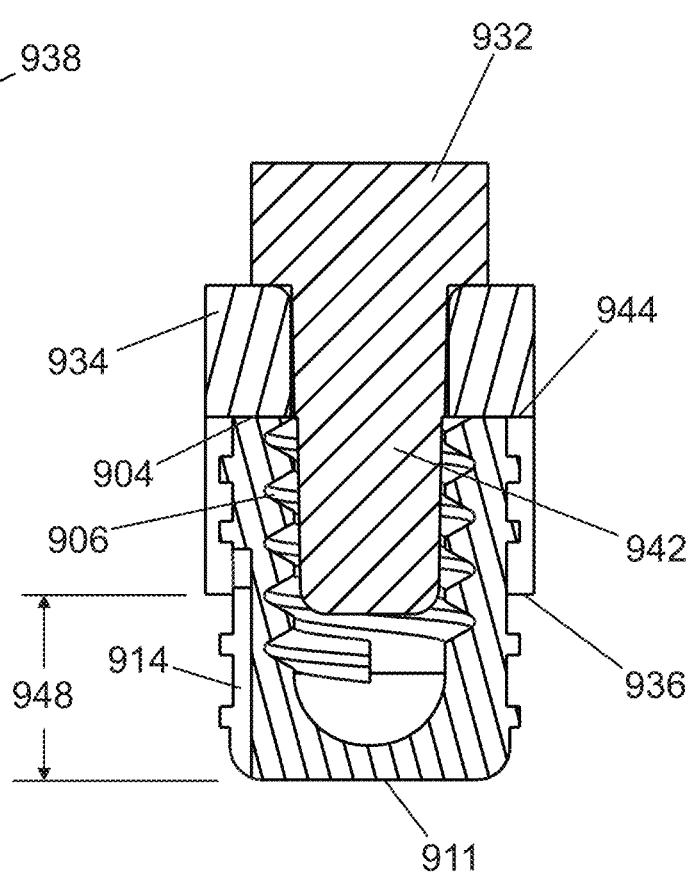
Fig. 93
Fig. 94

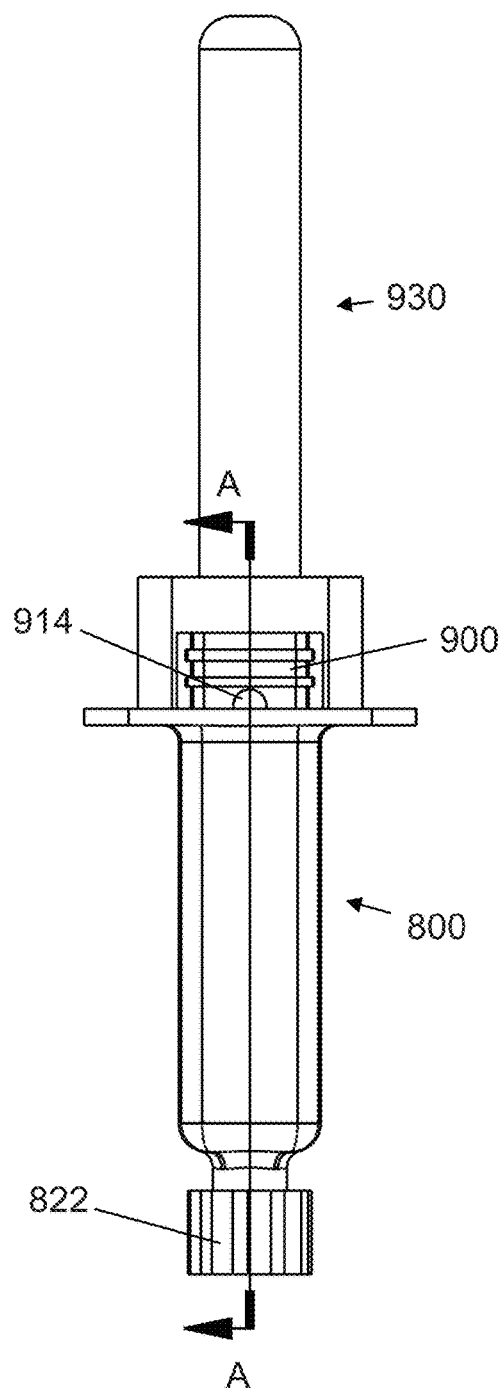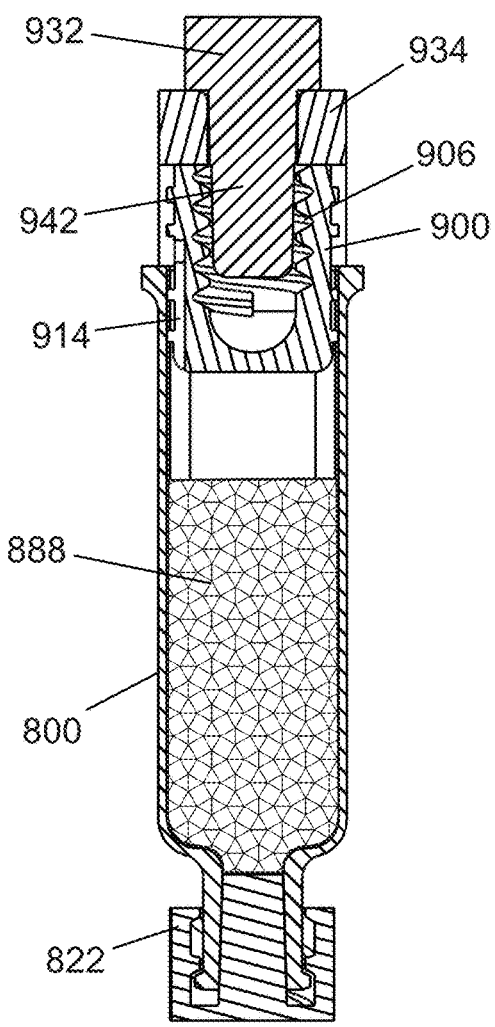
Fig. 114
Fig. 115

US 11,957,790 B1

COMBINATION LYOPHILIZATION AND DISPENSING SYRINGE ASSEMBLY AND METHODS OF USING SAME

I. PRIORITY

This application is a continuation-in-part of U.S. patent application Ser. No. 18/348,675 filed Jul. 7, 2023, which, in turn is a continuation of U.S. patent application Ser. No. 18/066,107 filed Dec. 14, 2022 (which issued as U.S. Pat. No. 11,723,870 on Aug. 15, 2023), which, in turn, is both a continuation-in-part of U.S. patent application Ser. No. 17/588,349 filed Jan. 31, 2022 (which issued as U.S. Pat. No. 11,536,512 on Dec. 27, 2022) and claims the benefit of U.S. Provisional Application No. 63/474,132 filed Jul. 21, 2022. The contents of these prior applications are hereby incorporated by reference in their entirety.

II. TECHNICAL FIELD

The present invention relates to components, assemblies, fixtures, apparatus, and methods for lyophilization. More particularly, the present invention relates to an improved combination lyophilization and dispensing syringe assembly, as well as a dedicated apparatus and methods for lyophilization of materials, particularly biological preparations in liquid form, including but not limited to pharmaceuticals.

III. BACKGROUND OF THE PRESENT INVENTION

Freeze-drying, also known as lyophilization or cryodessication, is a well-known low temperature dehydration process universally accepted across multiple industries, including the chemical, pharmaceutical, and food industries, that involves freezing a product (typically a liquid or water-containing product), lowering pressure, then removing the ice via sublimation. This stands in contrast to the more conventional dehydration processes that use heat to evaporate water in its liquid form.

Primary applications of lyophilization include biological (e.g., bacteria and yeasts), biomedical (e.g., surgical transplants, pharmaceuticals), food processing (e.g., coffee) and preservation. Due to the low temperature used in processing, the quality of the lyophilized product upon rehydration is excellent. Lyophilized products further offer certain advantages such as extended shelf-life and stability which makes the process popular.

The process of lyophilization has been widely adopted in the pharmaceutical industry and more specifically in biological preparations. Most biological preparations are temperature sensitive and have a short shelf life. Other biological formulations, such as vaccines, need to be stored at temperatures as low as −70 to −80° C. or below. Indeed, a first iteration of the Pfizer-BioNTech COVID-19 vaccine required storage at ultra-low freezing temperatures, about −100 degrees Fahrenheit, a temperature that falls well below standard freezer capabilities.

Equipment to maintain such low temperatures for storage and transportation is expensive and often not available. Lyophilized formulations, however, have less temperature stringency and can therefore be stored at temperatures above 0° C. that can be easily maintained in normal refrigerators. Additionally, the lyophilized formulations have a long shelf life, and the dosage remains within pharmaceutical specifications for a longer time. The lyophilized dosage forms can be readily solubilized for easy and dependable administration. This improved stability, extended shelf life, and minimal refrigeration and monitoring requirements during transit and storage make lyophilization processes exceptionally well-suited for preserving and storing biological preparations.

Lyophilization has traditionally been performed in containers, such as vials and ampoules. Lyophilization can also be performed directly in a syringe, with the lyophilized medication being stored in the same syringe. However, convection and radiation, the most common methods for heat transfer in the lyophilization process, are slow processes that tend to be associated with non-uniform heating during batch lyophilization. For example, under typical radiation condition, uneven heat transfer gives rise to higher sublimation rates in those vials or syringes located on the periphery of an array (e.g., at the front and sides of the array) as compared to those more centrally disposed. To wit, it is quite common for a batch to have fully mature hard product cake at the edges of the pan while the center of the batch is soft and raw. This lack of uniformity is highly problematic.

However, pharmaceuticals lyophilized directly in a dispensing syringe are highly preferred for their stability and long shelf life, as well as their convenience. For example, at patient administration, a diluent can be added to the pre-filled syringe for reconstitution of the lyophilized product, thereby allowing the medication to be administered from the lyophilized syringe directly to the patient. Such in-situ lyophilization also reduces labor as compared to preparation of a patient injection from a vial. In addition, product waste is reduced, while a more accurate dosage is administered. As vaccines provided in multidose vials wane in demand and the single-dose vaccine becomes more preferred, lyophilized medicines are uniquely positioned by not requiring the burden of ultra-low temperature freezing for shipment, storage, and product monitoring by expensive temperature sensing systems requiring remote 24/7 surveillance on the product.

Considering the benefits afforded by lyophilization as well as its increasing use in industry, there remains a constant desire, particularly in the pharmaceutical arts, to make the lyophilization process more efficient by reducing the product lyophilization cycle timeline, increasing throughput making the process more economical. During lyophilization, ice formed within a product container is removed by sublimation at the free (upper) surface of the material being lyophilized. The rate of sublimation is strongly affected by the surface area of the material with a larger surface area resulting in faster lyophilization and reduction in lyophilization cycle times. Accordingly, the time required for complete lyophilization of a product is strongly dependent on the ratio of surface area to the total volume of the material being processed.

To that end, in conventional lyophilization procedures, standard "round barreled" syringes of the prior art are processed in a vertical orientation. However, in this orientation, the ratio of the surface area to the total product volume is extremely low, which extends the time required for complete lyophilization of materials therein. Arranging the cylindrical syringe barrels or vials in a horizontal orientation can increase the free surface available for sublimation. However, in order to prevent leakage and undue pressure build up, the lyophilization container must have a venting channel formed therein, and also must have means to ensure that the venting channel is oriented upwards during processing. This is difficult to accomplish with standard cylindrical vessels that freely rotate and/or lack a reference surface for alignment of the requisite venting features with the syringe barrel. These difficulties are overcome with lyophilization syringe assemblies of the present invention.

IV. SUMMARY OF THE PRESENT INVENTION

U.S. Pat. Nos. 11,536,512 and 11,723,870, the contents of which are incorporated by reference herein, describe embodiments in which lyophilization rates are increased by inserting the vial or syringe barrel into a block such as described below, wherein the block removes heat by conduction during lyophilization and by orienting the vial or syringe barrel axis horizontal during processing for increased free surface area. The relative contributions of heat conduction and surface area increase are strongly affected by the syringe configuration. However, as demonstrated herein, the present invention contemplates further embodiments wherein the lyophilization rate is increased solely by the increased free surface area of the material being processed, this area of increase being achieved by orienting the vial or syringe with the axis horizontal or at a predetermined angle to horizontal. Similarly, in previously described embodiments, lyophilized product is exposed to external atmosphere at some point before solubilization in preparation for use. However, alternate embodiment syringes and methods of the present invention allow lyophilization of material within the syringe, sealing of the syringe for storage and shipping, solubilization of the lyophilized material, and administering to a patient without the lyophilized material being exposed to the external atmosphere at any point.

Bearing in mind the above, the present invention offers an improvement over the state of the art by utilizing an apparatus and methodology whereby lyophilization cycles can be shortened using novel design techniques and materials.

Accordingly, it is a primary objective of the present invention to provide a lyophilization assembly, apparatus and method that imparts a shorter lyophilization cycle timeline. A second important objective of the present invention is for the lyophilization method to be efficient. It is still yet another objective of the present invention to provide a readily scalable lyophilization apparatus and method. It is yet a further objective of the present invention to provide a lyophilization assembly, apparatus and process that affords uniformity in all units of a lyophilization batch. It is yet a further objective of the present invention to provide single use syringes assemblies that can serve as combination lyophilization vessel, storage and transportation container, and dispensing vehicle.

Embodiments of the present invention that meet one or more of the foregoing objectives are summarized below. However, this simplified summary of one or more embodiments of the present invention is intended to provide a basic understanding of such embodiments and thus is not meant to be an extensive overview of all contemplated embodiments. Nor is the following summary intended to identify key or critical elements of all embodiments nor to delineate the scope of any or all embodiments. Rather, its sole purpose is to present some concepts of one or more embodiments in a simplified form as a prelude to the more detailed description that is presented later.

In a first aspect, the present invention provides a lyophilization assembly, apparatus and method having optimized lyophilization cycle timelines and thereby shortened into more favorable timelines, wherein the lyophilization assembly includes a thermal block made from heat conductive material, preferably a material having high heat conductivity. In preferred embodiments, the thermal block includes a plurality of identical wells evenly arrayed across multiple rows, wherein the wells are configured to receive containers for lyophilization that contain products to be lyophilized.

In preferred embodiments, the wells are sized and shaped to closely approximate the dimensions of the corresponding containers, more particularly to cause deformation to a polymeric container placed therein. In this manner, substantial contact is created between the outer walls of each container and the interior walls of its respective well which, in turn, allows heat to be evenly transferred at a faster rate from the block to the containers and finally to the product in the containers.

In certain embodiments, both the wells and the containers are square-shaped, such that the square-shaped containers can closely fit into the square-shaped wells. In other embodiments, both the wells and containers exhibit coordinating rounded profiles. In either case, the containers preferably take the form of a syringe barrel in which the product can be lyophilized directly.

Thus, in view of the above, it is an objective of the present invention to provide a lyophilization syringe assembly suitable for in situ lyophilization of an initial product as well as reconstitution and dispensing of a lyophilized product. In certain preferred embodiments, the syringe is composed (i) an elongate central barrel having a hollow bore configured to retain the initial product to be lyophilized and optionally provided with a wide radial flange at its proximal end; (ii) an open distal tip configured to engage a hypodermic needle assembly and optionally sealed by a distal cap, such as Luer cap, and (iii) an open proximal end configured to receive and/or include a vented stopper that may be optionally coupled to stem element to form an aspirating and dispensing plunger mechanism.

In certain preferred embodiments, the central barrel optionally has a non-circular, non-uniform, or polygonal cross-section, preferably a substantially square cross-section characterized by four elongate side panels that optionally bow outward to form a convex exterior surface. Other embodiments of the present invention contemplate conventional "round barreled" syringes.

Prior to lyophilization, the vented stopper may removably mounted to the open proximal end, whereby when said stopper is partially inserted into the proximal opening, a passage for gaseous outflow from the container interior is formed, thereby providing an escape path for outgassing during the lyophilization process, further wherein the passage is closed when the stopper is distally and/or fully inserted into the proximal opening, such that the lyophilized product is sealed within the container interior. After lyophilization, the stopper is axially slid along the barrel in a distal direction to a second axial position referred to as the "sealed" position in which the stopper is distally or fully inserted into the syringe barrel so as to provide an airtight seal against surrounding atmosphere and potential contamination. During the life cycle of the syringe assembly, the lyophilized material is never exposed to the atmosphere. The syringe assembly can thus be securely stored and transported while preventing exposure to contamination of the material.

In certain preferred embodiments, the stopper is provided with a threaded cavity formed in its proximal end that is adapted to engage an optional, separately packaged elongate stem configured with a compatible threaded distal end. In certain embodiments, the stem may be supplied to the user along with the sealed syringe barrel. Likewise, the filled syringe assembly and associated stem may be shipped to the location to be dispensed to a patient. At time of use, the elongate stem is threaded into the proximal face of the stopper, converting it from a "stopper" to "stopple" component of a dispensing plunger. In this manner, the filled syringe assembly and elongated stem now form a fully functioning syringe.

The lyophilized syringes and syringe assemblies find utility in conjunction with the lyophilization apparatus and methods described in U.S. Pat. Nos. 11,536,512 and 11,723,870. As such, it is a further objective to provide a method for lyophilization that utilizes the aforementioned lyophilization assembly to lyophilize a product in situ, wherein the method includes the steps of:

a. placing one or more containers in an upright position (i.e., vertical orientation) into the plurality of wells, wherein the open proximal end faces up;

b. via the respective open proximal ends, filling each container with an initial liquid product to be lyophilized;

c. mounting a stopper in each respective open proximal end in a first axial vented position in which vapors are allowed to escape from the one or more containers while preventing product from leaking;

d. optionally rotating the lyophilization assembly from the vertical orientation, wherein the proximal ends face up, to the horizontal orientation, wherein proximal ends face sideways, so as to enhance the efficiency of the lyophilization process; and e. applying heat to the thermal block until all water is removed from the product to be lyophilized.

In an alternate embodiment, the present invention provides a "full circle" lyophilization and dispensing method in which a single syringe is used to both lyophilize an initial liquid preparation into a lyophilized product and subsequently rehydrate and dispense the lyophilized product in rehydrated form, wherein the method includes the steps of:

a. introducing the liquid preparation into a hollow interior bore of a lyophilization syringe having an open distal tip configured to engage a hypodermic needle assembly, and an open proximal end configured to removably receive a stopper;

b. affixing a distal cap to the open distal tip;

c. partially inserting a stopper into the open proximal end of the elongate central barrel to a first axial position so as to form a passage whereby gas may flow out from the central barrel and through the member, wherein the stopper has (i) at least one vent channel disposed along a lateral surface that serves as said passage whereby gas may flow out from the central barrel and through the member, (ii) at least one sealing rib circumferentially disposed about a lateral surface at a position that is proximal to a distal end of the at least one vent channel; and (iii) optionally a threaded socket formed in a proximal surface of the stopper;

d. lyophilizing the liquid preparation into a lyophilized product in situ;

e. axially sliding the stopper along the barrel in a distal direction to a second axial position wherein the at least one vent channel is closed and the lyophilized product is sealed within said central barrel;

f. attaching a demountable stem to the threaded socket of the stopper whereby the stopper forms the piston element of a plunger mechanism;

g. manipulating the plunger mechanism so as to draw liquid into the central barrel via the open distal tip so as to rehydrate the lyophilized product.

h. manipulating the plunger so as to dispense the rehydrated contents from the central barrel.

These and other objectives and features of the invention will become more fully apparent when the following detailed description is read in conjunction with the accompanying figures and examples. However, it is to be understood that both the foregoing summary of the invention and the following detailed description are of a preferred embodiment, and not restrictive of the invention or other alternate embodiments of the invention. In particular, while the invention is described herein with reference to a number of specific embodiments, it will be appreciated that the description is illustrative of the invention and is not constructed as limiting of the invention. Indeed, various modifications and applications will readily occur to those who are skilled in the art, without departing from the spirit and the scope of the invention, as described by the appended claims. In addition, those skilled in the art will recognize that one or more aspects of this invention can meet certain objectives, while one or more other aspects can meet certain other objectives. Moreover, each objective may not apply equally, in all its respects, to every aspect of this invention. As such, the preceding objectives and subsequently presented preferred embodiments can be viewed in the alternative with respect to any one aspect of this invention.

V. BRIEF DESCRIPTION OF THE FIGURES

Various aspects and applications of the present invention will become apparent to the skilled artisan upon consideration of the brief description of figures and the detailed description of the present invention and its preferred embodiments that follows:

FIG. 38 depicts a third step in lyophilization methods of the present invention in which the syringe barrel with proximal stopper in the "venting" position is placed in the well of the thermal block of FIG. 31.

FIG. 39 is a sectional view of the objects of FIG. 38 at location A-A.

FIG. 40 is an expanded sectional view of the objects of FIG. 38 at location B-B.

FIG. 59 depicts a syringe barrel of the present invention with lyophilized material formed using methods of the present invention.

FIG. 60 is a sectional view of the objects of FIG. 59 at location A-A.

FIG. 65 depicts a second step of the alternate lyophilization method wherein a gasket and plate are positioned on the thermal block segment.

FIG. 66 is a sectional view of the objects of FIG. 65 at location A-A.

FIG. 73 depicts an eight step in which the sealed syringe is partially ejected from the thermal block segment.

FIG. 74 is a sectional view of the objects of FIG. 73 at location A-A.

FIG. 91 is a lower perspective view of the insertion tool of FIG. 88 and the stopper of FIG. 83 positioned for placement of the stopper on the tool in preparation for use.

FIG. 92 is an upper perspective view of the objects of FIG. 91.

FIG. 93 is a side elevational view of the tool of FIG. 88 with the stopper of FIG. 83 mounted thereto in preparation for use.

FIG. 94 is a sectional view of the objects of FIG. 93 at location A-A of FIG. 93.

Figure 81:
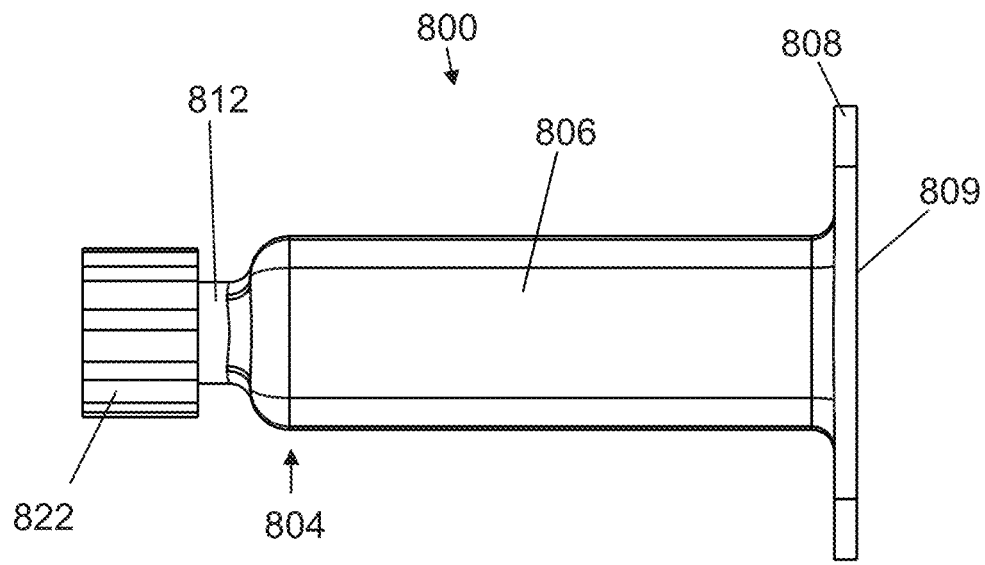
FIG. 81 is a plan view of the syringe barrel of FIG. 79 with a conventional Luer cap mounted to its distal end.
Figure 83:
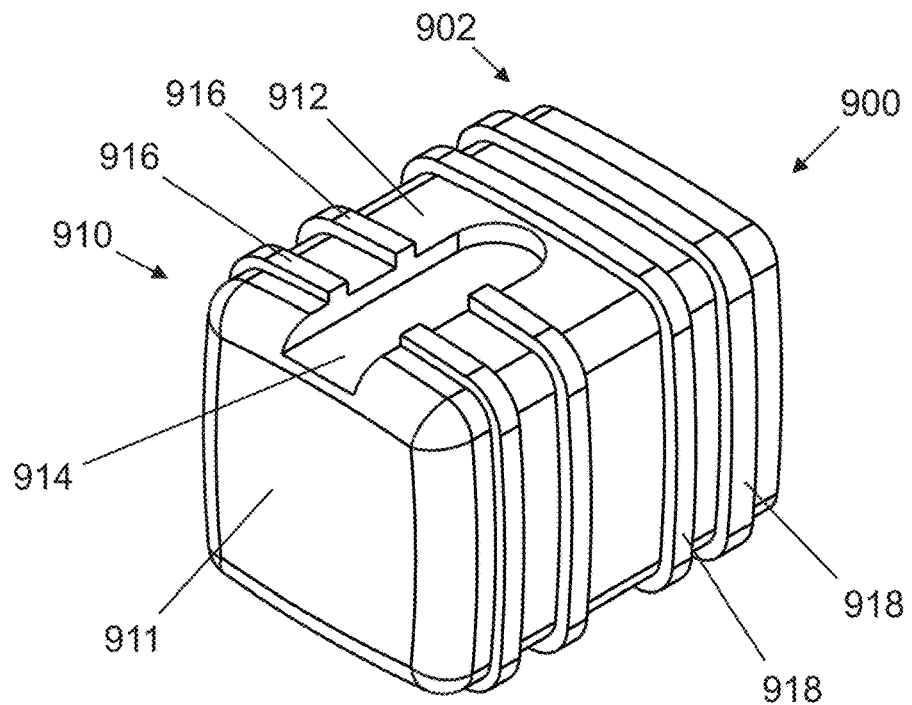
FIG. 83 is a distal perspective view of a stopper for use in connection with the combination lyophilization and dispensing syringe of the present invention.
Figure 84:
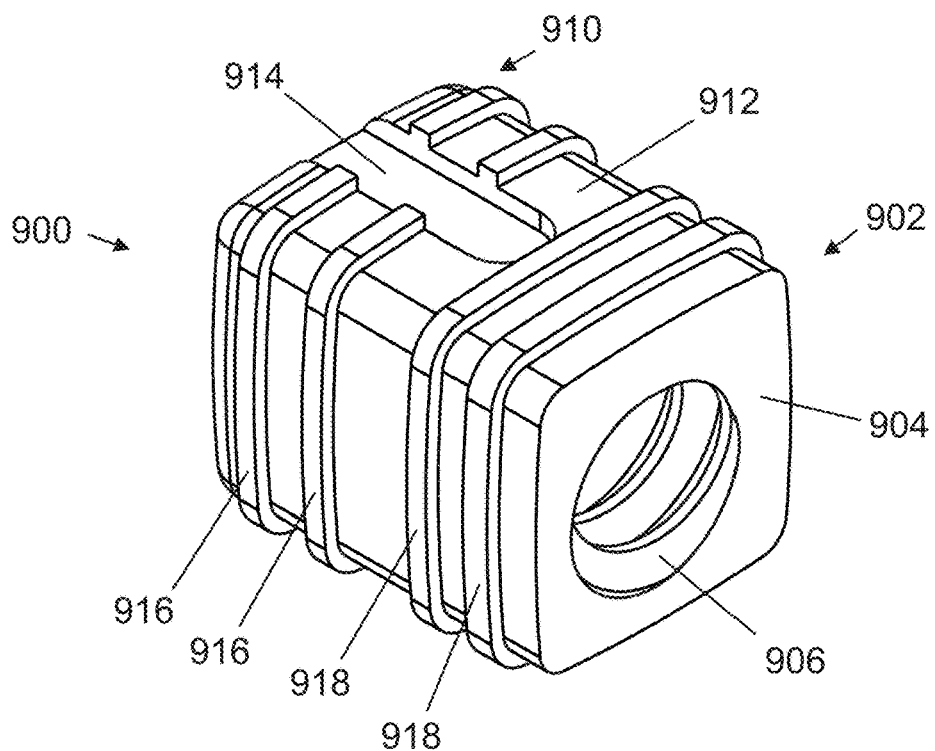
FIG. 84 is a proximal perspective view of the stopper of FIG. 83.
Figure 85:
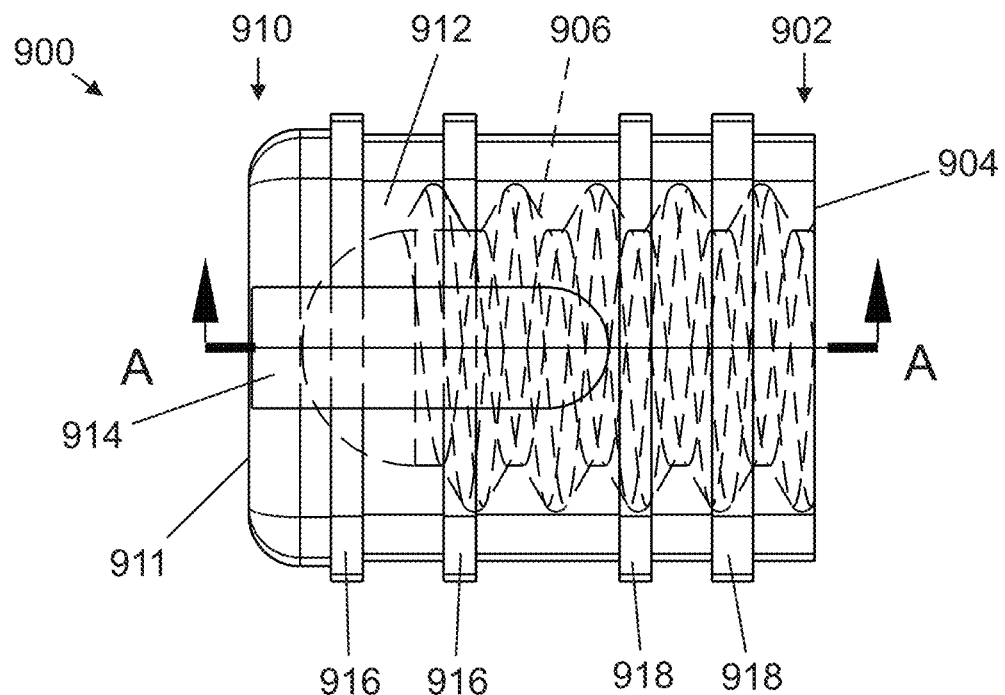
FIG. 85 is a plan view of the stopper of FIG. 83.
Figure 86:
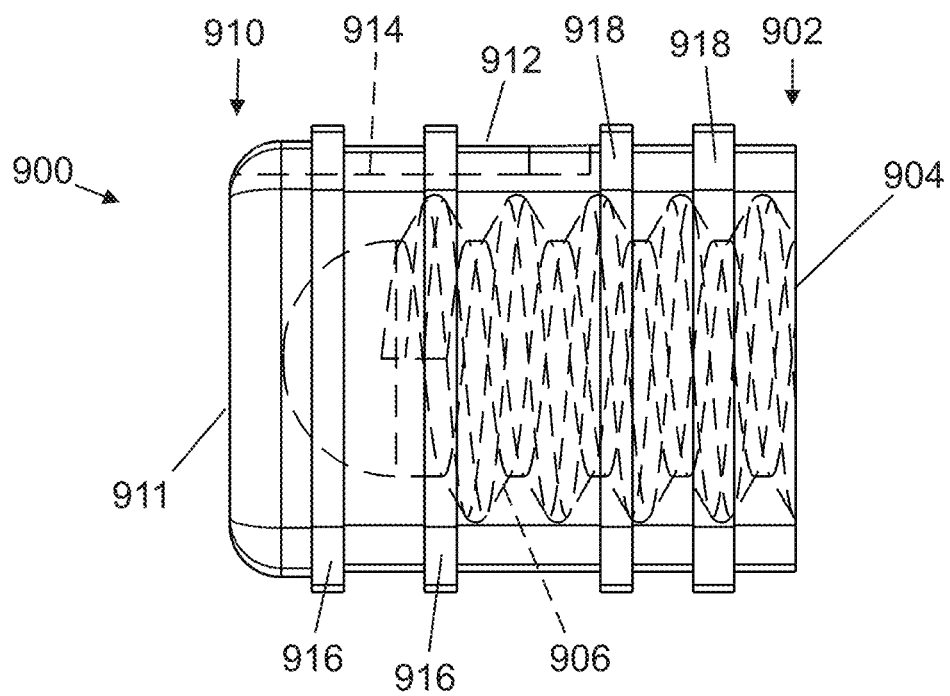
FIG. 86 is a side elevational view of the stopper of FIG. 83.
Figure 87:
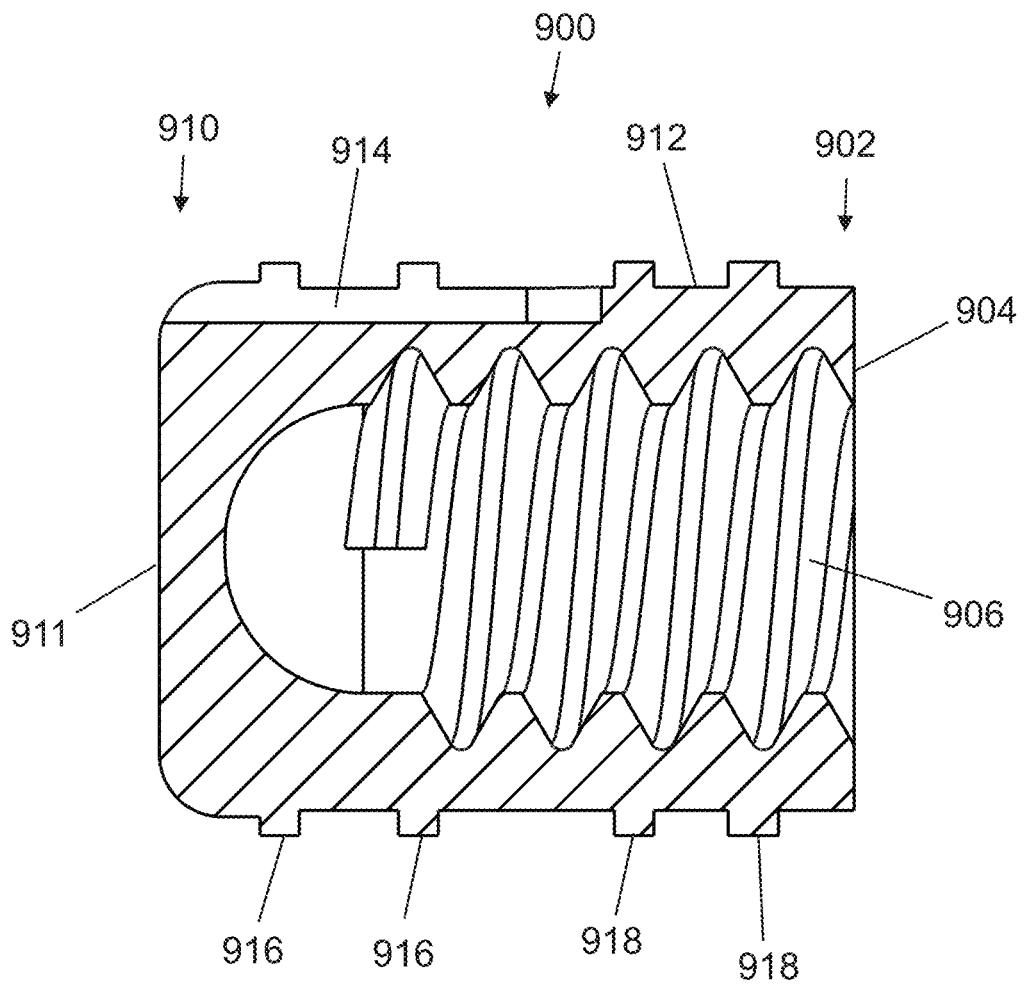
FIG. 87 is a sectional view of the object of FIG. 85 at location A-A.
Figure 102:
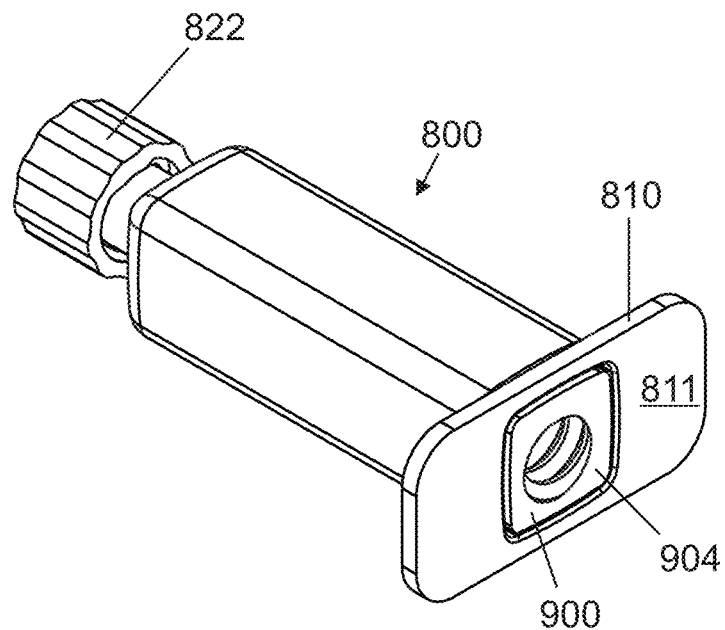
FIG. 102 is a proximal perspective view of the stopper of FIG. 83 placed in the proximal end of the barrel of FIG. 79 in a second axial "sealed" position.
Figure 103:
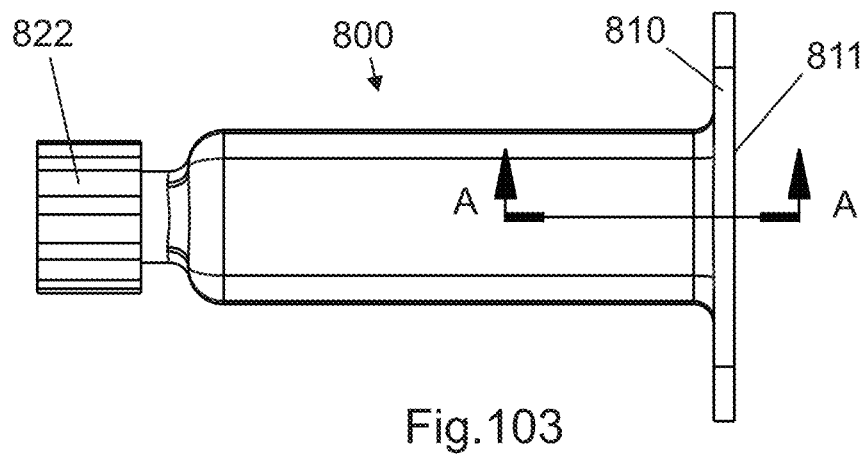
FIG. 103 is a plan view of the objects of FIG. 102.
Figure 104:
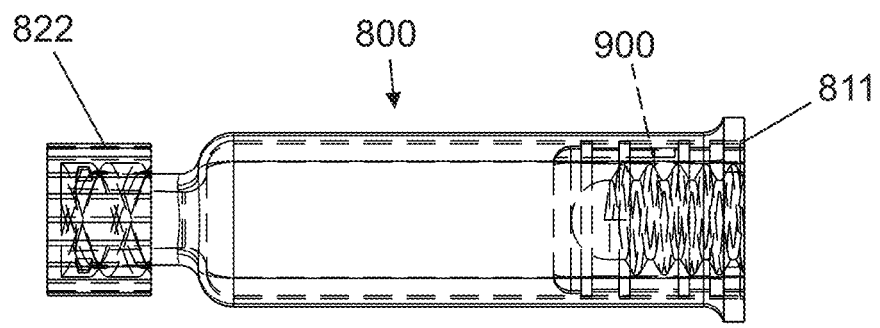
FIG. 104 is a side elevational view of the objects of FIG. 102.
Figure 106:
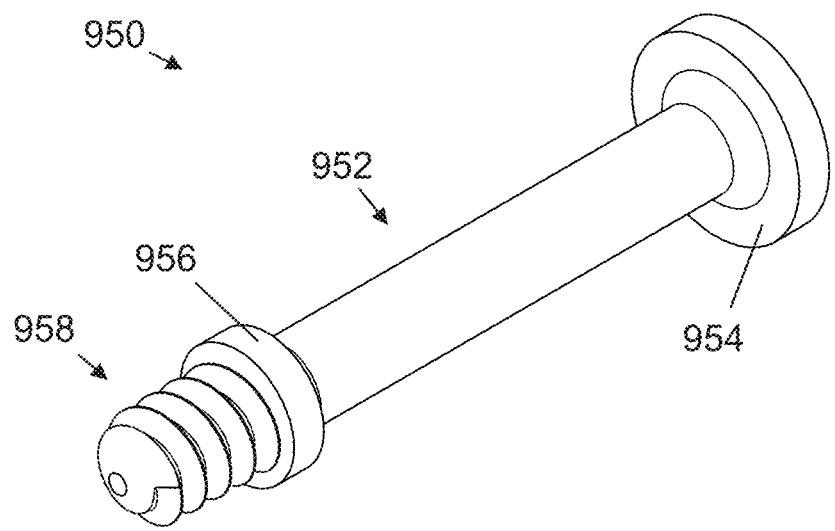
FIG. 106 is a perspective view of a stem that may be mounted to the proximal end of the stopper of FIG. 83 to form the plunger for the combination lyophilization and dispensing syringe assembly of the present invention.
Figure 108:
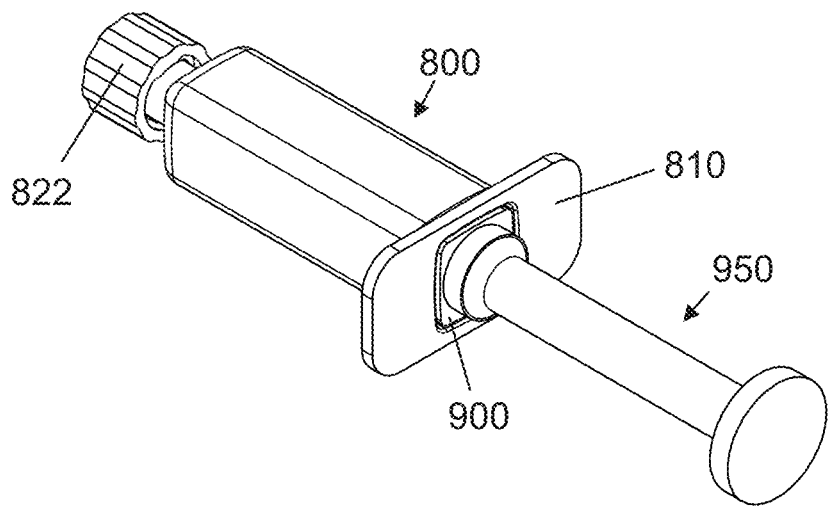

FIG. 108 is a perspective view of an assembled lyophilization and dispensing syringe of the present invention composed of (1) a syringe barrel with Luer cap such as depicted in FIG. 81, (2) a stopper such as depicted in FIG. 83 mounted to the proximal end of the syringe barrel in the "sealed" arrangement such as depicted in FIG. 102, and (3) a stem such as depicted in FIG. 106 mounted to the proximal side of the stopper.

Figure 109:
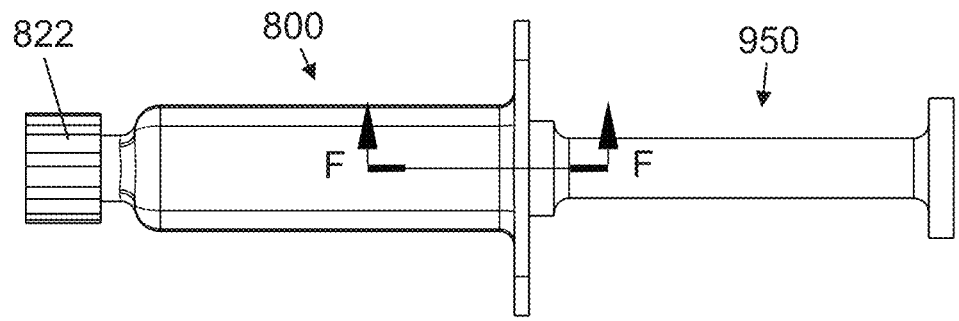

FIG. 109 is a plan view of the objects of FIG. 108.

Figure 110:
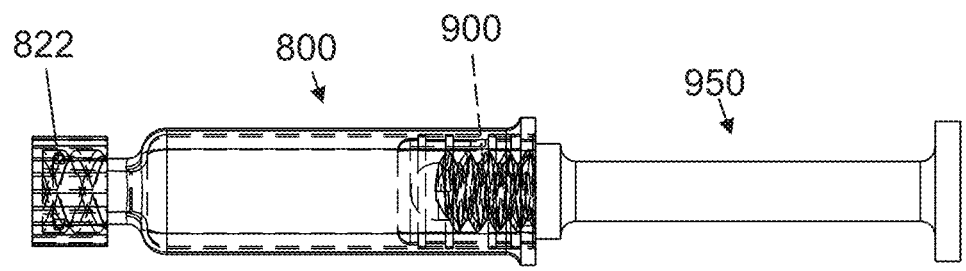

FIG. 110 is a side elevational view of the objects of FIG. 108.

Figure 111:
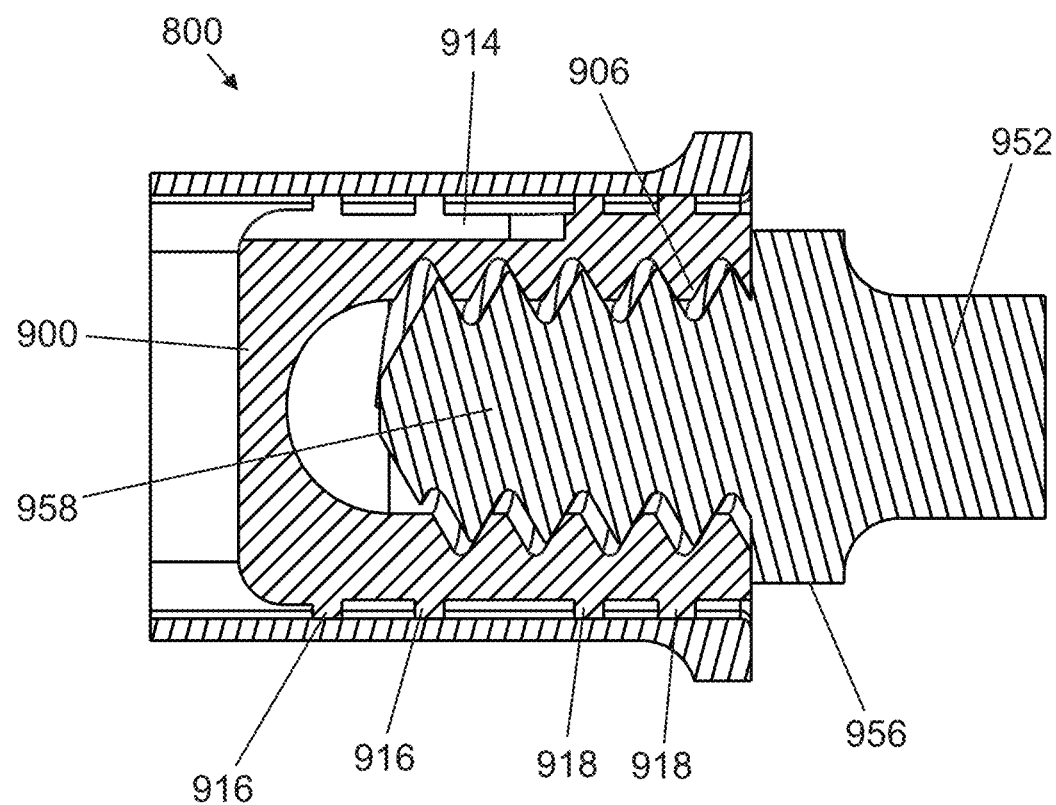

FIG. 111 is an expanded sectional view of the objects of FIG. 109 at location F-F.

Figure 112:
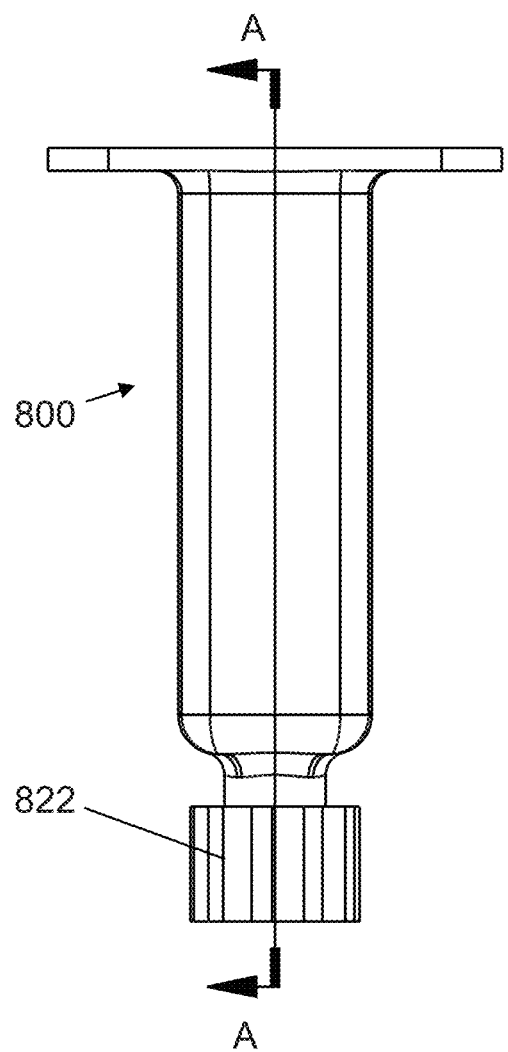

FIG. 112 is a side elevational view of the barrel and Luer cap of FIG. 81 containing a liquid product to be lyophilized arranged in a vertical orientation as a first step in a lyophilization method of the present invention.

Figure 113:
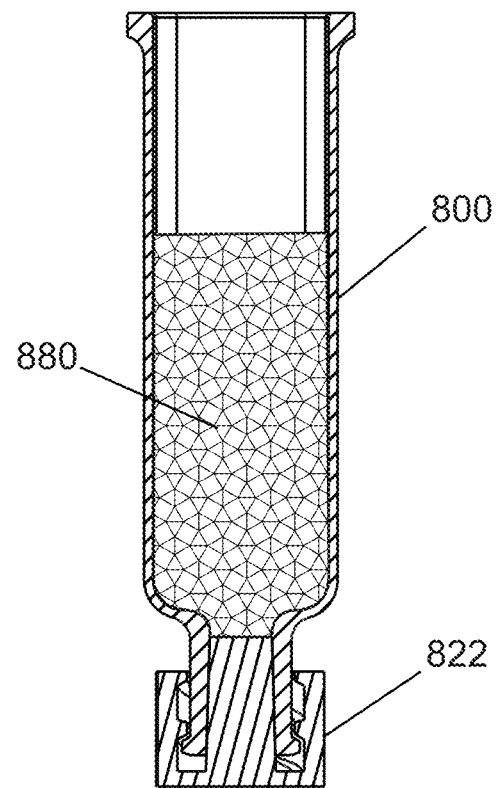

FIG. 113 is a sectional view of the objects of FIG. 112 at location A-A.

Figure 95:
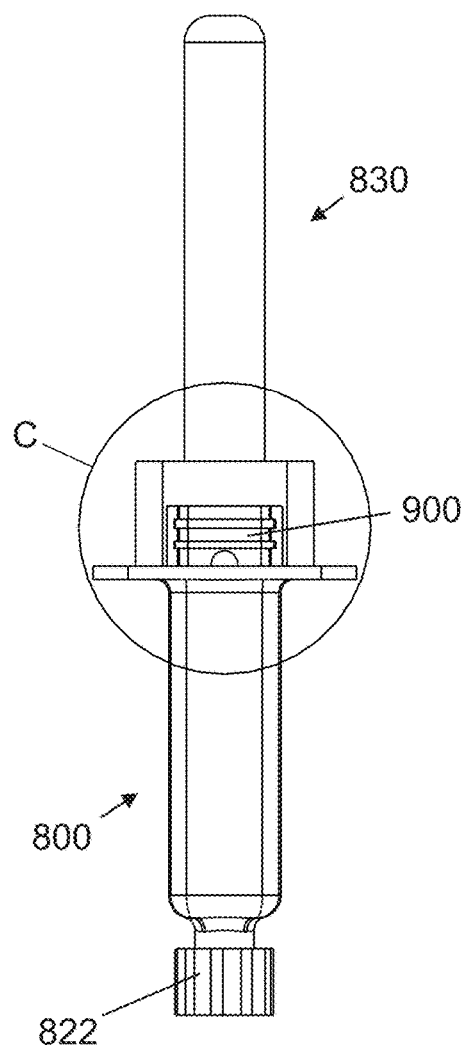
FIG. 95 is a side elevational view of the stopper of FIG. 83 mounted to the proximal end of the syringe barrel of FIG. 79 using the tool of FIG. 88, the stopper being placed in a first "venting" position.
Figure 96:
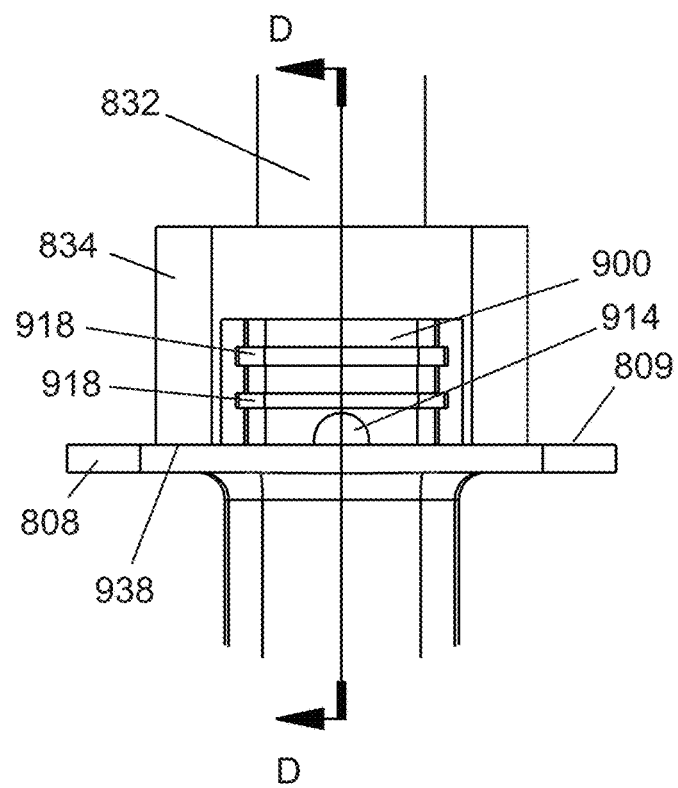
FIG. 96 is an expanded view of the objects of FIG. 95 at location C.
Figure 97:
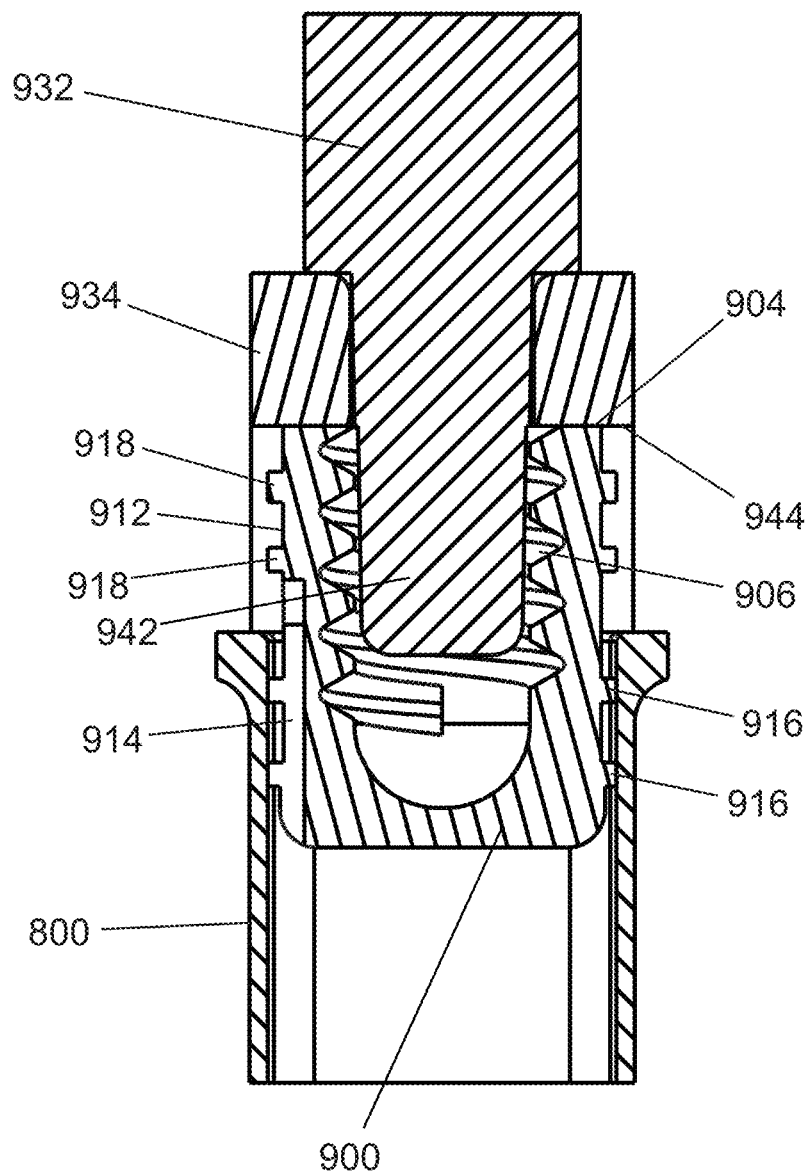
FIG. 97 is a sectional view of the objects of FIG. 96 at location D-D.
Figure 98:
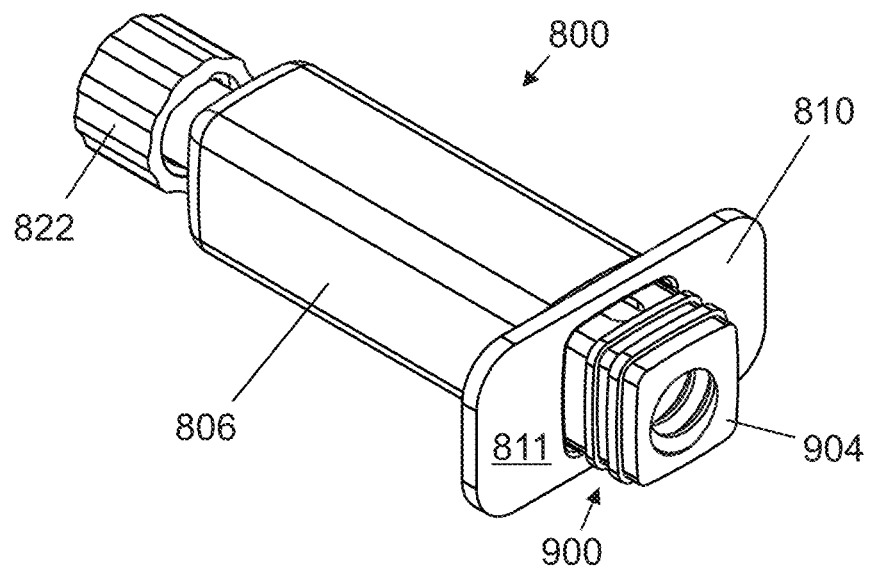
FIG. 98 is a proximal perspective view of the stopper of FIG. 83 placed in the barrel of FIG. 79, in a first axial "venting" position.
Figure 99:
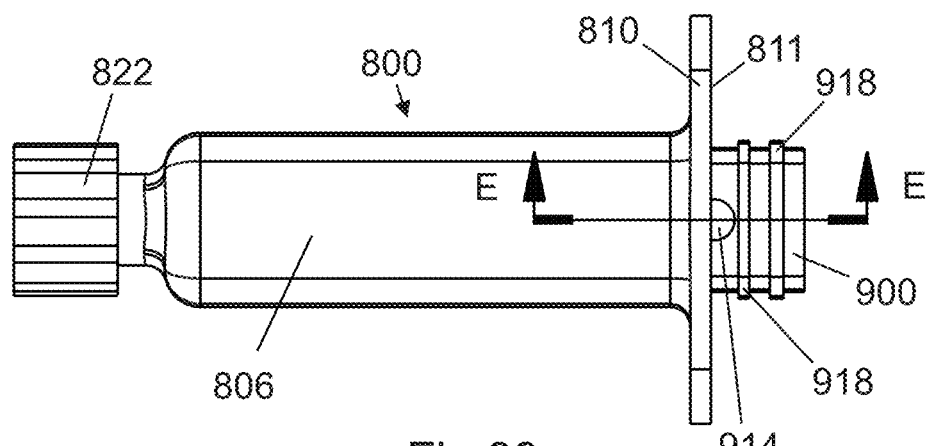
FIG. 99 is a plan view of the objects of FIG. 98.
Figure 100:
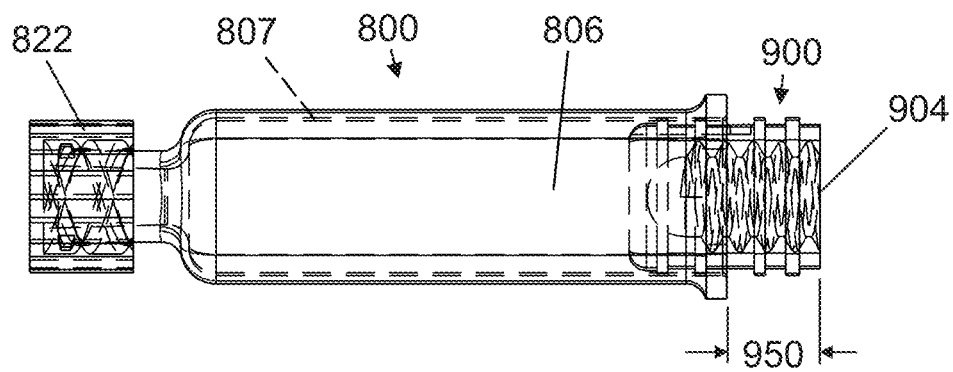
FIG. 100 is a side elevational view of the objects of FIG. 98.
Figure 101:
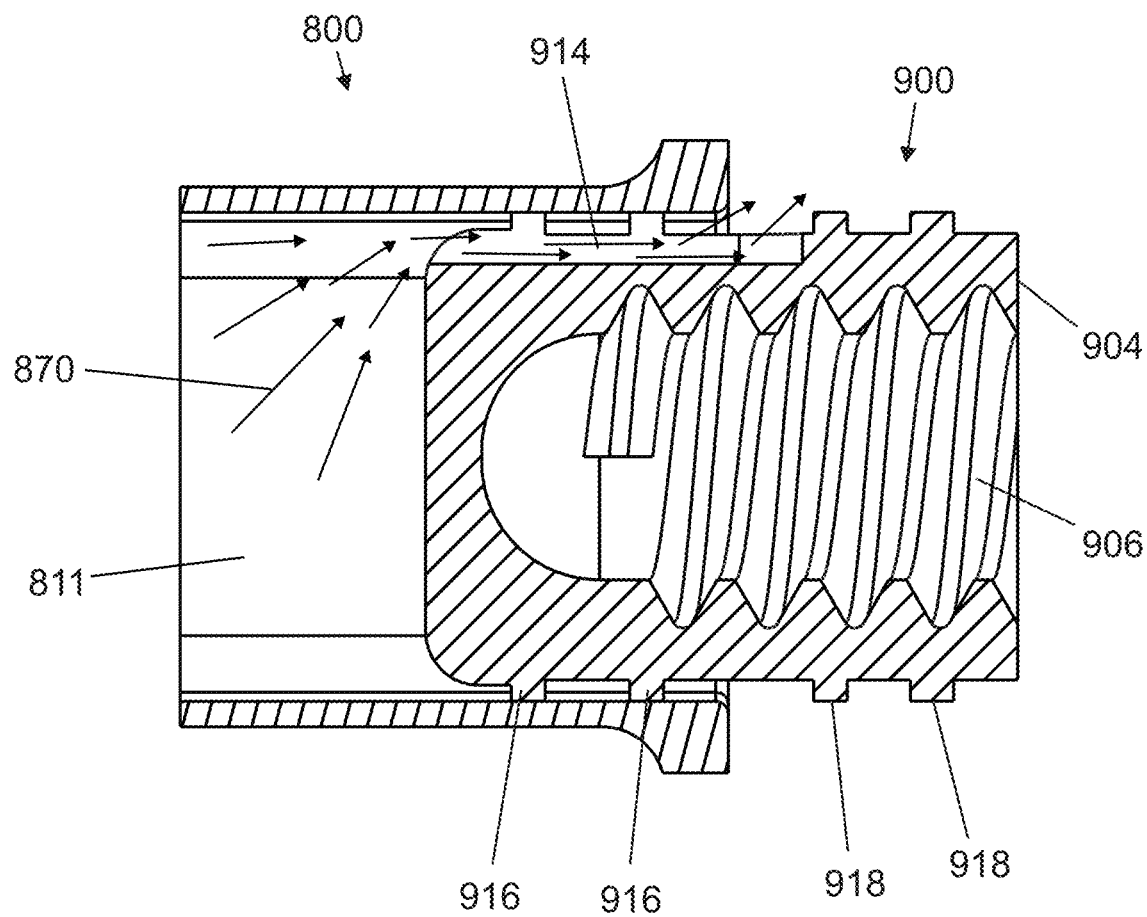
FIG. 101 is an expanded sectional view of the objects of FIG. 99 at location E-E.

FIG. 114 is a side elevational view of the stopper of FIG. 93 inserted into the vertically oriented, liquid product-containing barrel of FIG. 112 (wherein the syringe barrel is as previously depicted in FIGS. 95 through 97).

FIG. 115 is a sectional view of the objects of FIG. 114 at location A-A.

Figure 116:
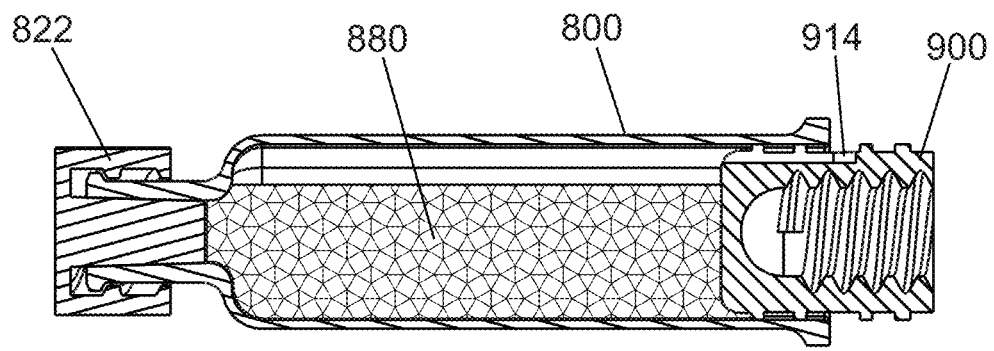

FIG. 116 is a side elevational sectional view of the barrel, Luer cap, stopper and liquid material contained therein rearranged to the horizontal orientation in a first "venting" position, such as depicted in FIGS. 98 through 101, in preparation for lyophilization.

Figure 117:
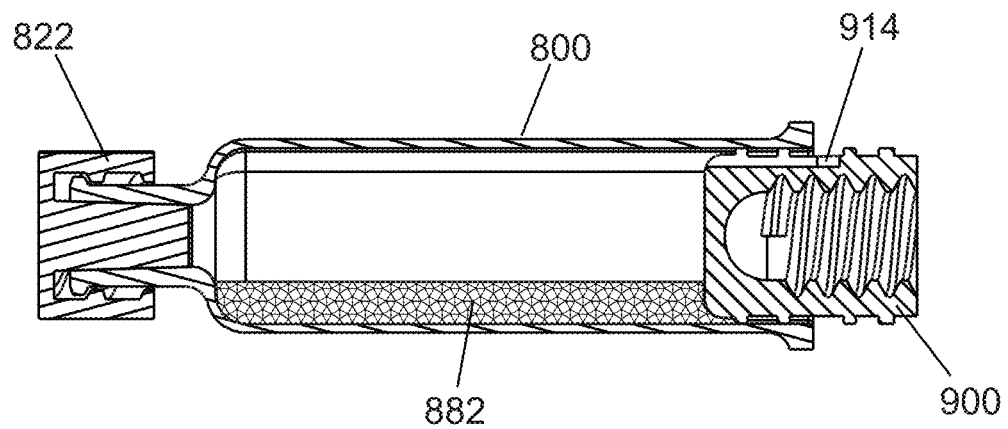

FIG. 117 is a side elevational sectional view of the objects of FIG. 116 at the completion of lyophilization, with the product now in lyophilized form contained therein.

Figure 118:
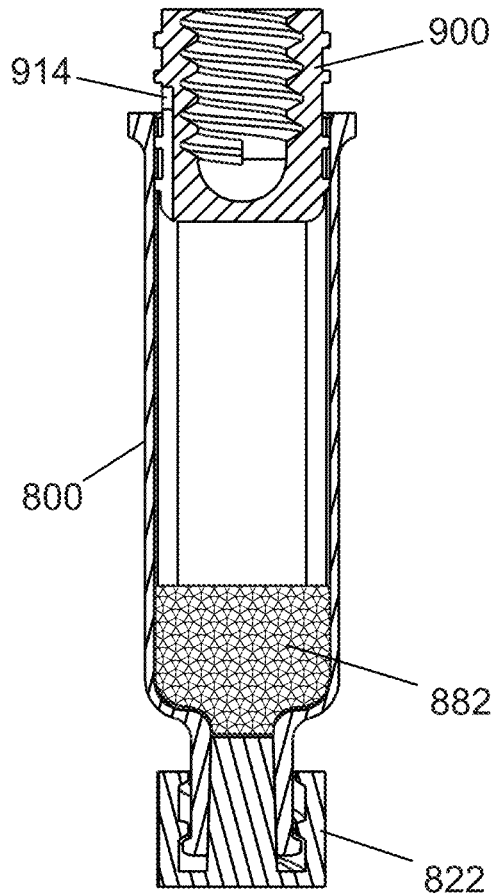

FIG. 118 is a side elevational sectional view of the objects of FIG. 117 rearranged to the vertical orientation.

Figure 119:
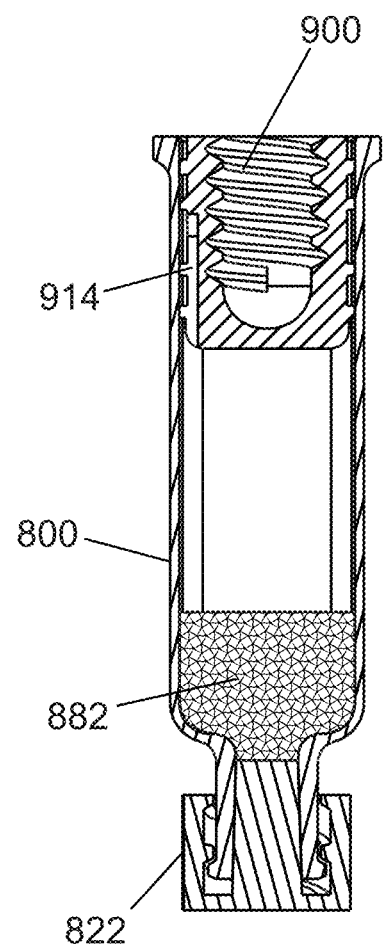

FIG. 119 is a side elevational sectional view of the objects of FIG. 118 with the stopper advanced into the barrel, from the first "venting" position to the second "sealed" position as depicted in FIGS. 102 through 105.

Figure 107:
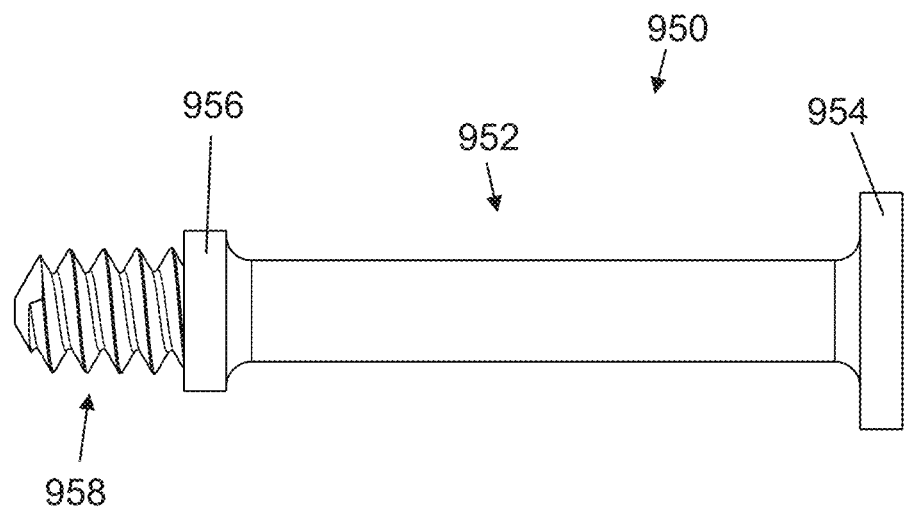
FIG. 107 is a side elevational view of the stem of FIG. 106.
Figure 120:
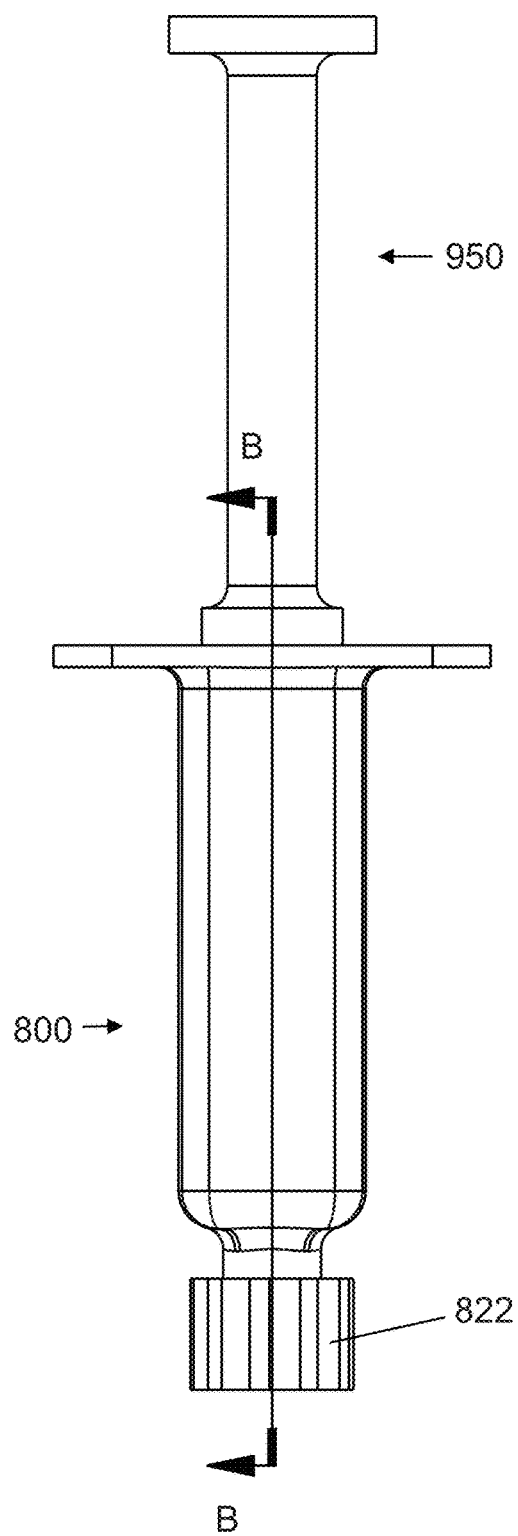

FIG. 120 is a side elevational view of an assembled lyophilization/dispensing syringe of the present invention formed by adding the stem of FIGS. 106 and 107 to the syringe containing lyophilized product via the stopper of FIG. 83 as previously described.

Figure 121:
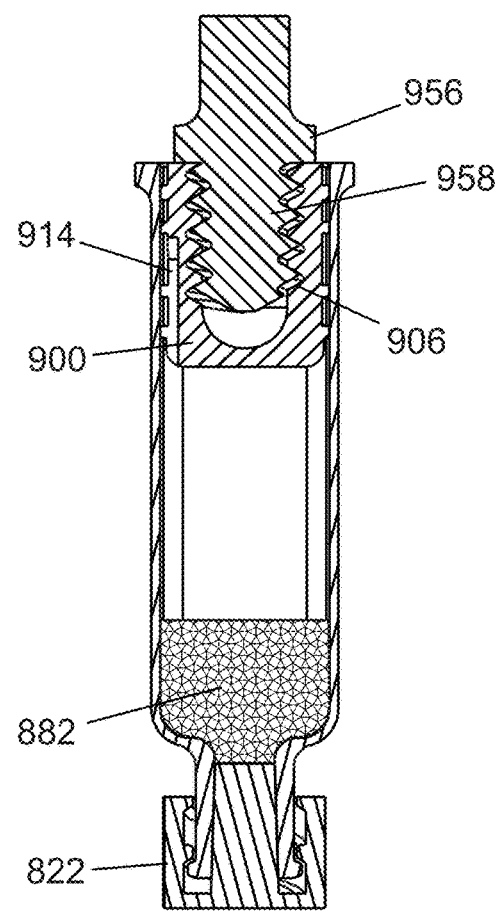

FIG. 121 is a sectional view of the objects of FIG. 120 at location B-B.

Figures 122, 123:
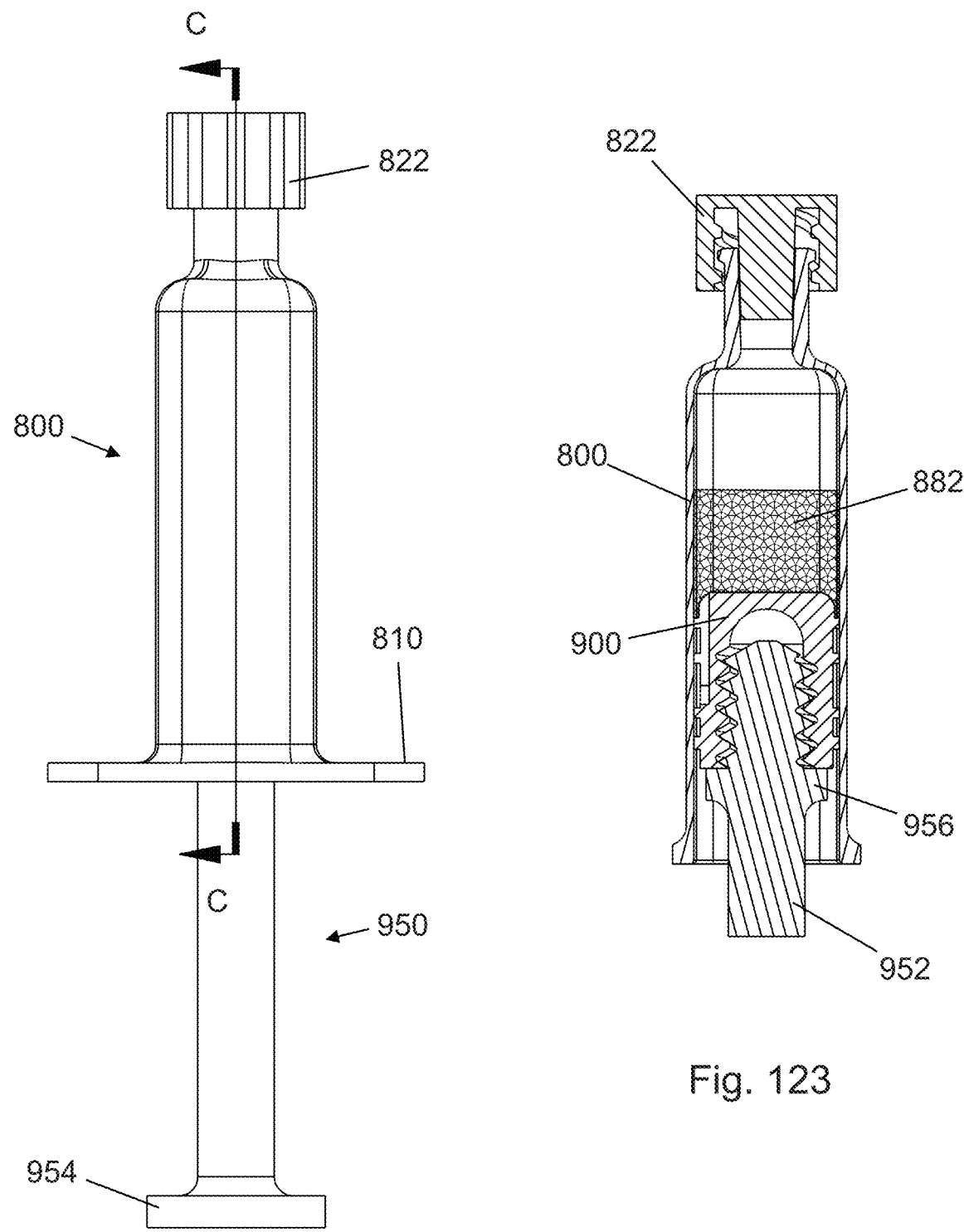

FIG. 122 is a side elevational view of the objects of FIG. 120 with the Luer cap removed, the syringe barrel inverted and the plunger advanced in preparation for rehydration of the lyophilized material.

FIG. 123 is a sectional view of the objects of FIG. 122 at location C-C.

Figure 124:
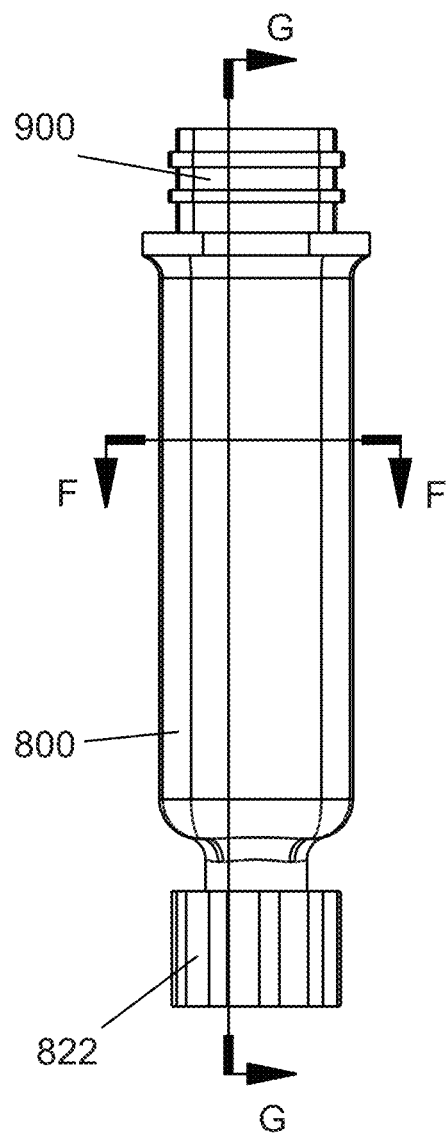

FIG. 124 is a side elevational view of the syringe barrel, Luer cap, and stopper in the "venting" position, in the vertical orientation.

Figure 125:
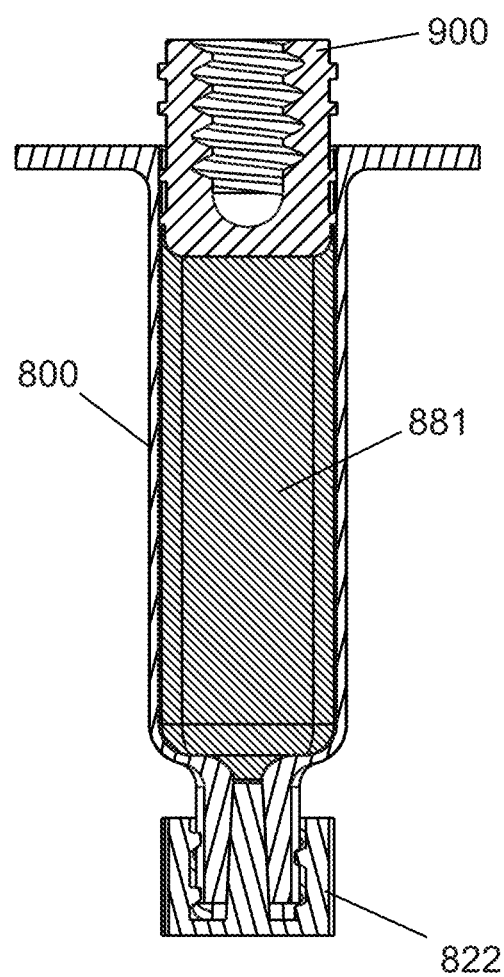

FIG. 125 is a sectional view of the objects of FIG. 124 at location G-G showing the surface area of liquid to be lyophilized when the elements are in the horizontal orientation as in FIG. 116.

Figure 126:
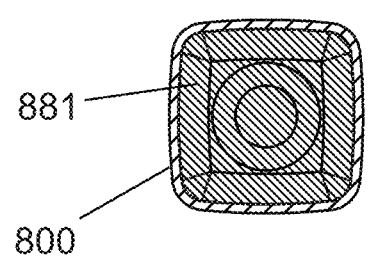

FIG. 126 is a sectional view of the objects of FIG. 124 at location F-F showing the surface area of liquid to be lyophilized when the elements are in the axial vertical position as in FIG. 115.

Figure 127:
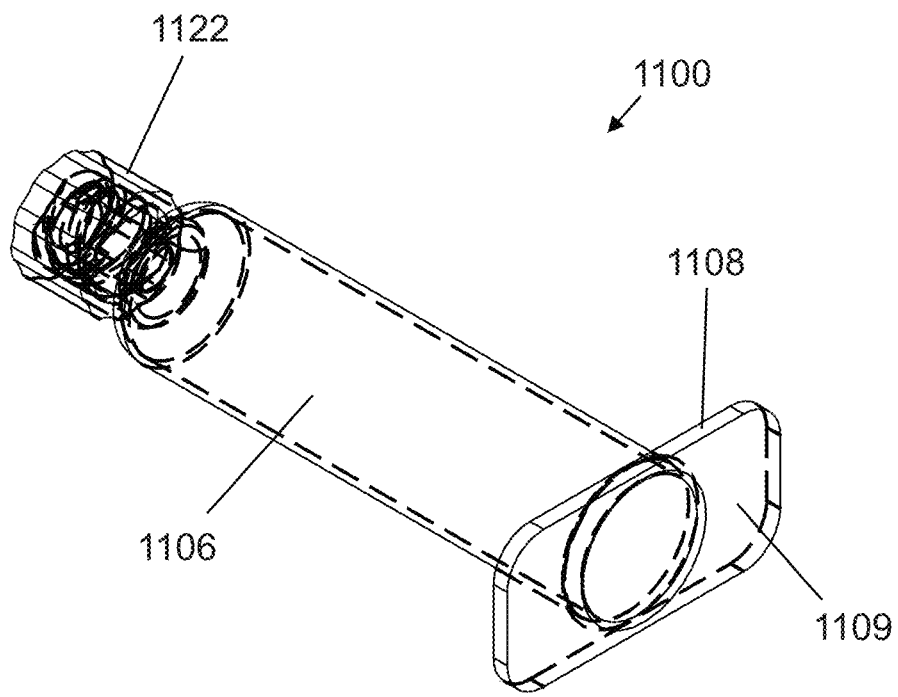

FIG. 127 is a perspective view of conventional syringe barrel characterized by a circular cross section (hereinafter referred to as a "rounded barrel" syringe).

Figure 128:
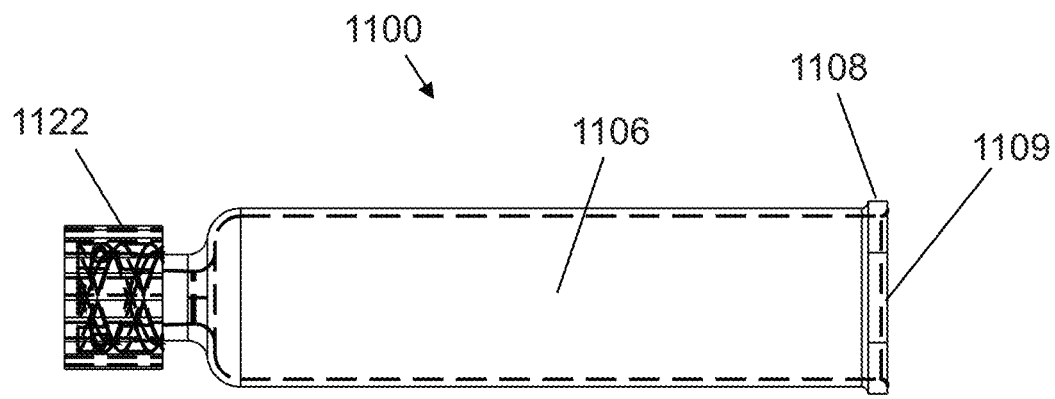

FIG. 128 is a side elevational view of the objects of the objects of FIG. 127.

Figure 129:
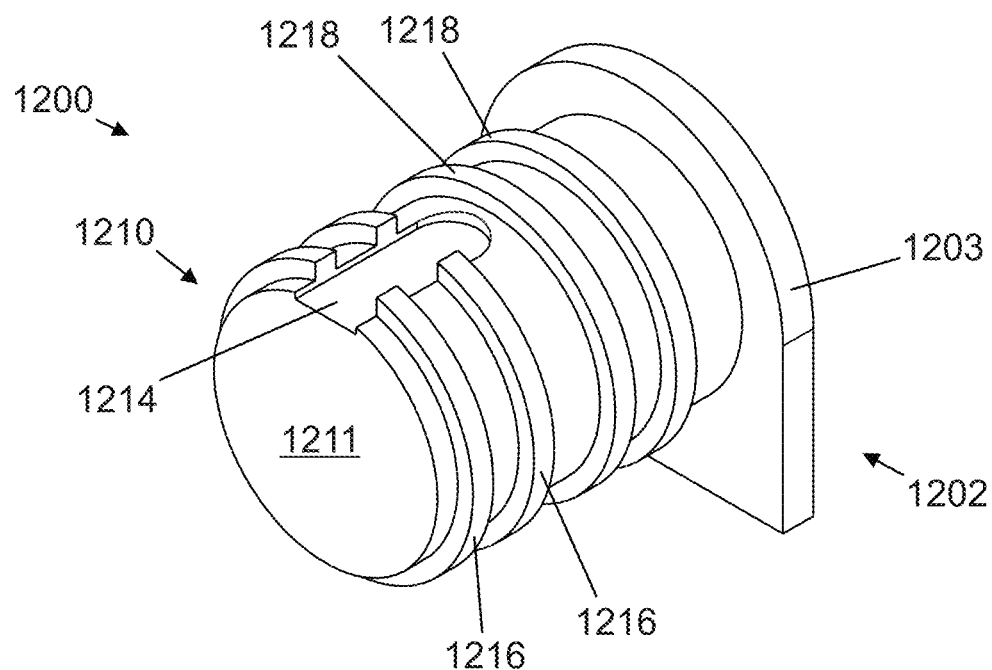

FIG. 129 is a distal perspective view of an alternate embodiment of a stopper of the present invention suitable for use with a conventional rounded barrel embodiment.

Figure 130:
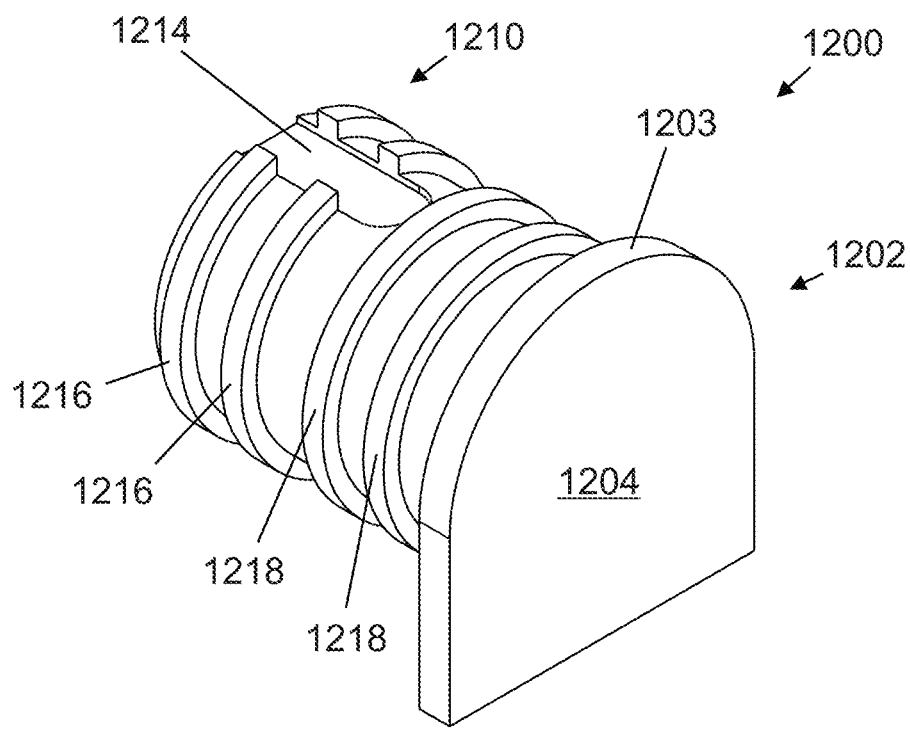

FIG. 130 is a proximal perspective view of the objects of FIG. 129.

Figure 131:
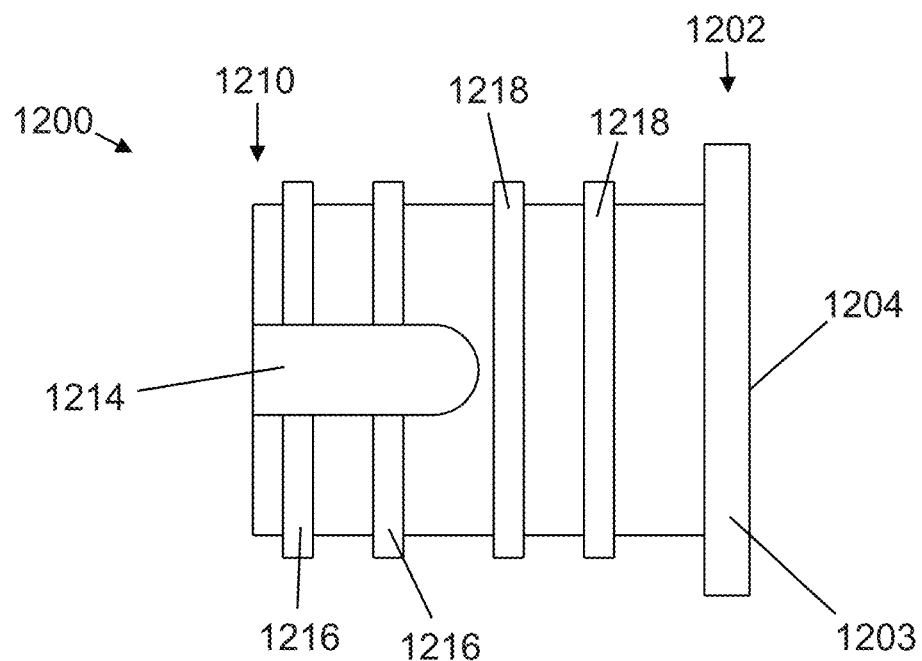

FIG. 131 is a plan view of the objects of FIG. 129.

Figure 132:
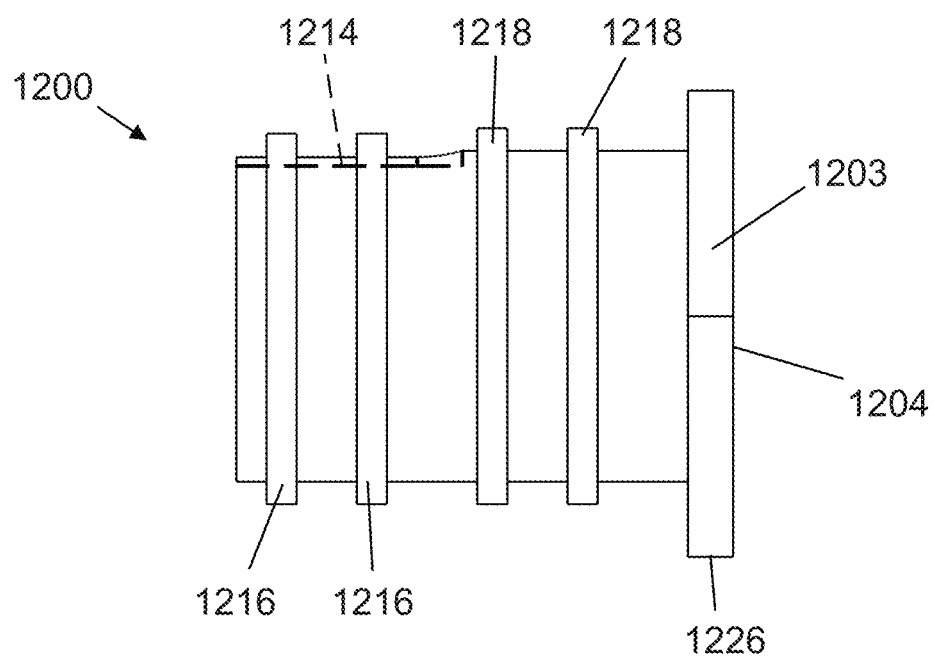

FIG. 132 is a side elevational view of the objects of FIG. 129.

Figure 133:
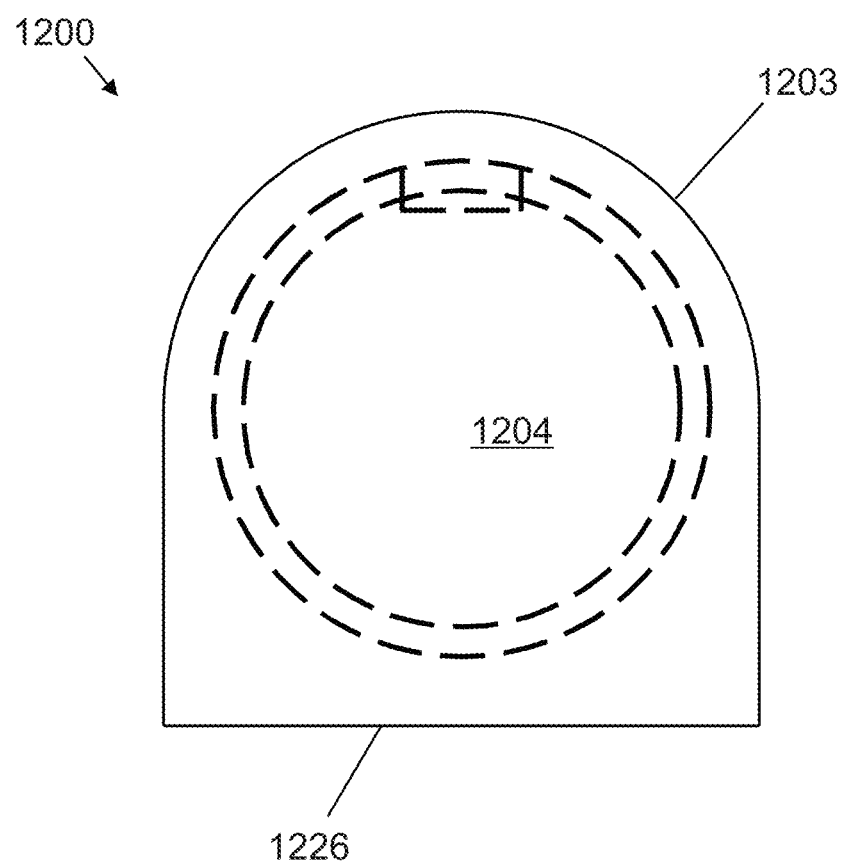

FIG. 133 is a proximal axial view of the objects of FIG. 129.

Figure 134:
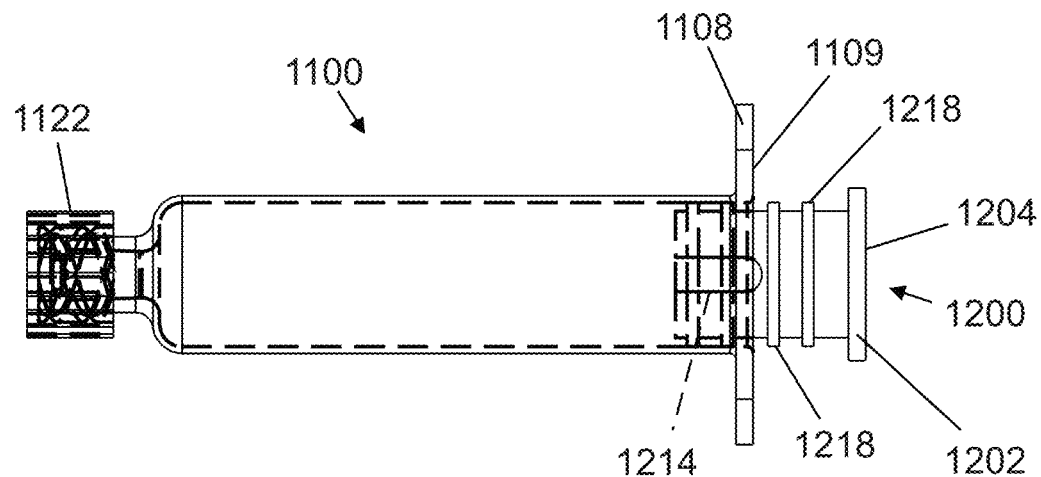

FIG. 134 is a plan view of the alternate stopper of FIG. 129 assembled to the conventional rounded barrel and Luer cap of FIG. 127 with the stopper in a first axial "venting" position.

Figure 135:
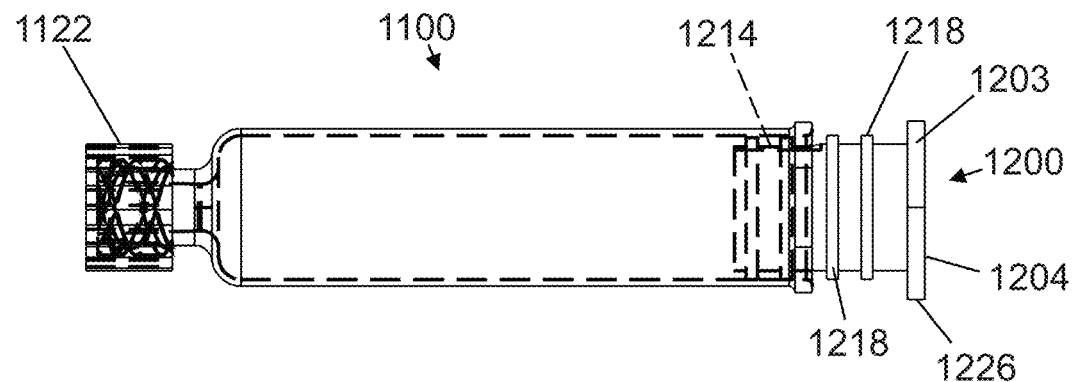

FIG. 135 is a side elevational view of the objects of FIG. 134.

Figure 136:
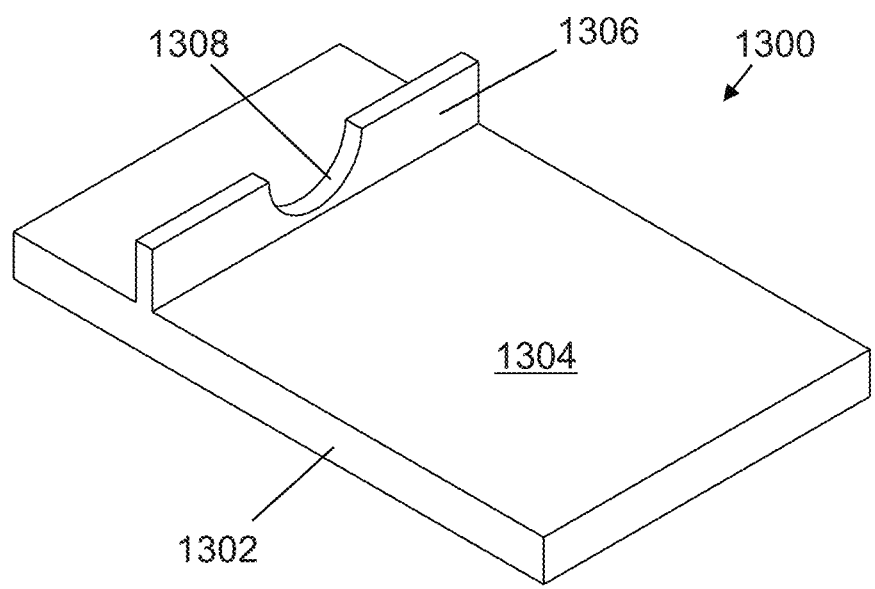

FIG. 136 is a perspective view of a mounting fixture configured for use in an alternate lyophilization method that utilizes the rounded barrel syringe assembly of FIG. 134.

Figure 137:
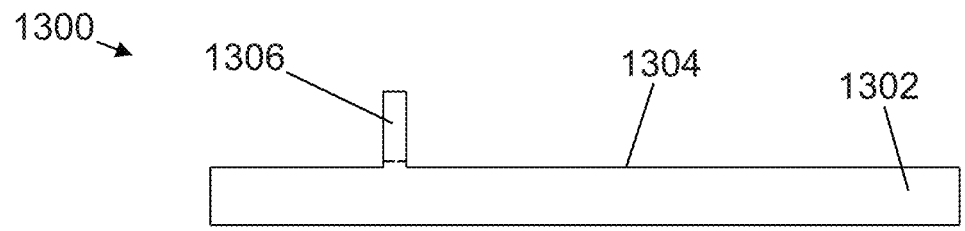

FIG. 137 is a side elevational view of the fixture of FIG. 136.

Figure 138:
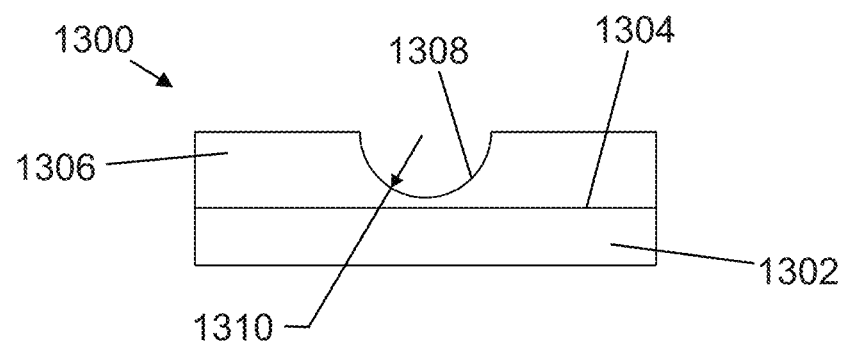

FIG. 138 is a proximal axial view of the fixture of 136.

Figure 139:
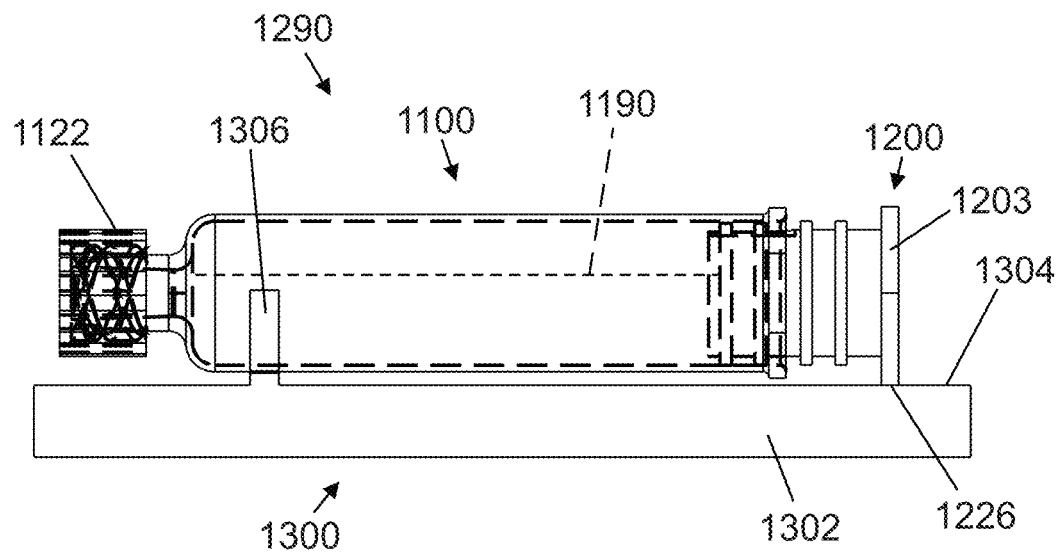

FIG. 139 is a side elevational view of the Luer cap, rounded syringe barrel and alternate embodiment stopper of FIG. 134 positioned on the fixture of FIG. 136 in preparation for lyophilization.

Figure 140:
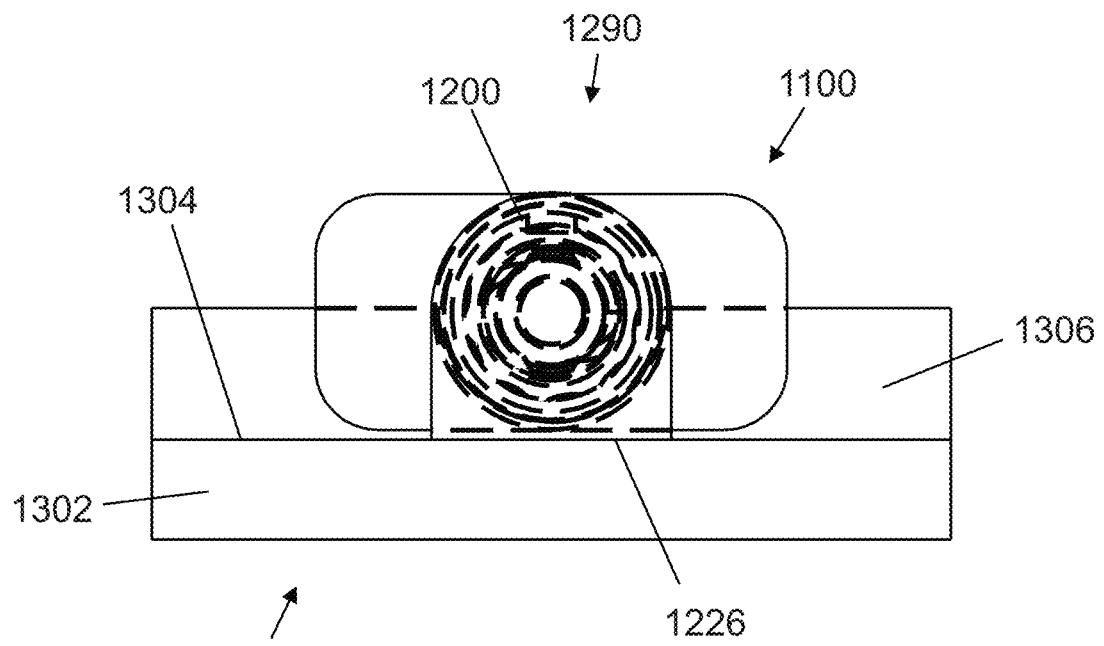

FIG. 140 is a proximal axial view of the objects of FIG. 139.

Figure 141:
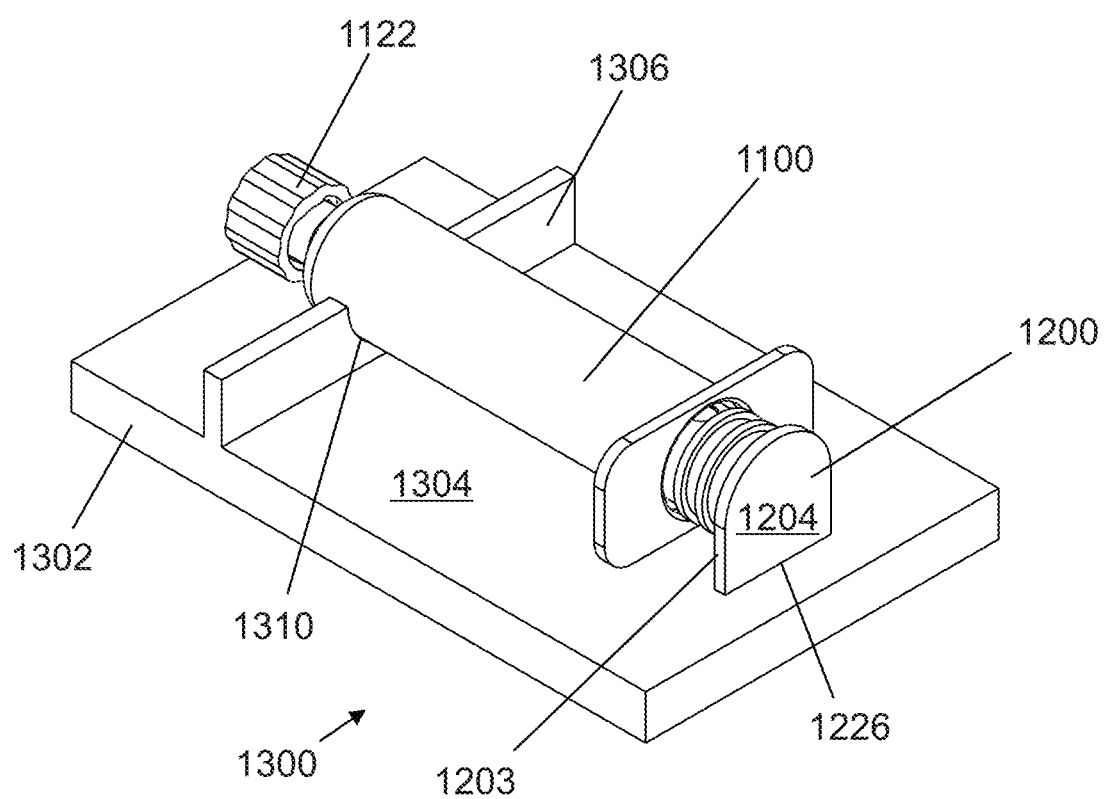

FIG. 141 is a perspective view of the objects of FIG. 139.

Figure 142:
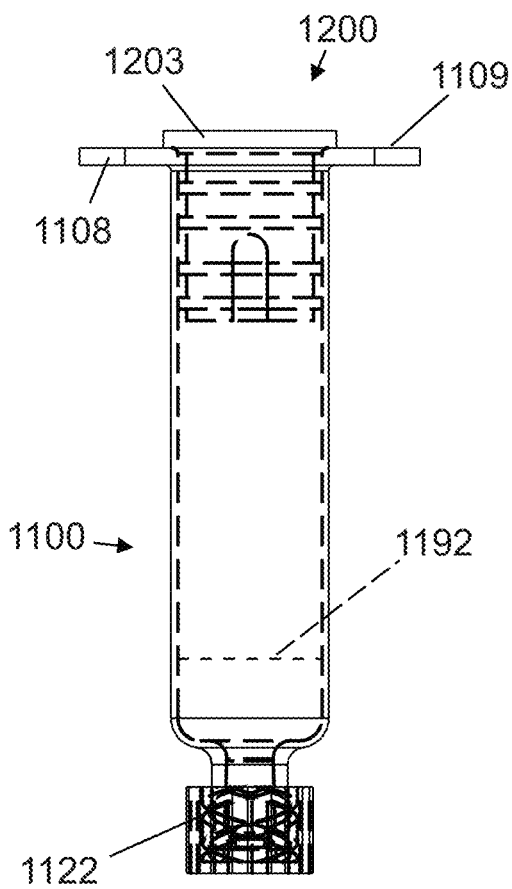

FIG. 142 is a side elevational view of the alternate embodiment syringe assembly of FIG. 139 at the completion of lyophilization, with the alternate stopper of FIG. 129 in the second axial "sealed" position.

Figure 143:
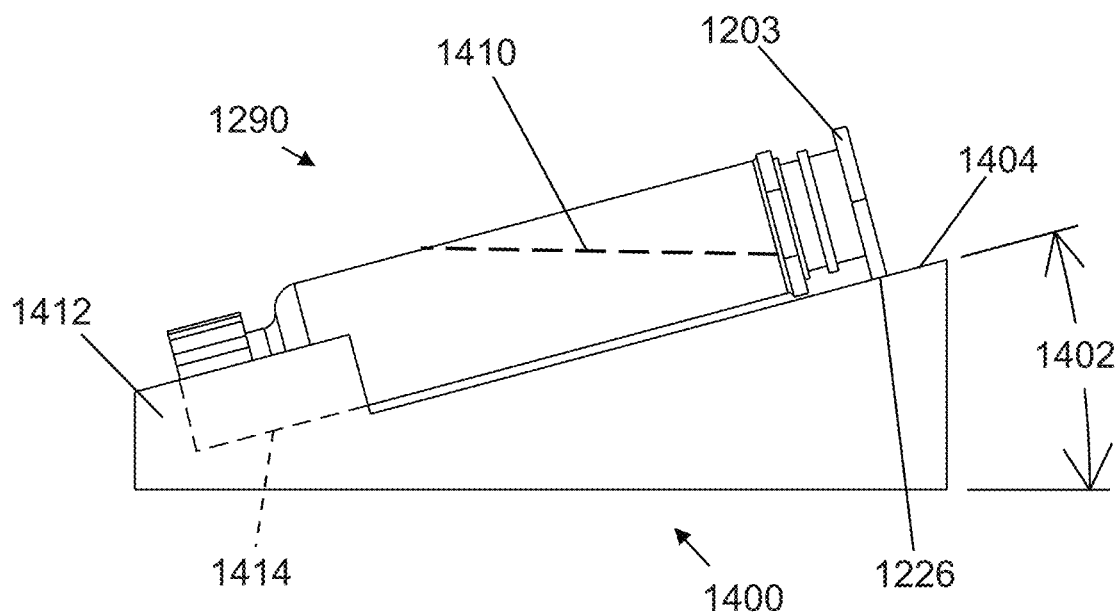

FIG. 143 is a side elevational view of the Luer cap, barrel and alternate stopper of FIG. 134 positioned in an alternate embodiment fixture that inclines the syringe assembly.

Figure 144:
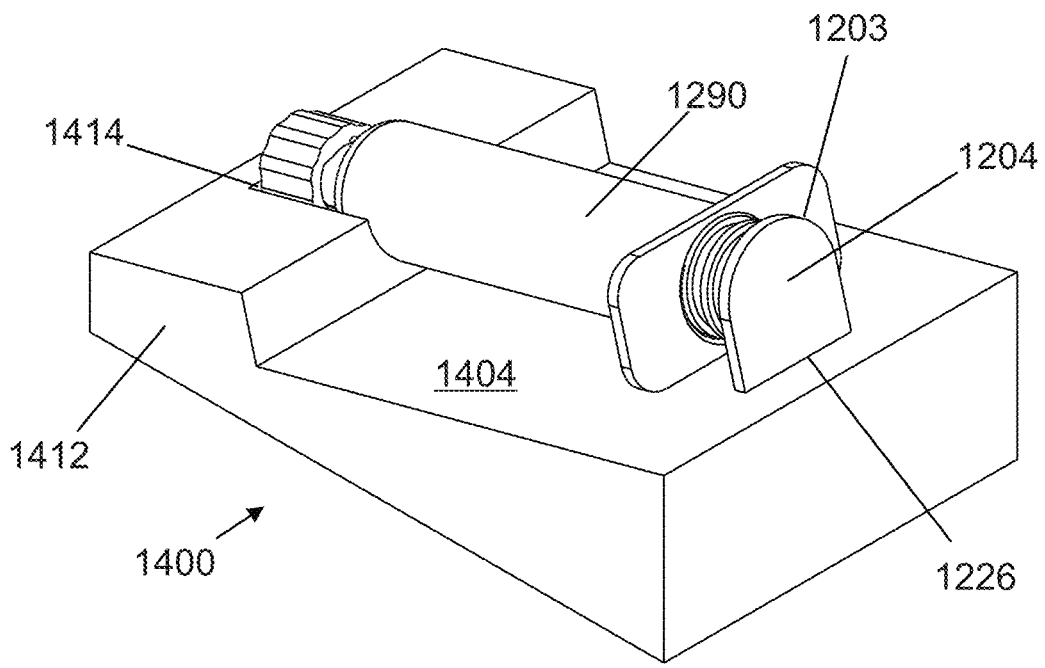

FIG. 144 is a perspective view of the objects of FIG. 142.

Figure 145:
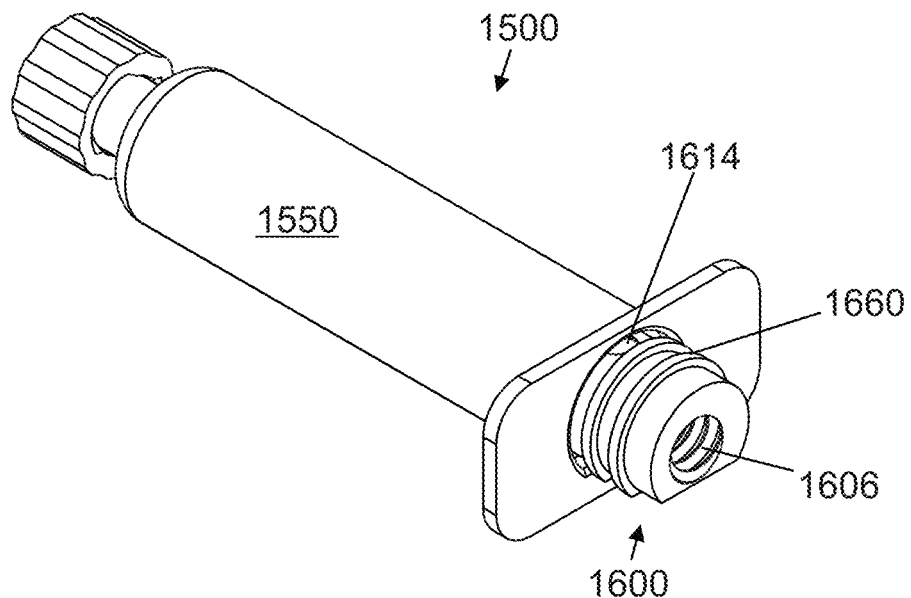

FIG. 145 is an upper proximal view of an alternate embodiment syringe assembly of the present invention characterized by a non-uniform cross section and depicting an alternate embodiment stopper in the first axial "venting" position.

Figure 146:
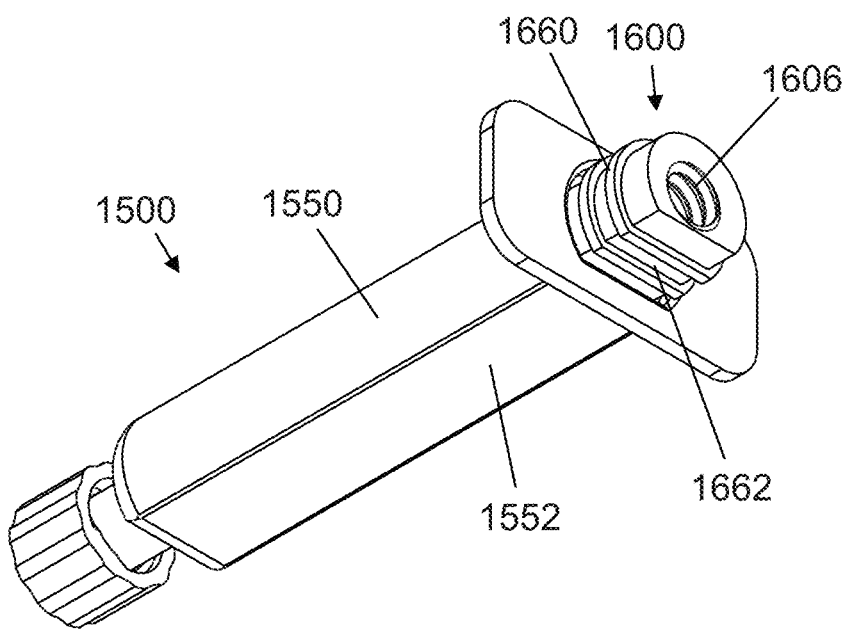

FIG. 146 is a lower proximal view of the objects of FIG. 145.

Figure 147:
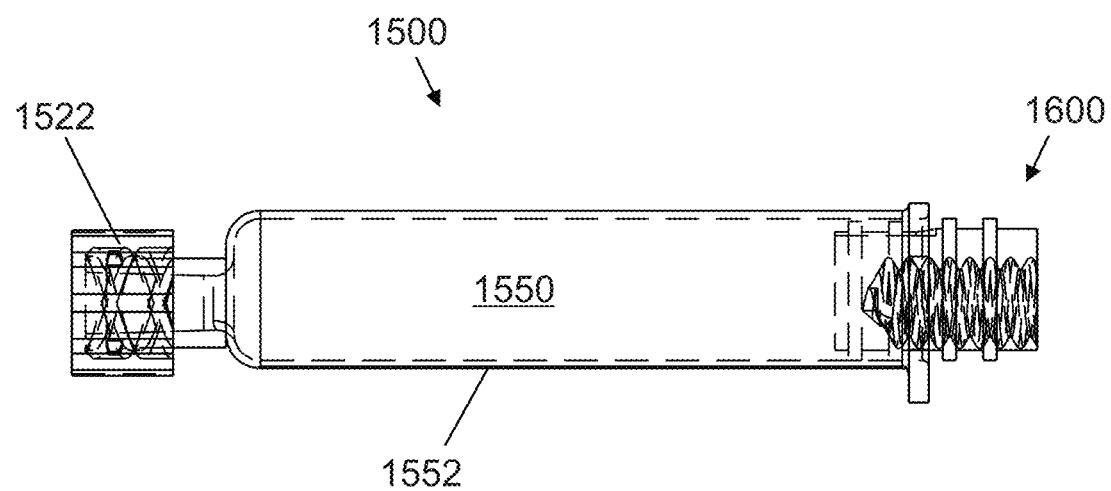

FIG. 147 is a side elevational view of the objects of FIG. 145.

Figure 148:
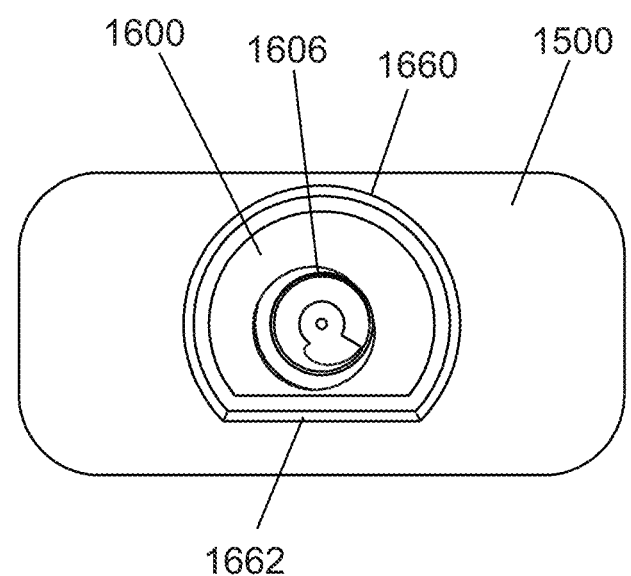

FIG. 148 is an expanded proximal axial view of the objects of FIG. 145.

Figure 149:
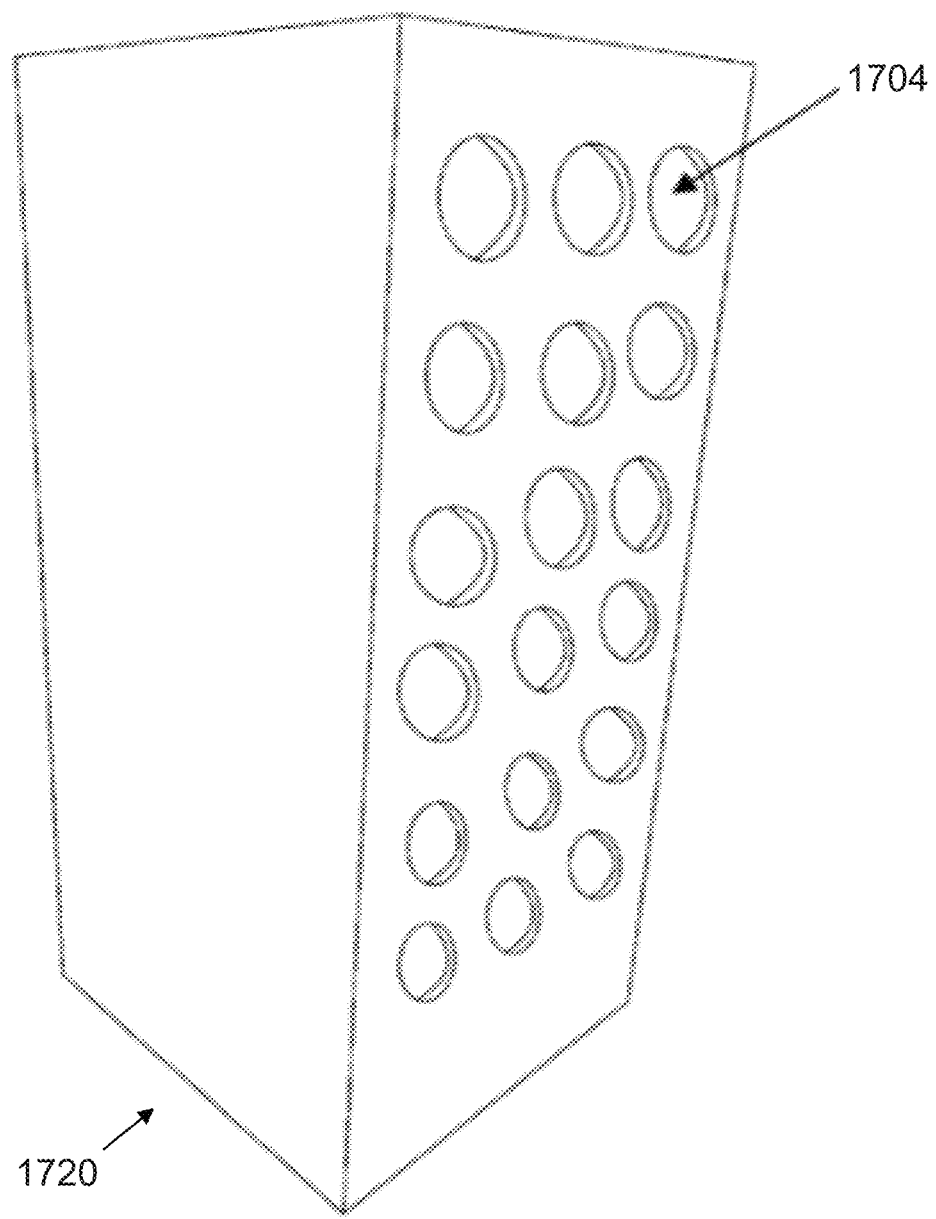

FIG. 149 is a side elevational view of an alternate embodiment of the thermal block of the present invention, wherein are formed multiple rounded wells for receiving syringe barrels of the present invention.

VI. DETAILED DESCRIPTION OF THE PREFERRED EMBODIMENTS

While various embodiments are henceforth described, the following description is intended to be exemplary, rather than limiting, and it will be apparent to those of ordinary skill in the art that many more embodiments and implementations are possible that are within the scope of the embodiments. Likewise, although many possible combinations of features are shown in the accompanying figures and discussed in this detailed description hereinbelow, many other combinations of the disclosed features are possible. As such, any feature or element of any embodiment may be used in combination with or substituted for any other feature or element in any other embodiment unless specifically restricted.

Although methods and materials similar or equivalent to those described herein can be used in the practice or testing of embodiments of the present invention, the preferred methods and materials are now described. However, it is to be understood that this invention is not limited to the particular sizes, shapes, dimensions, materials, methodologies, protocols, etc. described herein, as these may vary in accordance with routine experimentation and optimization. It is also to be understood that the terminology used in the description is for the purpose of describing the particular versions or embodiments only, and is not intended to limit the scope of the present invention which will be limited only by the appended claims. Accordingly, unless otherwise defined, all technical and scientific terms used herein have the same meaning as commonly understood by one of ordinary skill in the art to which the present invention belongs. However, in case of conflict, the present specification, including definitions below, will control. Thus, in the context of the present invention:

The words "a", "an", and "the" as used herein mean "at least one" unless otherwise specifically indicated. Thus, for example, reference to an "opening" is a reference to one or more openings and equivalents thereof known to those skilled in the art, and so forth.

The term "proximal" as used herein refers to that end or portion of a device that is situated closest to the user of the device, farthest away from the active or operative end of a device. In the context of the present invention, the proximal end of a syringe of the present invention includes the sealing cap, plunger and finger grip portions.

The term "distal" as used herein refers to that end or portion of a device that is situated farthest away from the user of the device, closest to the operative end. In the context of the present invention, the distal end of a syringe of the present invention refers to the output end adapted to receive a needle and/or stopper element.

The terms "lengthwise" and "axial" are used interchangeably herein to refer to the direction relating to or parallel with the longitudinal axis of a device. The term "transverse" as used herein refers to the direction lying or extending across or perpendicular to the longitudinal axis of a device.

The present invention makes reference to "horizontal" and "vertical" orientations. In the context of the present invention, a horizontal orientation is characterized by a longitudinal axis running parallel to the conventional "X"-axis whereas a vertical orientation is characterized by a longitudinal axis running parallel to the conventional "Y" axis.

The term "lateral" pertains to the side and as used herein, refers to motion, movement, or materials that are situated at, proceeding from, or directed to a side of a device.

The term "medial" pertains to the middle, and as used herein, refers to motion, movement or materials that are situated in the middle, in particular situated near the median plane or the midline of the device or subset component thereof.

The terms "tube" and "tubular" are interchangeably used herein to refer to a generally round, long, hollow component having at least one central opening often referred to as a "lumen".

The present invention refers interchangeably to "containers" and "product containers" designed to carry an initial product to be lyophilized (generally in liquid form), withstand the temperatures and pressures associated with lyophilization, and store the subsequent lyophilized product until called for use. In the context of the present invention, such containers are preferably fabricated from a deformable polymeric material, such as polypropylene. More particularly, such as in the exemplary embodiments identified above and described in detail below, the product container is preferably the barrel of a syringe. However, it will be readily understood that the container need not be a syringe barrel but rather may take the form of a vial, bottle, ampoule, syringe, tube, or other suitable vessel or receptacle.

In the context of the present invention, the terms "syringe", "syringe body", and "syringe barrel" are used interchangeably to refer to a specialized lyophilized product container, namely dispensing device comprised of a central hollow bore having a distal tip configured to receive a hypodermic needle assembly and an open, often flanged proximal end configured to receive a dispensing plunger/piston. In preferred embodiment, the outside of the barrel is provided with graduated markings indicating the volume of fluid in the syringe. In particularly preferred embodiments, the syringe barrel has a non-uniform and/or non-cylindrical cross section. See, for example, the substantially square embodiment of FIG. 79 ("800") and the arched or D-shaped embodiment of FIG. 145 ("1500"). As discussed in greater detail hereinbelow, such shapes, particularly those that include at least one relatively planar lateral wall, enable the user to determine and designate a top surface and ensure that the designated top surface is always in proper alignment. More particularly, in contrast to conventional "round barreled" syringes of the prior art, syringe barrels shaped in accordance with the present invention will not "roll" on a flat surface but rather will remain immobile. In the context of the present invention, a syringe barrel is characterized by an open proximal end, an open distal tip, and a hollow bore extending therebetween. As noted below, the open distal tip is preferably tapered or threaded to receive a hypodermic needle assembly. However, when not in use, the open distal tip is preferably sealed by means of a locking cap, for example, a Luer cap.

In a similar fashion, the open proximal end is preferably sealed by means of a stopper, typically fabricated from a flexible rubber, plastic or elastomeric material suitable for creating a tight seal with the inner walls of the syringe barrel. To that end, the stopper may be provided with one or more circumferential sealing ribs configured to match the contours formed by the inner surfaces of the walls of the barrel, albeit preferably expanded slightly so as to form a seal with the contours formed by surfaces.

In conventional embodiments of the prior art, the primary function of such a stopper is to prevent air and liquid from leaking out of the syringe barrel during the injection or withdrawal process. However, in the context of the present invention, the stopper can serve multiple functions, namely (1) as a sealing element to prevent product leakage when the syringe is placed in a horizontal orientation; (2) as a venting element to allow for gaseous outflow from the hollow bore when undergoing lyophilization; and finally (3) as a piston element when coupled with a plunger stem. Thus, depending upon the functionality of interest, this stopper is at times referred to herein and elsewhere as a "sealing member" or "sealing cap", "venting member" or "venting cap", "piston member" or "sealing piston". In the context of the present invention, the stopper includes at least one vent channel disposed along a lateral surface of the stopper that, when exposed to atmosphere, serves as an escape route for gas that may build up within the syringe barrel, such as arises during lyophilization. While the length, width, depth, and overall shape of the channel may be readily varied, functionality demands that it extend from a distal side of the stopper (so as to be in fluidic and gaseous communication with the contents of the hollow central bore of the syringe) but stop short of the stopper proximal end.

In the context of the present invention, the stopper has two distinct arrangements, namely, a first axial placement referred to herein as the "venting" position and a second axial placement referred to herein as the "sealed" position. To wit, in the first "venting" position, the stopper is partially inserted into the syringe barrel via the open proximal end to a first axial position in which the proximal end of the vent channel is exposed to atmosphere and thereby forms an escape path for outgassing such as arises during lyophilization processes. In the second "sealed" position, the stopper is more distally and/or fully inserted into the central hollow bore of the syringe barrel to a second axial position in which the proximal end of the vent channel is distal to the proximal end of the syringe barrel and the more proximal portion of the stopper (e.g., one or more of the circumferentially arrayed ribs) engages the inner walls of the barrel to form a gas and fluid tight seal that guards against contamination and leakage of the syringe barrel contents.

As noted above, the stopper further functions as a piston element when coupled with a plunger stem. Accordingly, in the context of the present invention, the proximal end of the stopper is preferably provided with threaded socket configured to receive the corresponding threaded end of a plunger stem; the threaded socket may also serve a coupling mechanism for an insertion tool designed to ensure proper placement of the stopper within the syringe barrel. Thus, in accordance with the methods of the present invention, an individual syringe may be used to both lyophilize a liquid preparation into a dried/lyophilized product and subsequently rehydrate and dispense the dried product in rehydrated form. In this manner, a single syringe can be used to lyophilize, store, ship, and dispense a medicament of interest to a patient. Critically, due to the vacuum seal generated by the stopper after lyophilization, all steps regarding storage, transportation, and patient dispensing may be accomplished in the absence of expensive refrigeration. Likewise, by eliminating the need to transfer lyophilized product to another container prior to administration, the methods of the present invention ensure sterility and protect against contamination.

The distal tip or "needle hub" of a syringe barrel finding utility in the context of the present invention is preferably threaded or tapered so as enable firm connection to a hypodermic needle assembly. Perhaps the most well-known of these is the "Luer taper" or "Luer lock", which simply twists the two together. Alternatively, the needle hub may take the form of a "slip tip", a small, friction-fit connection useful when the syringe is being connected to something not featuring a screw lock mechanism Similar to this is the "catheter tip", which is essentially a slip tip but longer and tapered, making it good for pushing into things whereby the plastic taper can form a tight seal.

Lyophilization methods of the present invention offer decreased cycle times, a contributing factor being improved heat transfer to and from the product. One element of this method is a thermal block formed of a suitable metallic material. Accordingly, the present invention refers interchangeably to a "block", "thermal block", and "heat block" fabricated from a heat conductive material and having a plurality of identical wells orderly arrayed about its top surface, wherein each of said wells is configured to receive a container carrying product to be lyophilized. In a preferred embodiment, the block is aluminum, chosen for its light weight and excellent thermal conductive properties.

Wells formed in the top surface of the block are designed and dimensioned to receive suitable containers of product to be lyophilized, such as a vial or a syringe barrel. In the context of the present invention, the wells are sized and shaped to closely accommodate the particular container of choice. For example, in the exemplary embodiments described in detail below, the containers take the form of syringe barrels having a substantially square cross-section, wherein sides are optionally bowed outward to form convex outer surfaces. The associated wells are analogously shaped and configured to cause deformation of the syringe barrel in a manner that causes the outer walls of the barrel to be compressed against the inner walls of the well so as to create close contact and optimal conditions for heat conduction. However, one of skill in the art will recognize that the principles taught herein are applicable to syringe barrel shapes other than substantially square. For instance, the shape may be rectangular, a regular or irregular polygon, oval or oblong, circular, or may have an irregular curvilinear profile. So long as the shape allows deformation when inserted into a suitably configured well so as to create substantial intimate contact between surfaces of the barrel and of the well, it falls within the scope of this invention.

In a method of the present invention exemplified below, a plurality of resilient polymeric syringe barrels, each of which having a substantially square cross-section, are singularly introduced into a corresponding plurality of wells evenly arrayed about the top surface of a metallic thermal block, wherein the wells are dimensioned in such a way as to cause deformation of the syringe barrel and thereby create intimate contact between outer surfaces of the syringe barrel and well sidewalls. Again, one of skill in the art will recognize that the criticality lies less with the precise shape of the respective containers and wells than with the close contact generated by their connection. Thus, regardless of shape, any lyophilization method in which a polymeric syringe barrel with a first cross-sectional shape is inserted into a well in a metallic block or plate with the well having a second different shape that serves to create surface contact that enhances thermal conductivity therethrough falls within the scope of this invention.

In certain embodiments exemplified below, the product container is the barrel of a syringe. It will be understood that the container need not be a syringe but may be a vial or any other suitable container formed of a suitable resilient polymeric material such that, when the container is inserted into the thermal block, the walls of the container deform so as to create intimate contact between outer surfaces of the container and the well into which it is inserted. Any such product container falls within the scope of the present invention. That being said, certain advantages and benefits of the present invention accrue when a single use syringe is used to lyophilize, store, transport, and dispense a product of interest.

As discussed in greater detail in the examples below, the lyophilization methods of the present invention involve the step of orienting the syringe barrel in either the "horizontal" and "vertical" orientation. Namely, in the context of the present invention, the liquid product to be lyophilized is preferably introduced into the interior bore of the syringe with the barrel in the vertical or upright orientation (i.e., with the distal tip pointing down and the open proximal end facing up so as facilitate material transfer. The stopper is then inserted into the syringe barrel to the first axial position (i.e., the venting position in which the proximal end of the vent channel is exposed) and rotated 90 degrees to the horizontal orientation. As discussed in U.S. Pat. Nos. 11,536,512 and 11,723,870, the contents of which are incorporated by reference herein, in the context of lyophilization, the relative contributions of heat conduction and surface area increase are strongly affected by the syringe configuration. In particular, rates are increased by orienting the syringe barrel axis horizontal during processing for increased free surface area. To that end, the present invention further lyophilization methods in which the drying rate is increased solely by the increased free surface area of the material being processed, this area of increase being achieved by orienting the vial or syringe with the axis horizontal or at a predetermined angle to horizontal.

So as to guard against leakage, the venting channel is orientated to face up. In a preferred embodiment, the vent channel is positioned opposite a relatively planar surface of a syringe barrel having a non-uniform and/or non-circular cross section such that when such a syringe barrel is placed on its relatively planar side, the vent channel either is or is arranged to be visible on the opposite side. As noted above, once lyophilization is complete, the stopper is slid to the second sealed position, after which the syringe may rotated and manipulated at will without disturbing the lyophilized material contained therein.

In the context of the present invention, the terms "subject" and "patient" are used interchangeably herein to refer to any animal (e.g., a mammal), including, but not limited to, humans, non-human primates, canines, felines, rodents, and the like, which is to be the recipient of a particular treatment. In preferred embodiments, the subject is a human, more preferably a patient in need of subcutaneous, intravenous and/or intramuscular pharmaceutical therapy.

Hereinafter, the present invention is described in more detail by reference to the FIGS. and Examples. However, the following materials, methods, figures, and examples only illustrate aspects of the invention and are in no way intended to limit the scope of the present invention. As such, methods and materials similar or equivalent to those described herein can be used in the practice or testing of the present invention.

EXAMPLES

Figure 1:
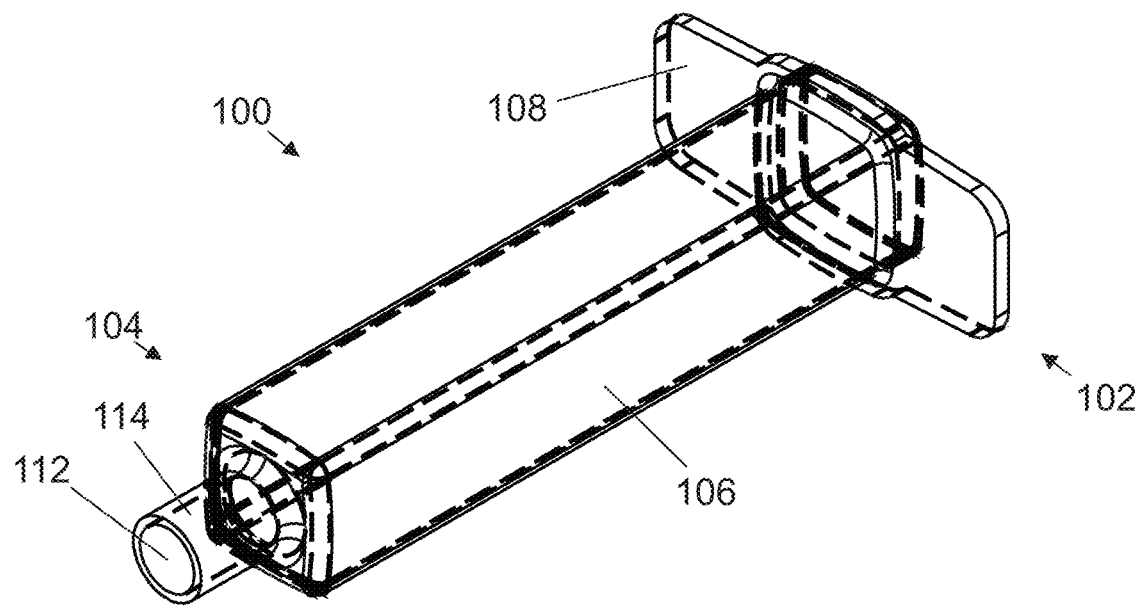
FIG. 1 is a distal perspective view of a syringe barrel formed in accordance with the principles of the present invention.
Figure 2:
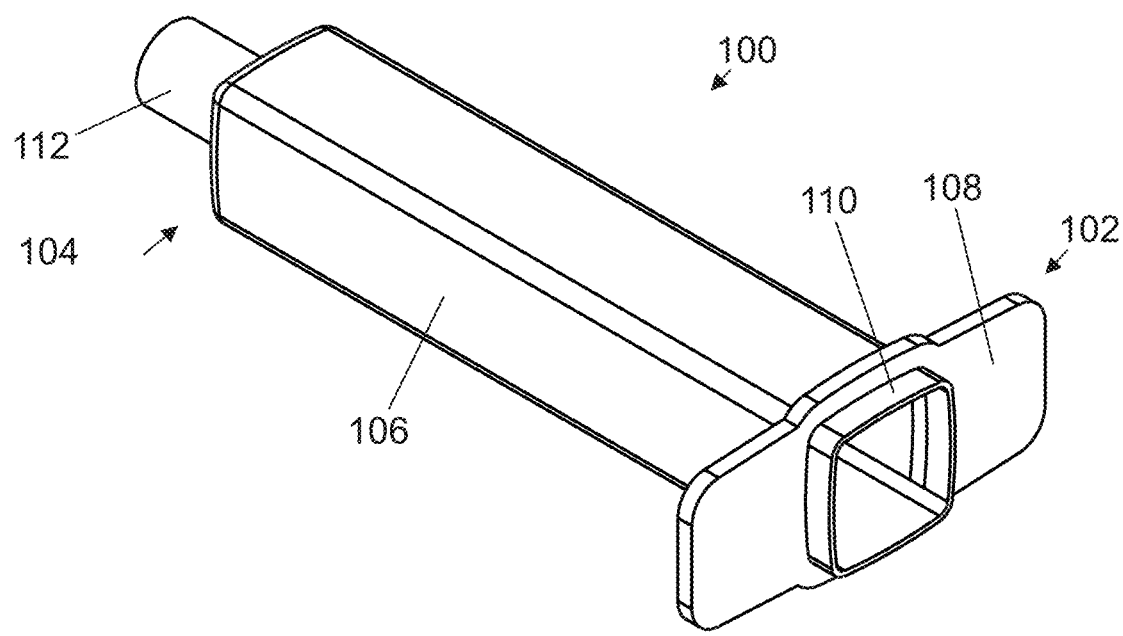
FIG. 2 is a proximal perspective view of the objects of FIG. 1.
Figure 3:
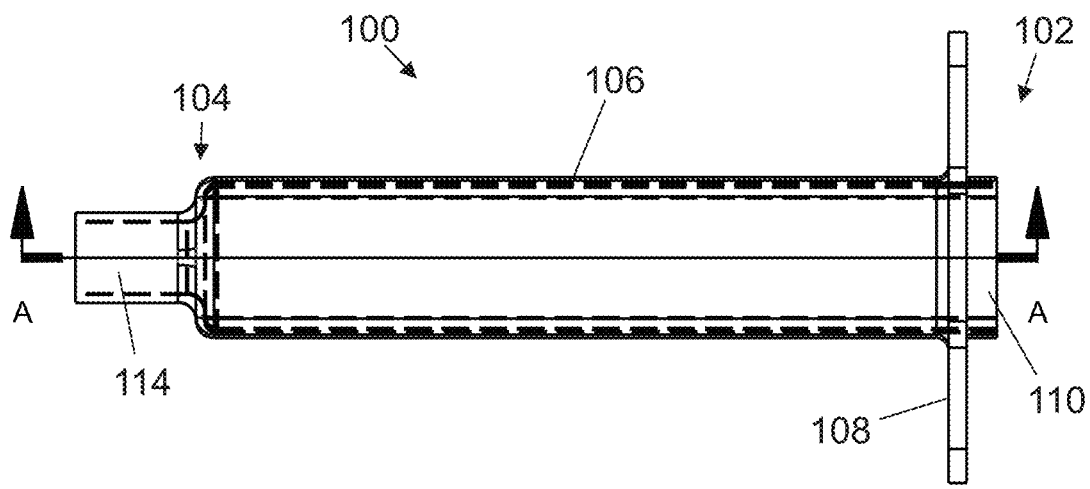
FIG. 3 is a plan view of the objects of FIG. 1.
Figure 4:
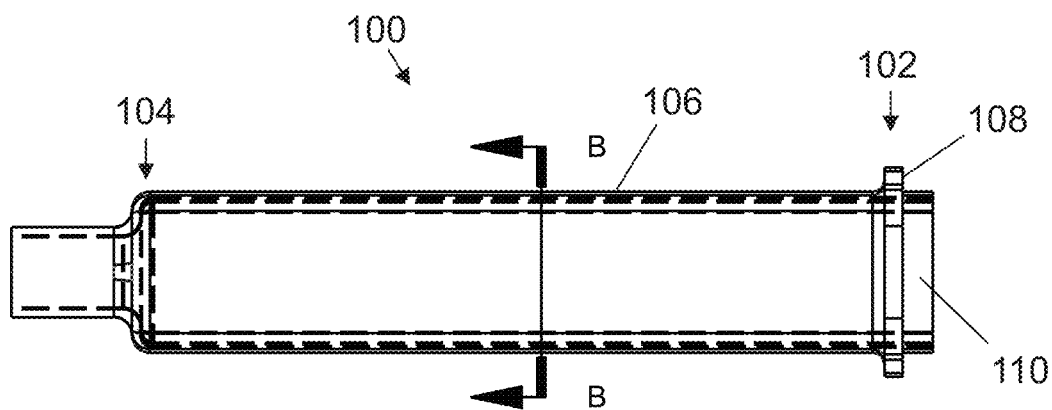
FIG. 4 is a side elevational view of the objects of FIG. 1.
Figure 5:
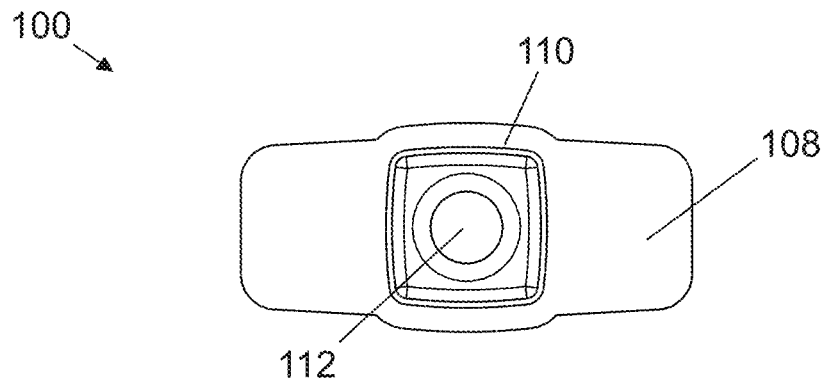
FIG. 5 is a proximal end view of the objects of FIG. 1.
Figure 6:
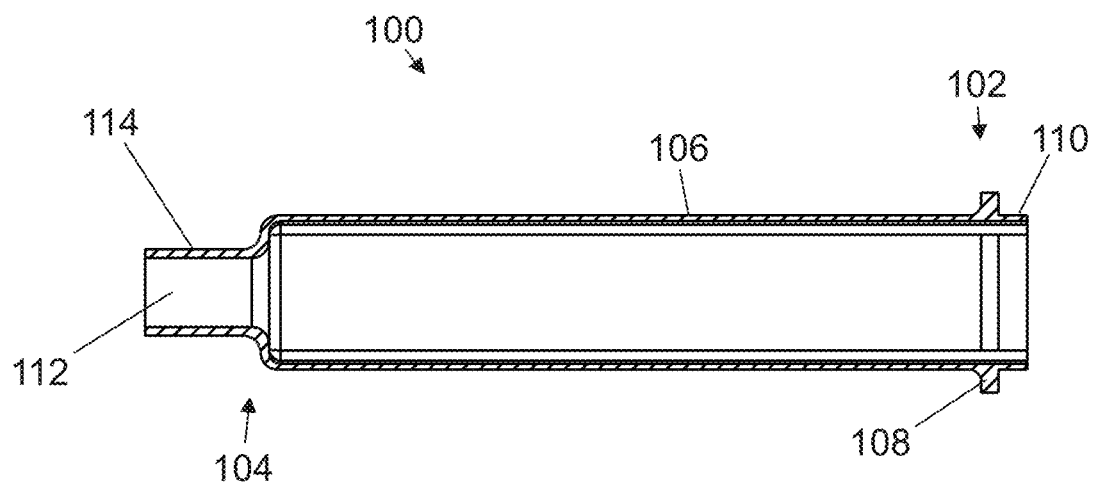
FIG. 6 is a sectional view of the objects of FIG. 3 at location A-A.
Figure 7:
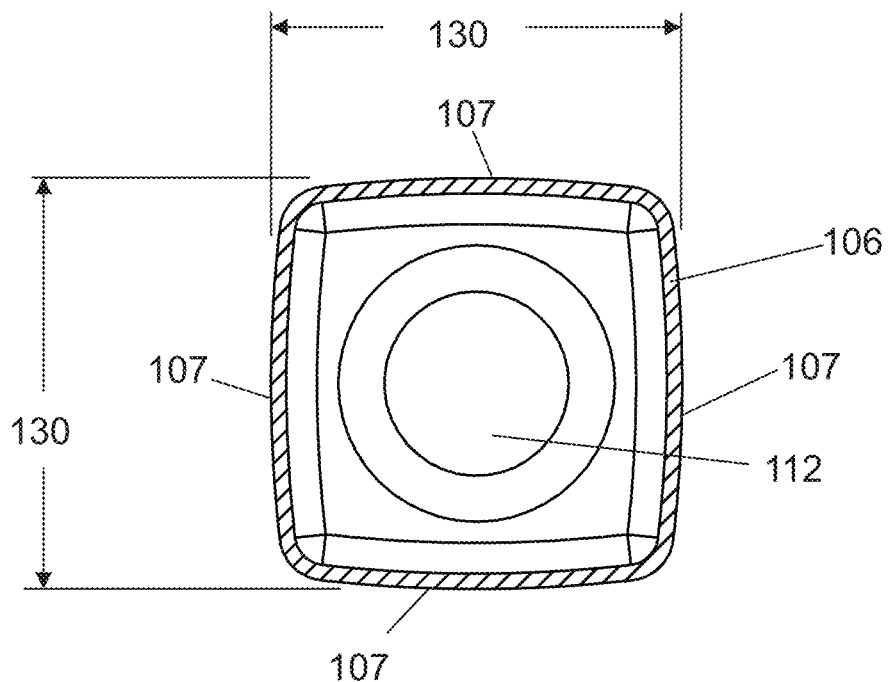
FIG. 7 is an expanded sectional view of the objects of FIG. 4 at location B-B.
Figure 8:
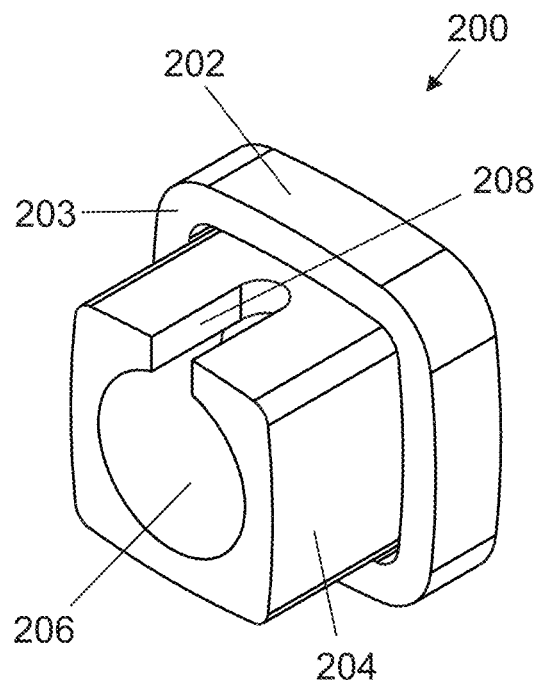
FIG. 8 is a perspective view of a stopper mounted to the proximal end of a syringe barrel formed in accordance with the principles of the present invention.
Figure 9:
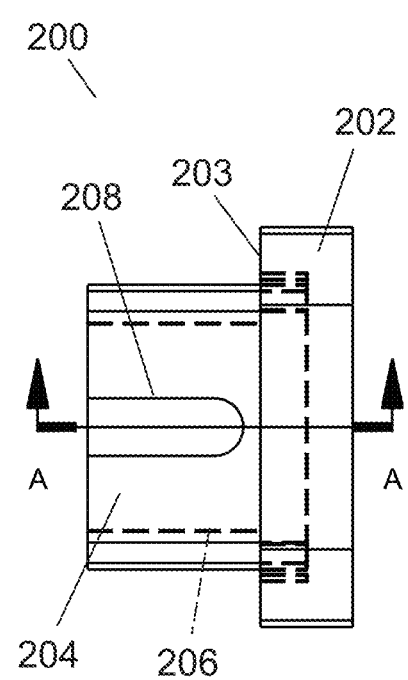
FIG. 9 is a plan view of the objects of FIG. 8.
Figure 10:
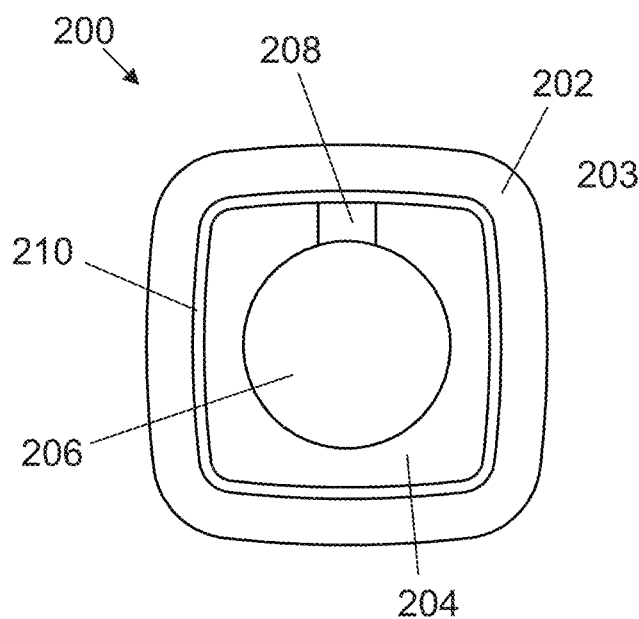
FIG. 10 is a distal axial view of the objects of FIG. 8.
Figure 11:
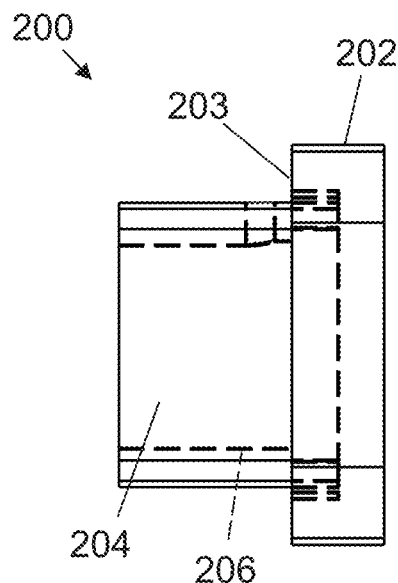
FIG. 11 is a side elevational view of the objects of FIG. 8.
Figure 12:
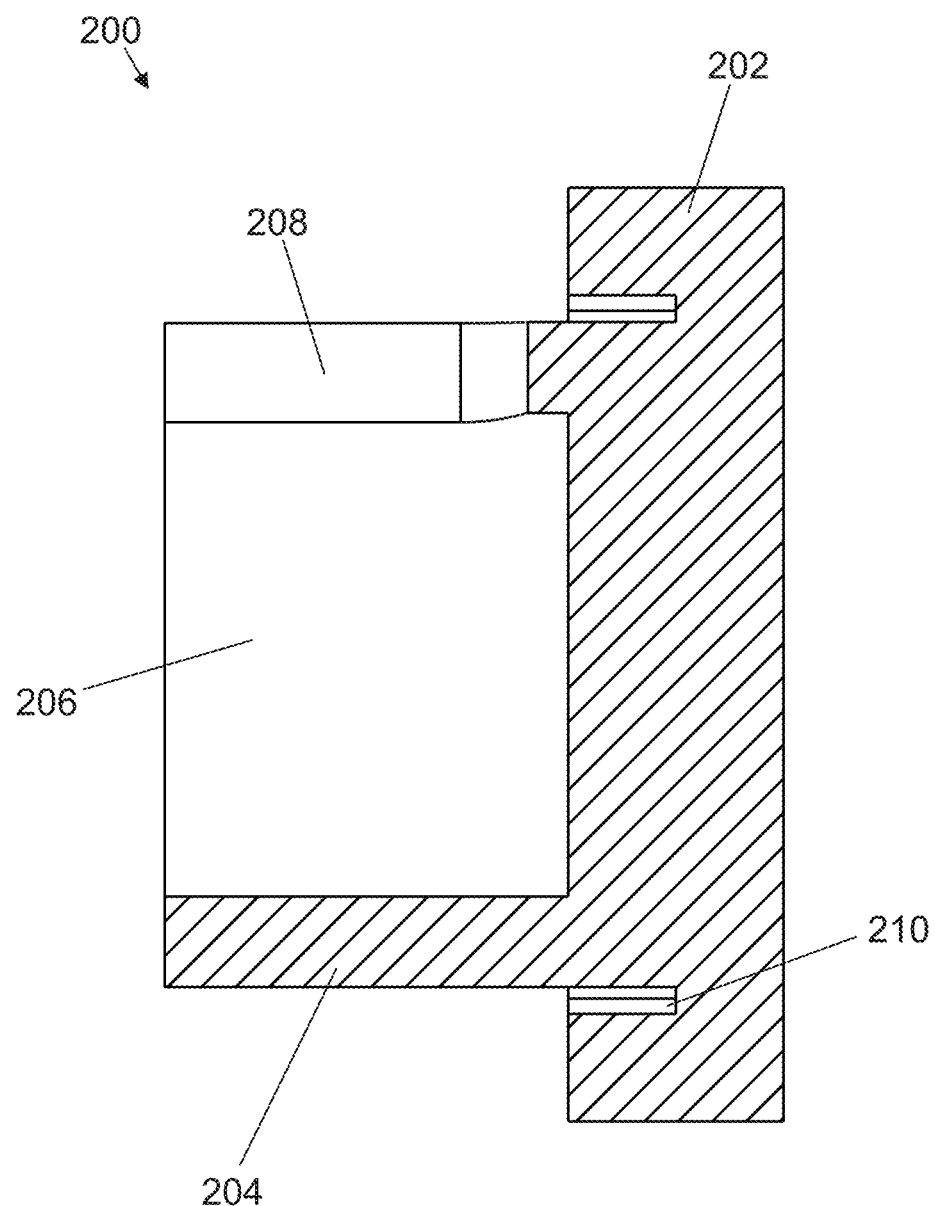
FIG. 12 is an expanded sectional view of the objects of FIG. 9 at location A-A.

A syringe barrel 100 of the present invention is depicted in FIGS. 1 through 7. Barrel 100 has an elongate mid-portion 106 with barrel flange 108 formed at its proximal end, and distal output portion 112 at its distal end. In preferred embodiments, output portion 112 is a Luer lock or Luer taper. Rim 110 extends proximally from the proximal surface of barrel flange 108. As best seen in FIG. 7, the walls of barrel mid-portion 106 with outer surfaces 107 are not planar, but rather have a predetermined convex shape. Syringe barrel 100 is formed of a resiliently deformable polymeric material. In preferred embodiments, the material is polypropylene.

A stopper 200 for removable mounting to the proximal end of syringe barrel 100 is depicted in FIGS. 8 through 12. Stopper 200 has a proximal portion 202 and a distal portion 204 wherein is formed distal recess 206 and slot 208. Circumferential groove 210 is formed in the distal surface of proximal portion 202, groove 210 being configured to accept therein rim 110 of syringe barrel 100.

Figure 13:
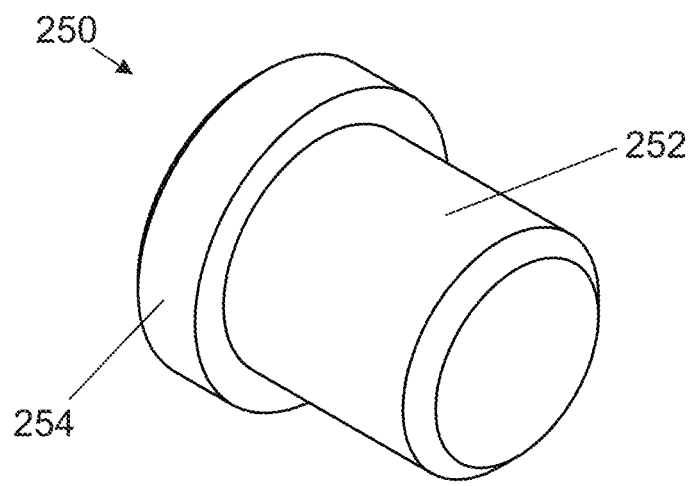
FIG. 13 is a perspective view of a cap mounted to the distal end of a syringe barrel of the present invention.
Figure 14:
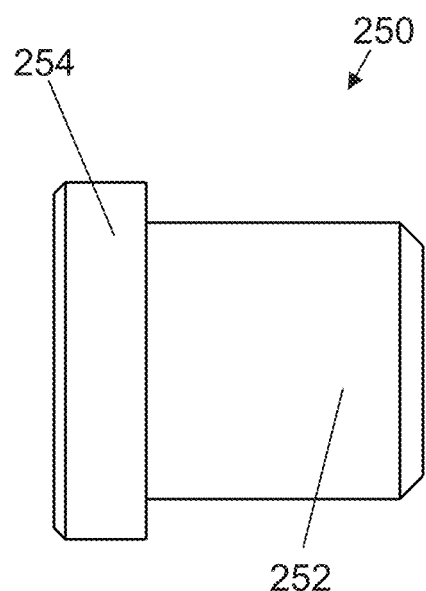
FIG. 14 is a side elevational view of the objects of FIG. 13.
Figure 15:
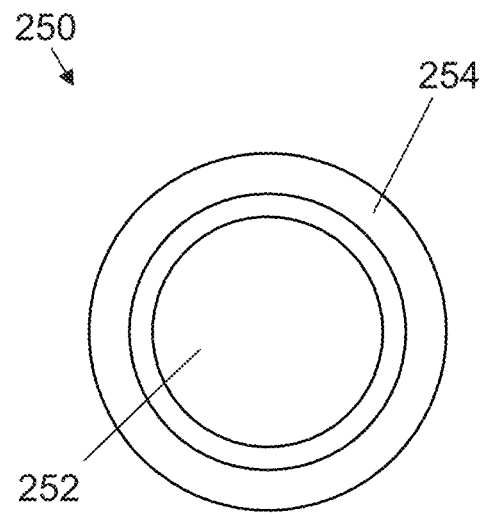
FIG. 15 is an axial view of the objects of FIG. 13.
Figure 16:
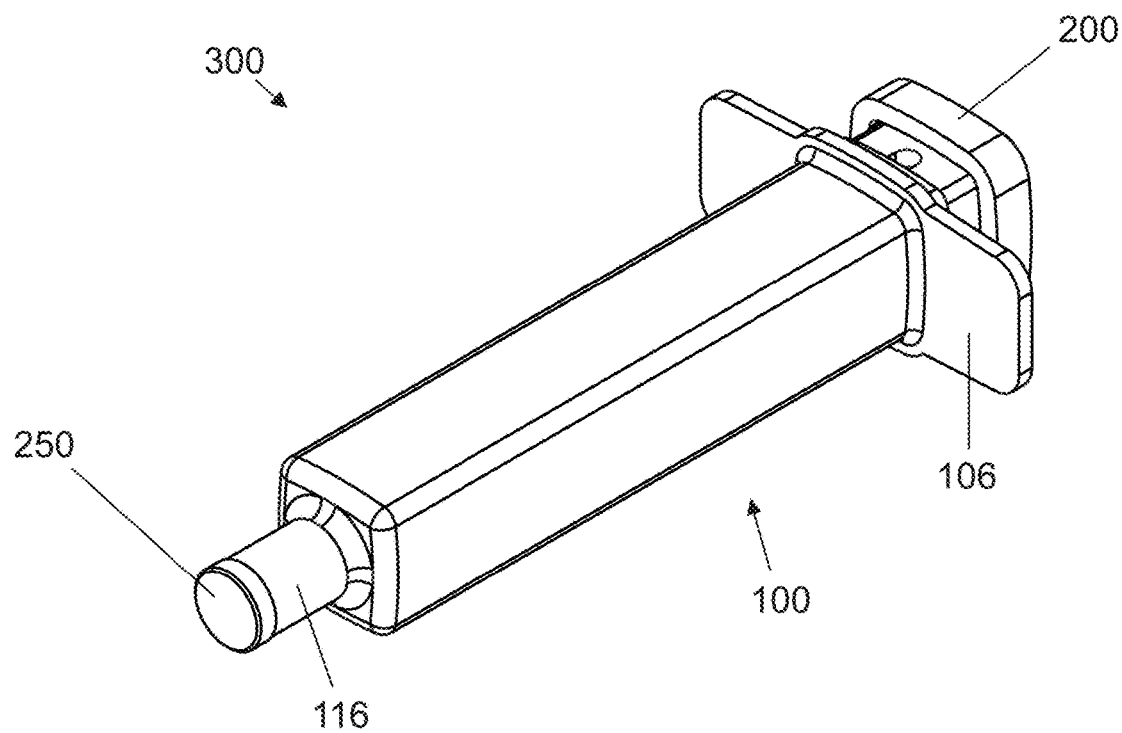
FIG. 16 is a distal perspective view of a syringe barrel assembly of the present in which the proximal stopper of FIG. 8 and distal cap of FIG. 13 are mounted to the syringe barrel of FIG. 1, and wherein the stopper is in a first axial position suitable for venting the barrel interior.
Figure 17:
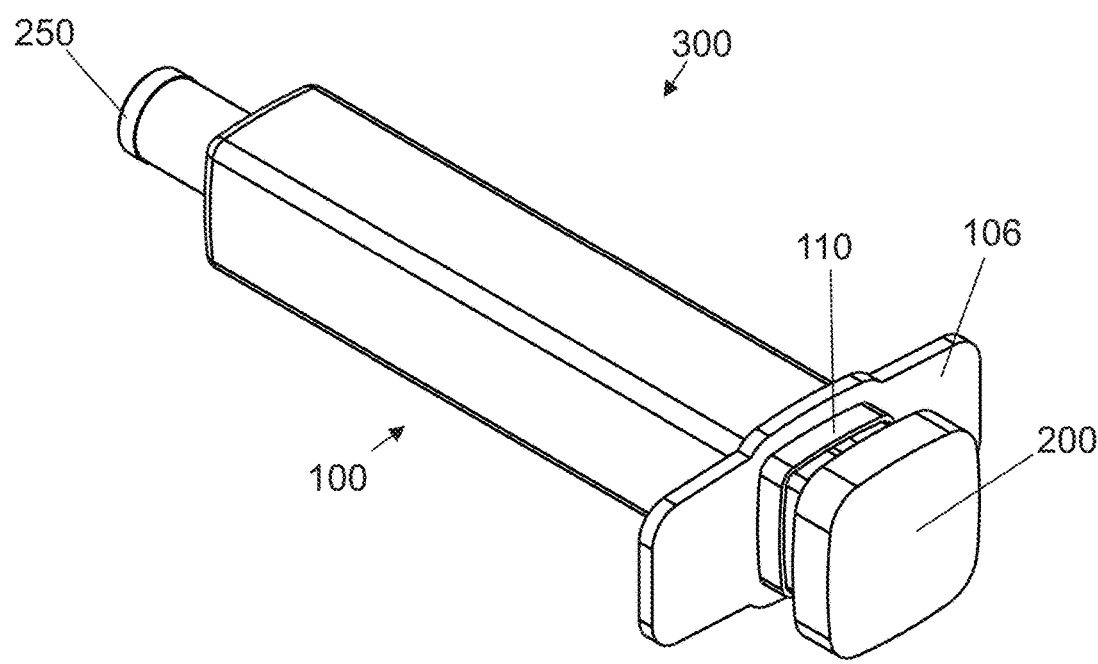
FIG. 17 is a proximal perspective view of the objects of FIG. 16.
Figure 18:
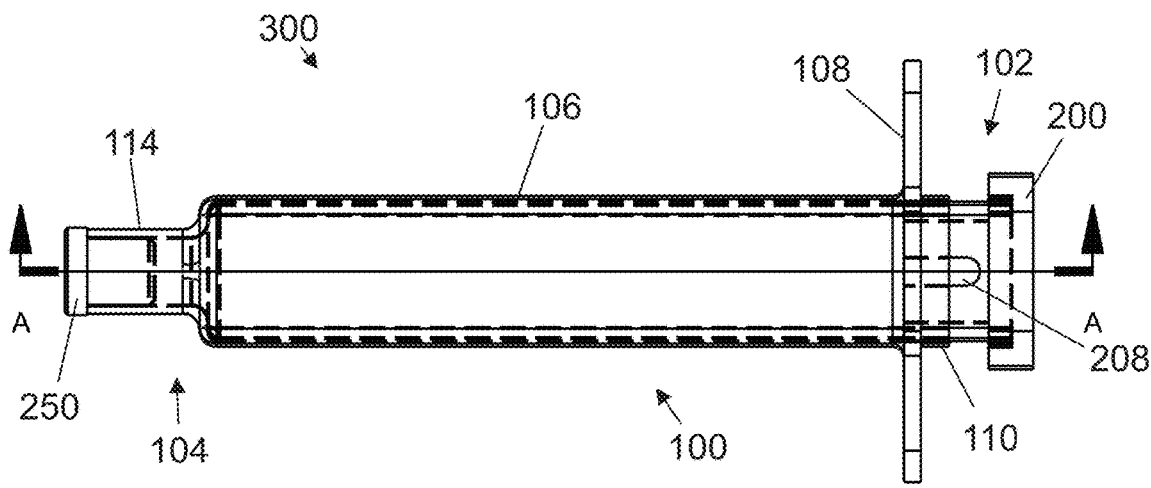
FIG. 18 is a plan view of the objects of FIG. 16.
Figure 19:
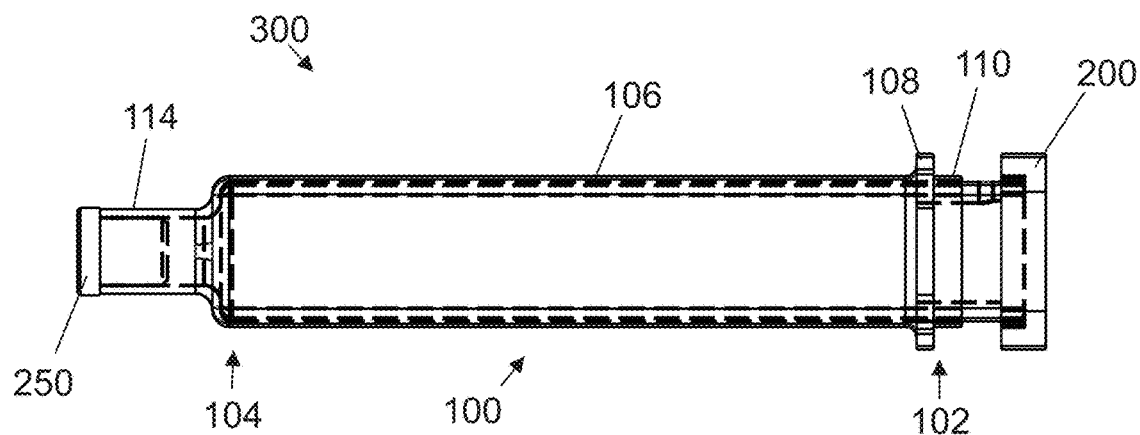
FIG. 19 is a side elevational view of the objects of FIG. 16.
Figure 20:
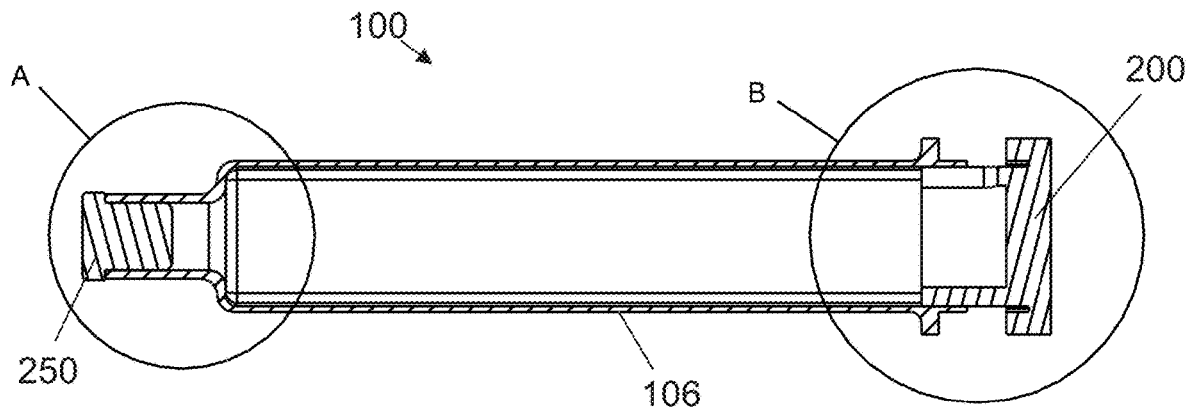
FIG. 20 is a sectional view of the objects of FIG. 18 at location A-A.
Figure 21:
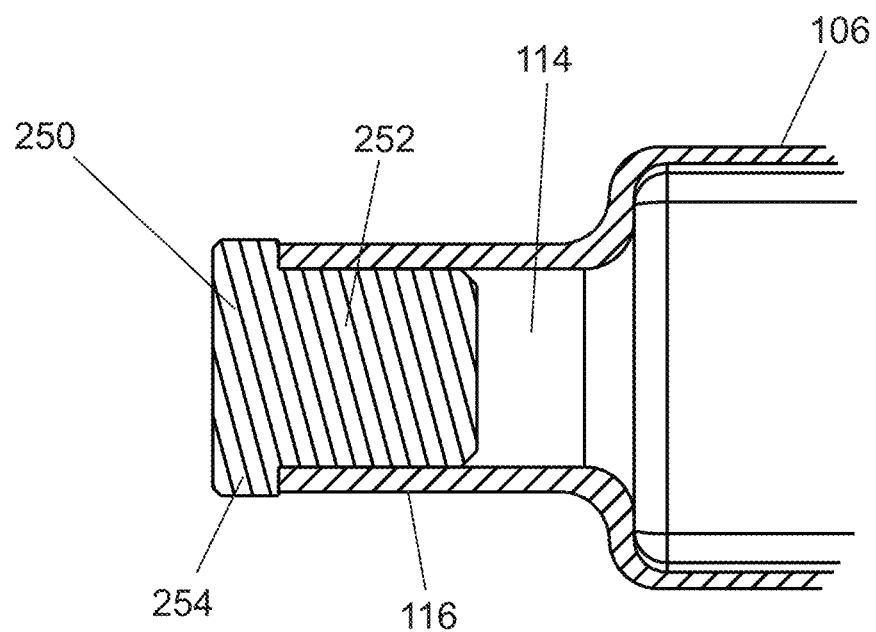
FIG. 21 is an expanded view of the objects of FIG. 20 at location A.
Figure 22:
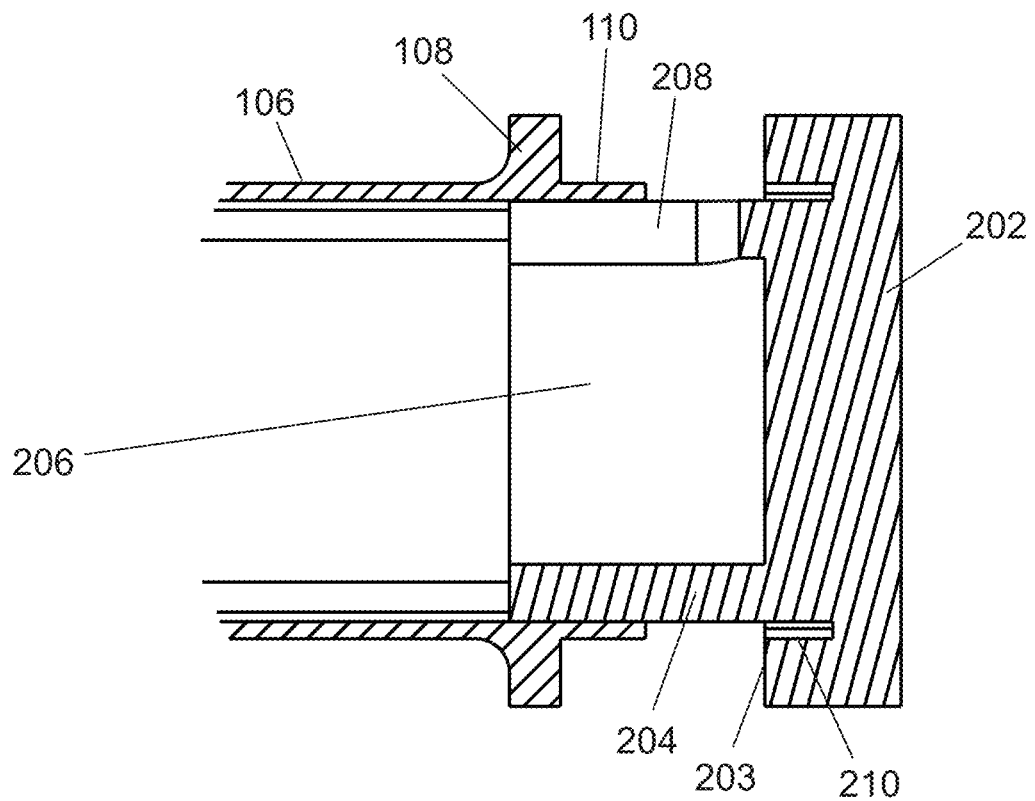
FIG. 22 is an expanded view of the objects of FIG. 20 at location B.
Figure 23:
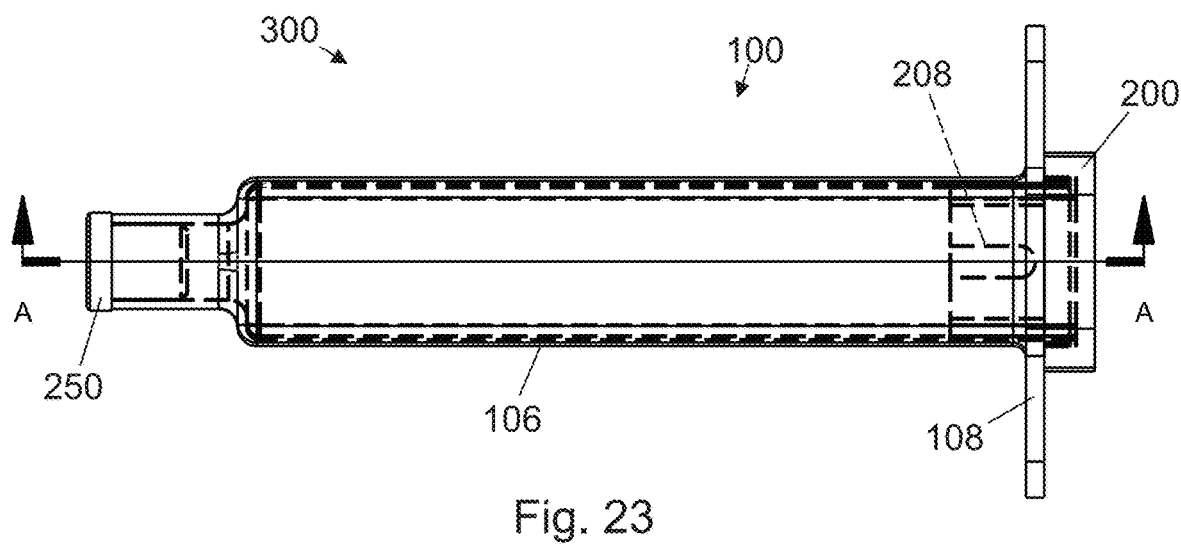
FIG. 23 is a plan view of the objects of FIG. 16 wherein the cap is in a second axial position suitable for sealing the barrel interior.
Figure 24:
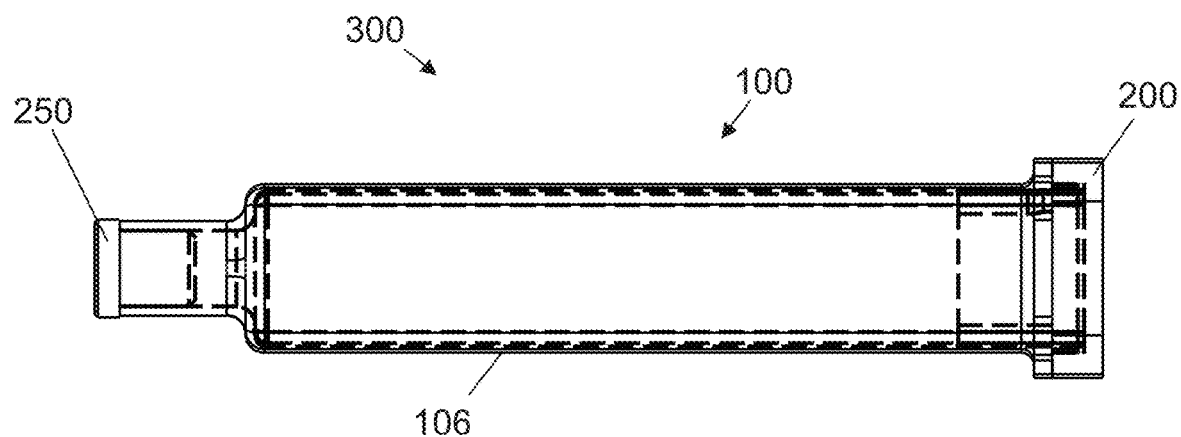
FIG. 24 is a side elevational view of the objects of FIG. 23
Figure 25:
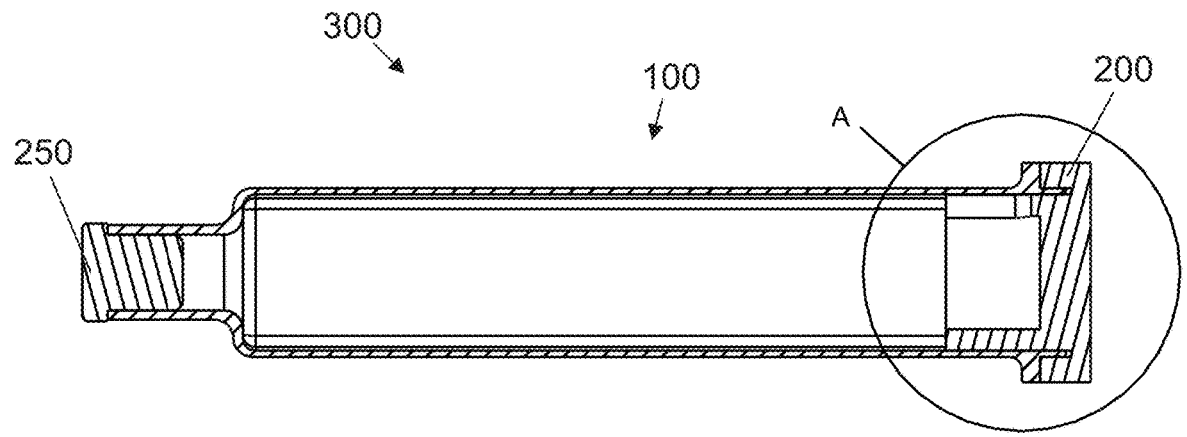
FIG. 25 is a sectional view of the objects of FIG. 23 at location A-A.
Figure 26:
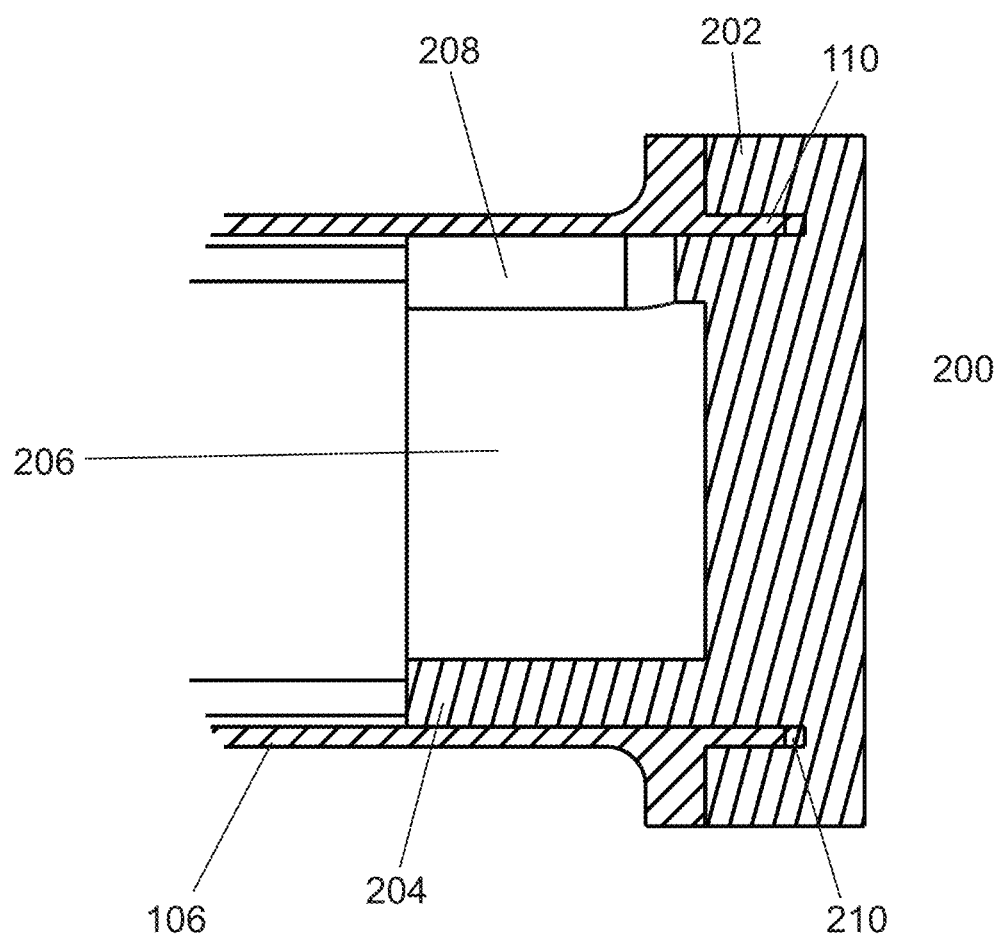
FIG. 26 is an expanded view of the objects of FIG. 25 at location A.

Cap 250, depicted in FIGS. 13 through 15 is configured for removable placement in output portion 112 of syringe barrel 100. Cap 250 has a proximal portion 252 and a distal portion 254. In a preferred embodiment, cap 250 is a Luer cap.

FIGS. 16 through 22 depict syringe assembly 300. Barrel 100 has cap 250 removably placed in distal output portion 116 of barrel 100 to seal the distal end of barrel 100. Stopper 200 is removably mounted to barrel 100 in a first, partially inserted position in which the proximal portion of slot 208 of stopper 200 is exposed so as to form a passage for gaseous outflow from the interior of syringe barrel 100.

Syringe assembly as pictured in FIGS. 23 through 26 is identical to assembly 300 of FIGS. 16 through 22 except that stopper 200 is fully inserted so that slot 208 is fully covered, thereby isolating the interior of syringe barrel 100 from the surrounding environment.

Hereafter, exemplary methods of the present invention for lyophilization of a product are described.

Figure 27:
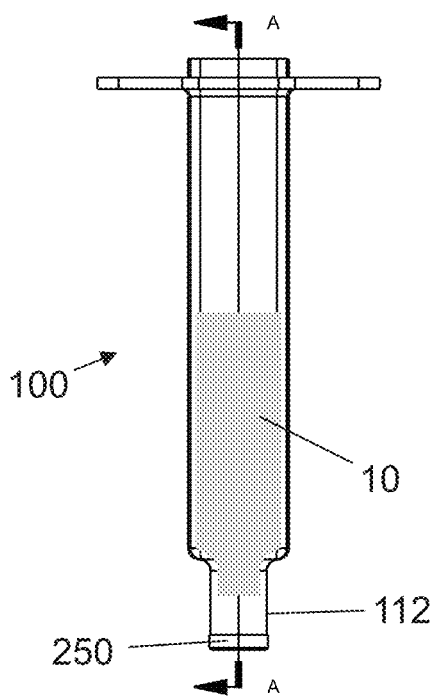
FIG. 27 depicts a syringe barrel of the present invention wherein a fluid product to be lyophilized has been placed in a first step of a lyophilization method of the present invention.
Figure 28:
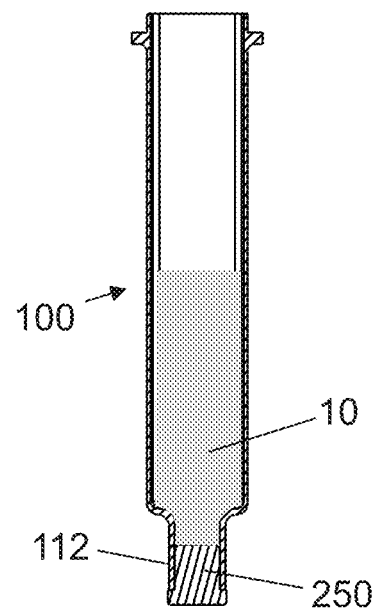
FIG. 28 is a sectional view of the objects of FIG. 27 at location A-A.
Figure 29:
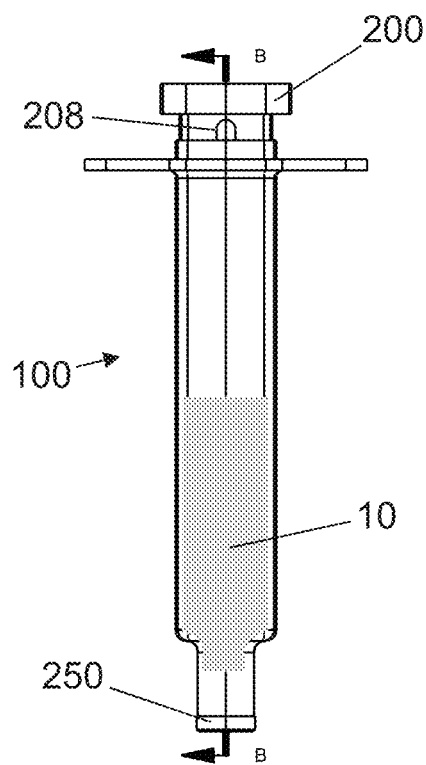
FIG. 29 depicts a second step in the method of the present invention in which the proximal stopper is placed on the syringe barrel in the "venting" position as in FIG. 16.
Figure 30:
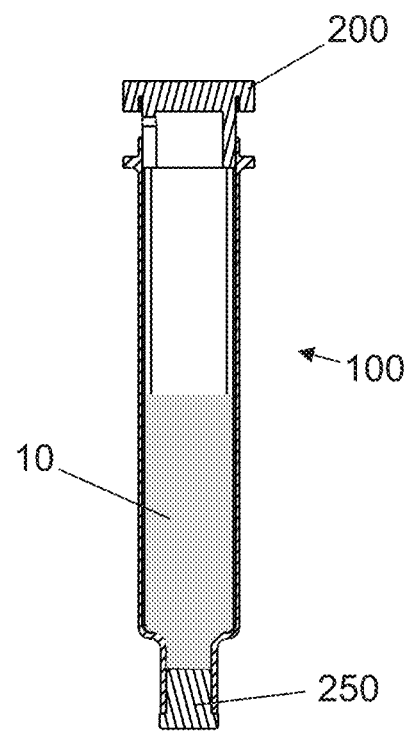
FIG. 30 is a sectional view of the objects of FIG. 29 at location A-A.

In a first step of the method depicted in FIGS. 27 and 28, a product 10 to be lyophilized is placed in syringe barrel 100, with cap 250 removably inserted onto distal portion 112. Referring now to FIGS. 29 and 30, in a second step of the method, stopper 200 is inserted into syringe barrel 100 and positioned as depicted in FIGS. 18 through 22, slot 208 in stopper 200 being exposed so as to provide an escape path for outgassing during the lyophilization process.

Figure 31:
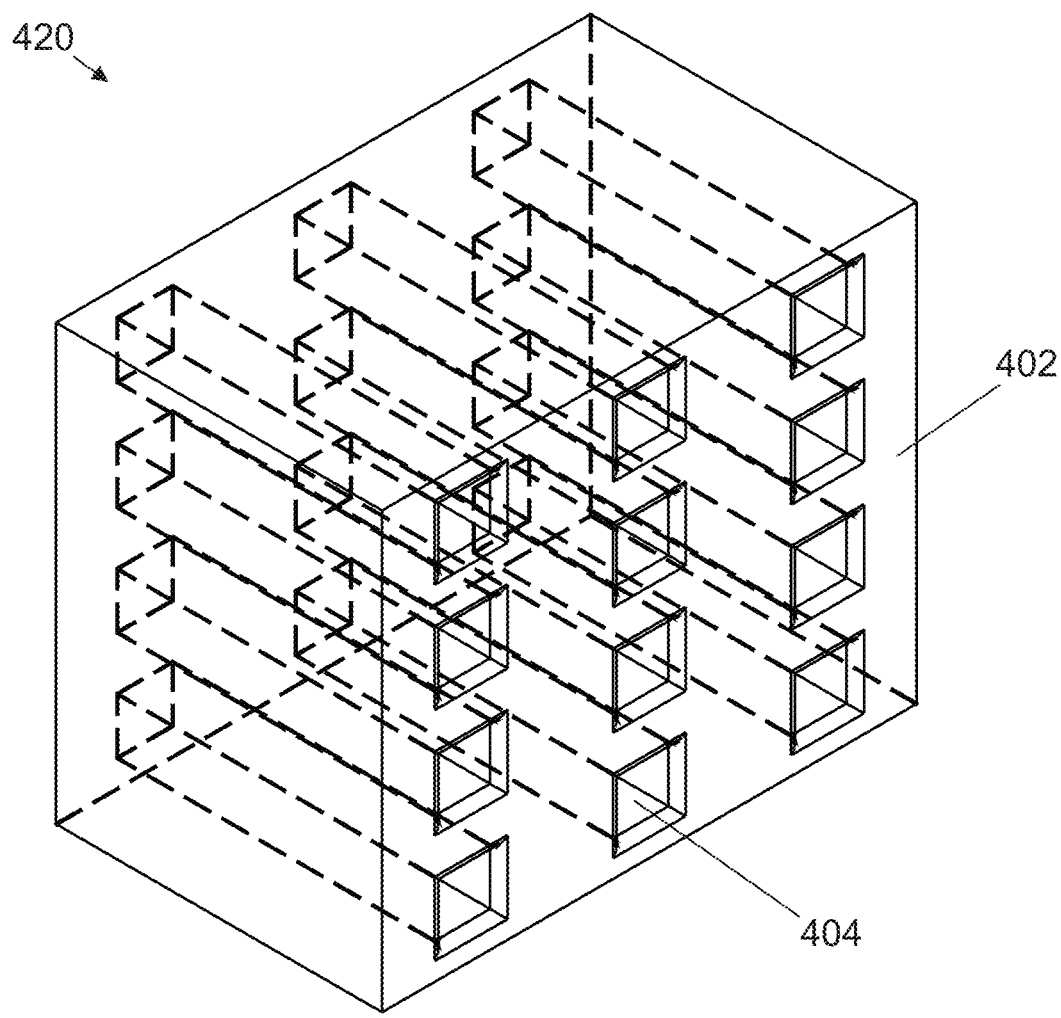
FIG. 31 is a perspective view of a thermal block of the present invention that has formed therein multiple wells for receiving syringe barrels of the present invention.
Figure 32:
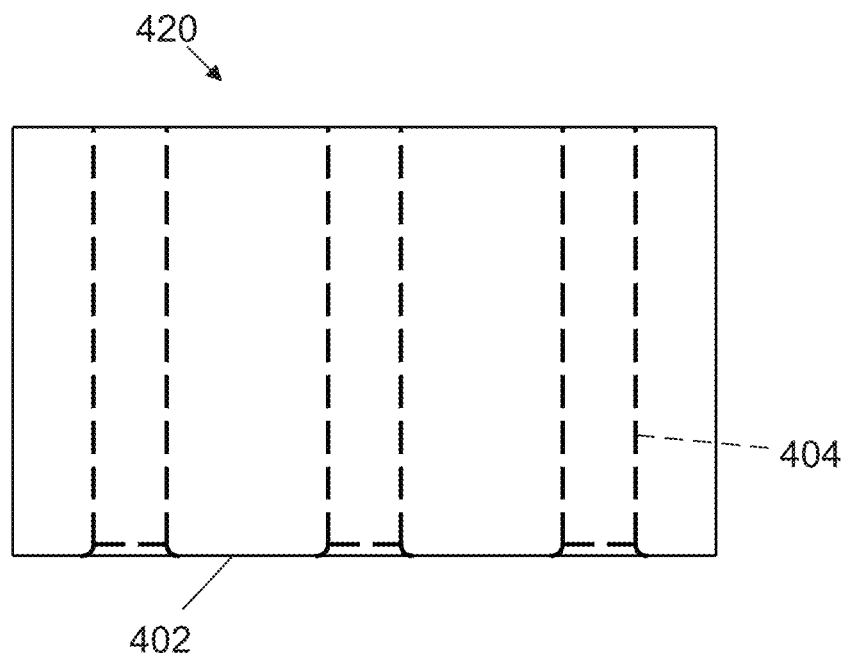
FIG. 32 is a plan view of the objects of FIG. 31.
Figure 33:
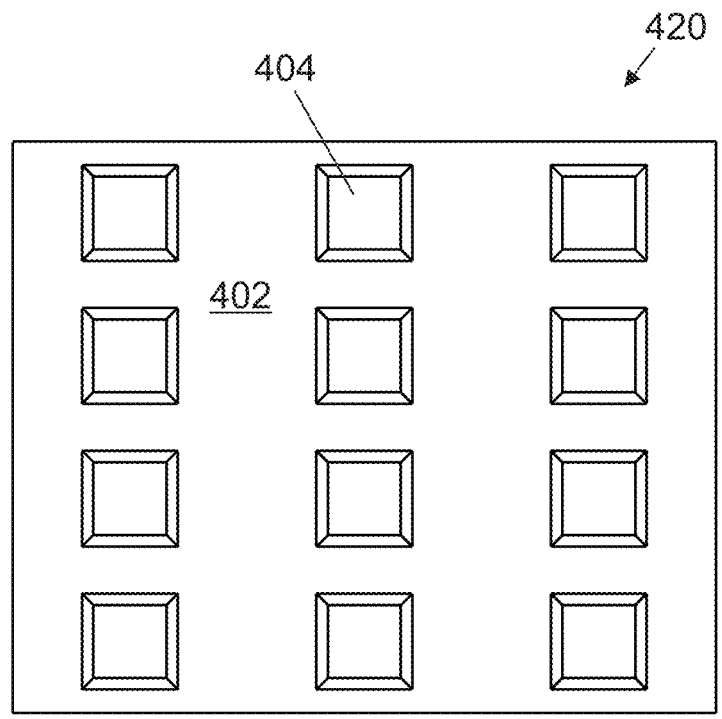
FIG. 33 is an axial end view of the objects of FIG. 31.
Figure 34:
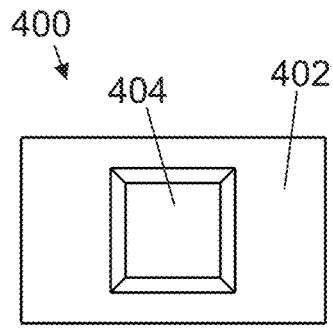
FIG. 34 is a plan view of a segment of the block of FIG. 31 containing a single well, hereinafter used to depict subsequent steps of an exemplary lyophilizing method of the present invention.
Figure 36:
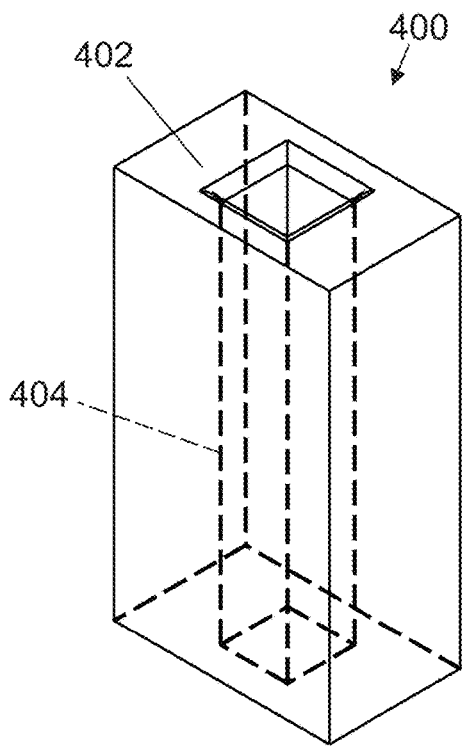
FIG. 36 is a perspective view of the objects of FIG. 34.
Figure 35:
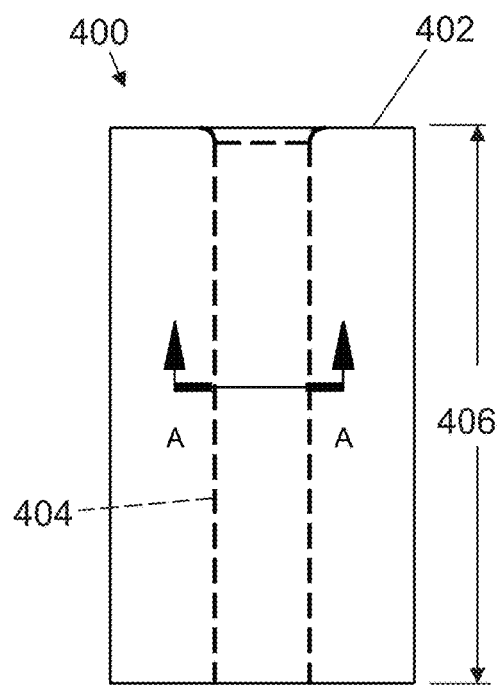
FIG. 35 is a side elevational view of the objects of FIG. 34.
Figure 37:
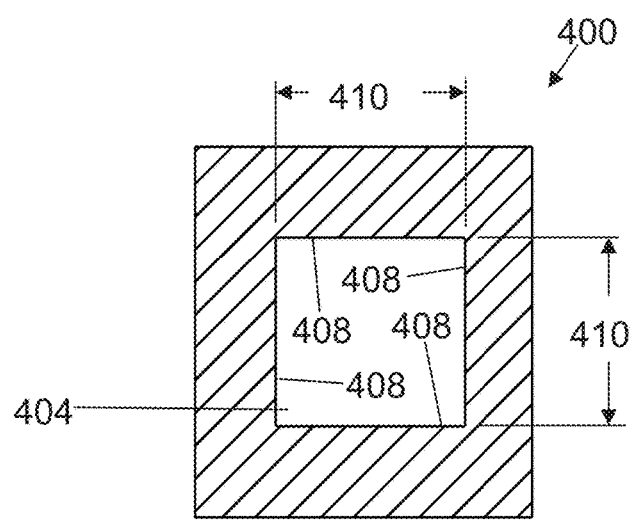
FIG. 37 is an expanded sectional view of the objects of FIG. 35 at location A-A.
Figure 41:
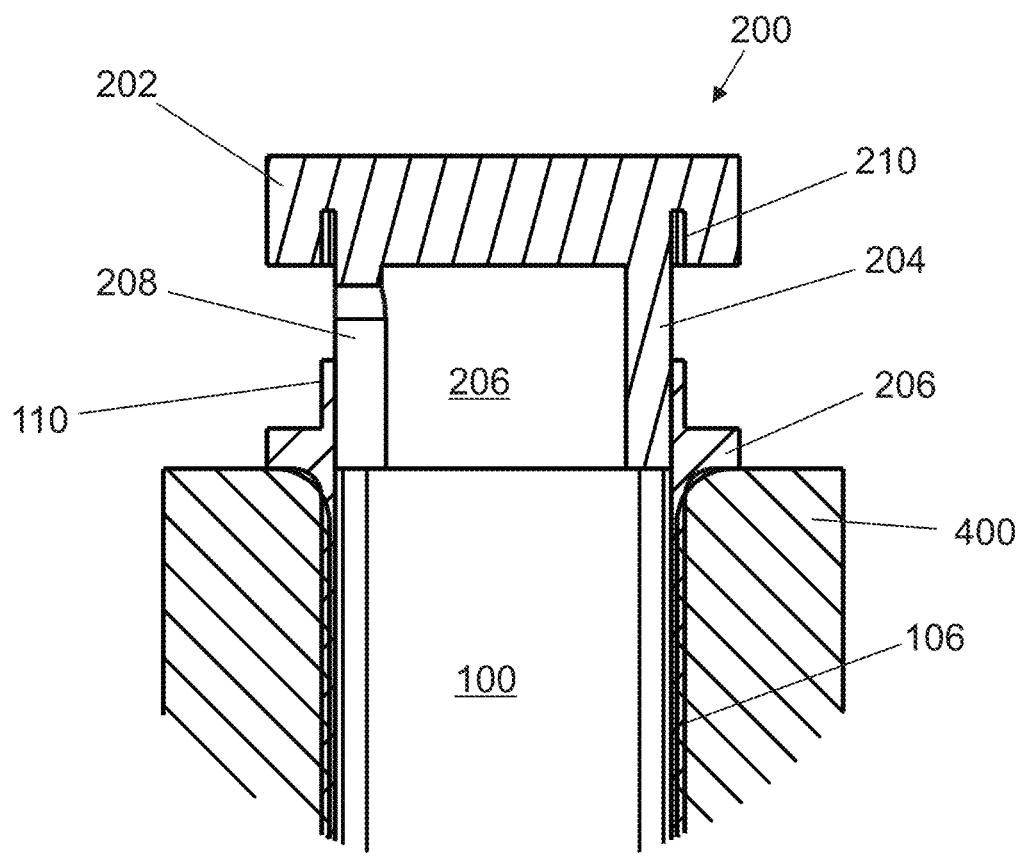
FIG. 41 is an expanded view of the objects of FIG. 39 at location A.
Figure 79:
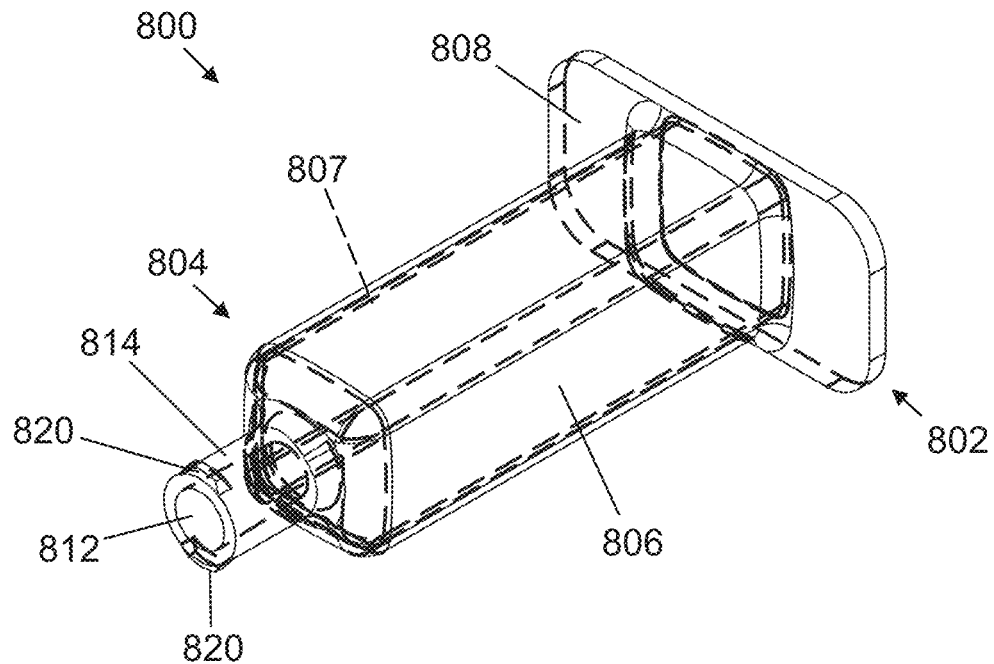
FIG. 79 is a distal perspective view of an alternate embodiment of a syringe barrel suitable for use in the combination lyophilization and dispensing syringe assembly of the present invention, wherein the syringe barrel is characterized by a non-circular, relatively square cross-section.

A first embodiment of a block 420 formed in accordance with principles of the present invention is depicted in FIGS. 31 through 33. An alternate embodiment in which the wells 1404 of the inventive block 1420 are more rounded in shape is depicted in FIG. 79. With reference to the former, block 420 has a first surface 402 in which are formed wells 404. The construct and function of block 420 will be now described with regard to a segment 400 of block 420 depicted in FIGS. 34 through 37 wherein segment 400 is oriented so that wells 404 are vertical. Segment 420 has a height 406 and wells 400 have a square shape of width and height 410. Well 404 has side walls 408. For simplicity, hereinafter block segment 400 will be referred to simply as "block" 400. It will be understood that this term refers to a segment of block 420 and is equally applicable to all well-containing segments of block 420.

In a third step of a lyophilization method of the present invention, syringe barrel 100 containing product 10 is inserted into block 400 as depicted in FIGS. 38 through 41. As best seen in FIG. 40, mid-portion 106 of syringe barrel 100 is tightly confined within well 404 of block 400, the convex walls of mid-portion 106 (see FIG. 7) being deformed so that outer surfaces 107 of mid-portion 106 of syringe barrel 100 are pressed tightly against inner surfaces 408 of well 404.

As discussed above, a close fit between the vessel containing the product and the well or other shaped cavity in a plate is necessary to achieve conductive heat transfer between the product and the plate. Moreover, it will be understood that conduction can only occur through surfaces that are in contact. If a vessel only closely conforms to the cavity in which it is placed, conduction will occur only in portions wherein the vessel and cavity are in contact. Voids between the vessel and the surrounding cavity effectively insulate the vessel since heat transfer must occur by radiation or convection. In the case of radiation, the temperature difference between the vessel/product and the cavity is insufficient to cause effective cooling. Since the lyophilization process occurs in a vacuum, there is no medium present for convective cooling.

In the assemblies and methods of the present invention, there is intimate contact between outer surfaces 107 of syringe barrel 100 and sidewalls 408 of well 400 so as to allow conductive heat transfer through virtually all walls of mid-portion 106 of syringe barrel 100.

Figure 42:
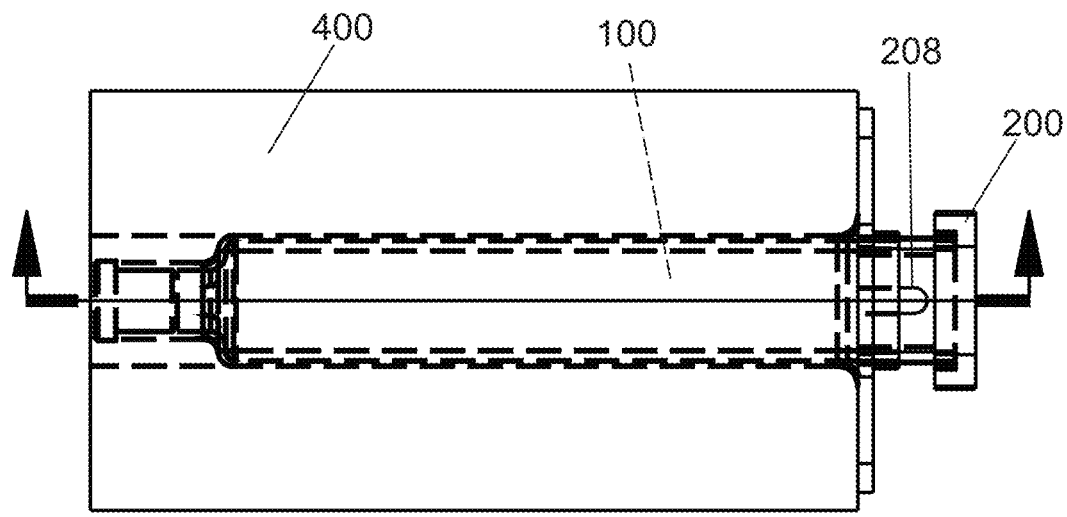
FIG. 42 depicts a fourth step in an exemplary lyophilization method of the present invention in which the block and syringe barrel are rotated so that the syringe barrel axis is horizontal and the fluid is in a liquid state.
Figure 43:
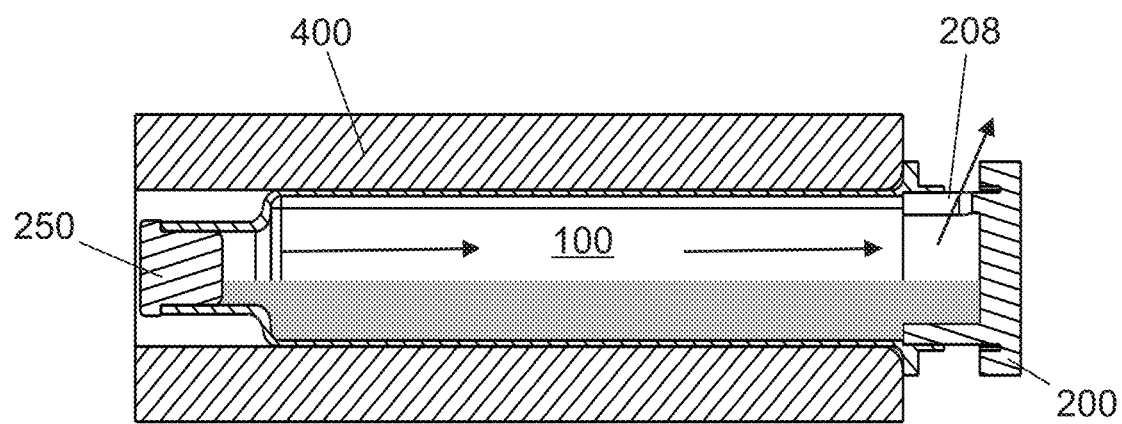
FIG. 43 is a sectional view of the objects of FIG. 42 at location A-A.

In a fourth step in a lyophilization method of the present invention depicted in FIGS. 42 and 43, block 400 and syringe assembly 300 contained therein are reoriented to a horizontal position. During lyophilization, water is removed by sublimation, a process that begins at the free surface of the product and progresses downward until all of the product is sublimated. The time required to complete the process is determined by the vertical distance through which the sublimation process must progress, and the rate of heat transfer to and from product 10. By reorienting block 400 and syringe assembly 300 to the horizontal position, the distance through which sublimation must progress is drastically reduced from what it was with block 400 and syringe assembly 300 in the vertical position. Also, because portions of mid-portion 106 of syringe barrel 100 containing product 10 have wall outer surfaces 107 in contact with inner surfaces 408 of well 404, heat transfer is optimal and evenly distributed to product 10.

Figure 44:
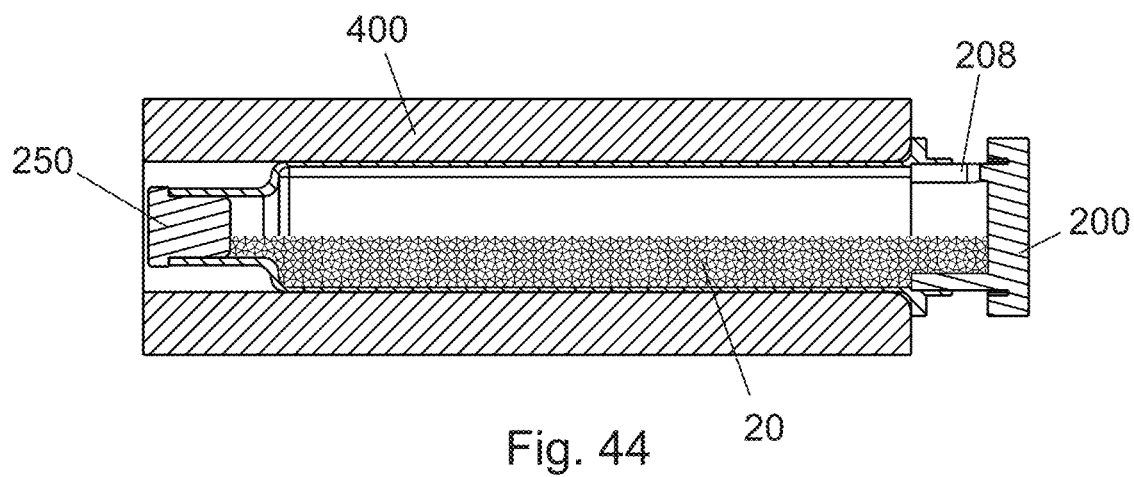
FIG. 44 depicts a fifth step in an exemplary lyophilization method of the present invention in which the liquid has been fully lyophilized.
Figure 45:
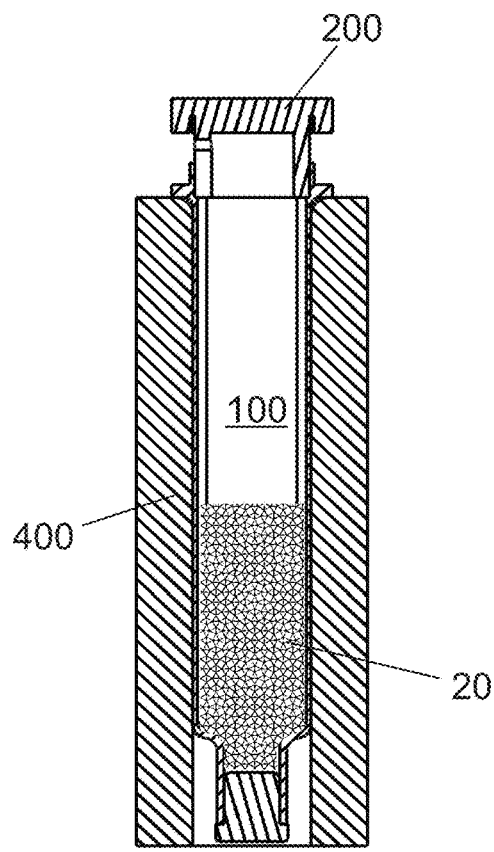
FIG. 45 depicts a sixth step in the method of the present invention wherein the syringe barrel and block are returned to a vertical position.
Figure 46:
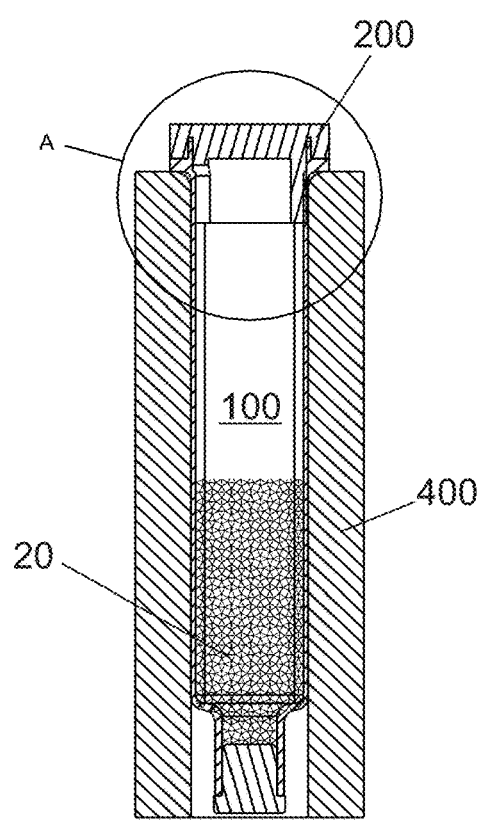
FIG. 46 depicts a seventh step in which the stopper is axially inserted into the syringe barrel to its second, sealing position.
Figure 47:
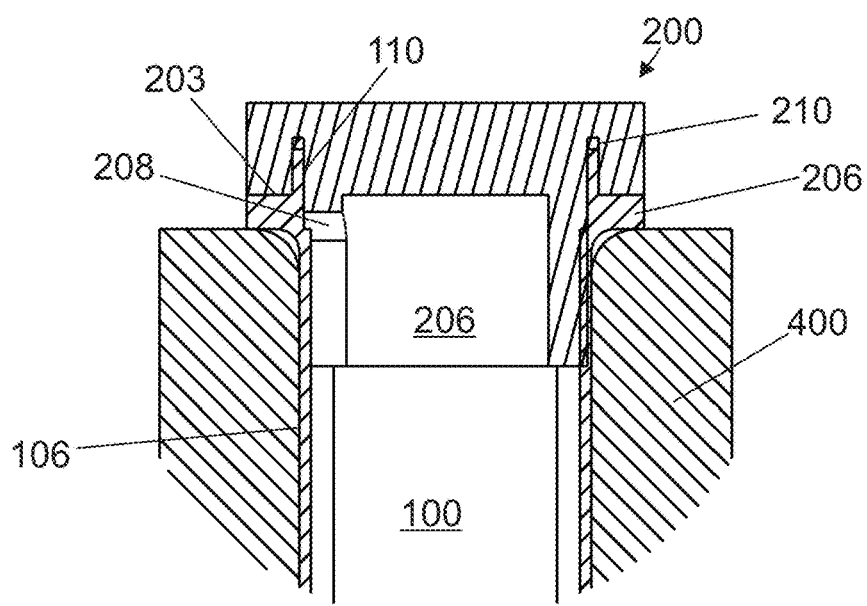
FIG. 47 is an expanded view of the objects of FIG. 46 at location A.

In FIG. 44, sublimation of product 10 has been completed so as to produce lyophilized product 20. Block 400 and syringe assembly 300 contained therein are returned to a vertical orientation in a fifth step of the method of the present invention depicted in FIG. 45. In a sixth step of the method, stopper 200 is inserted fully into syringe barrel 100 as depicted in FIGS. 46 and 47, rim 110 of syringe barrel 100 being positioned within slot 210 of stopper 200, and slot 208 of stopper 200 being covered so as to seal lyophilized product 20 within syringe assembly 300.

Figure 48:
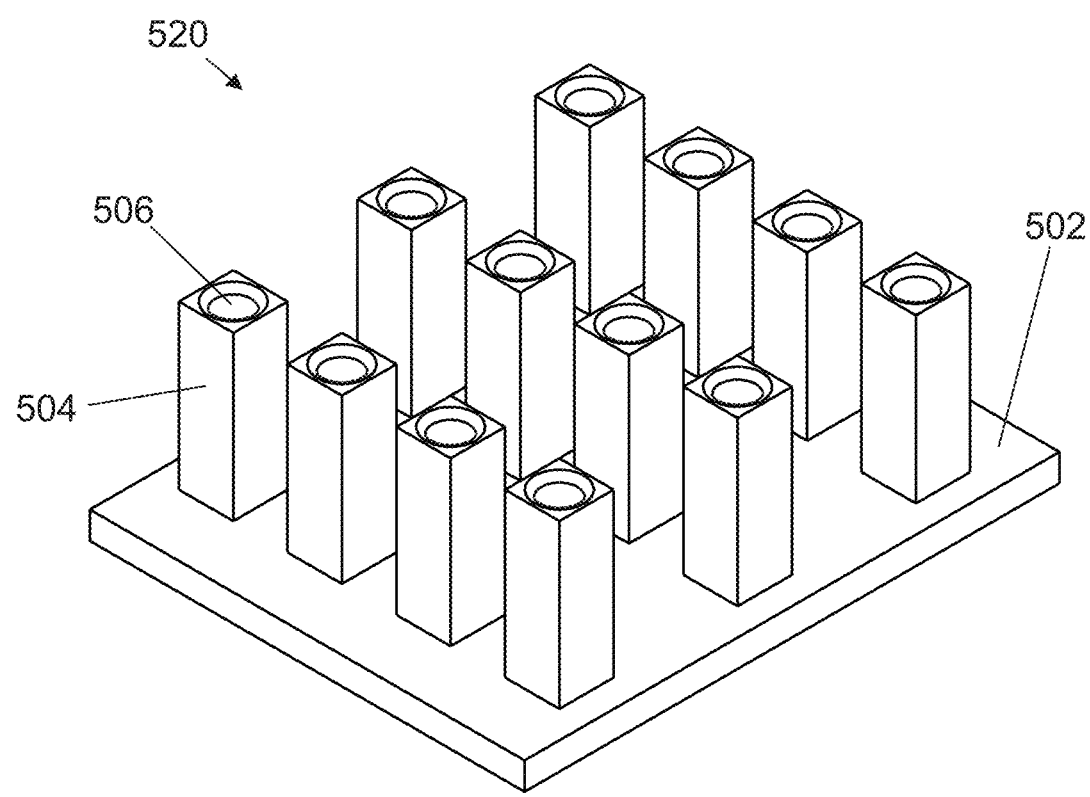
FIG. 48 depicts an ejector plate for use with the thermal block of FIG. 31.
Figure 49:
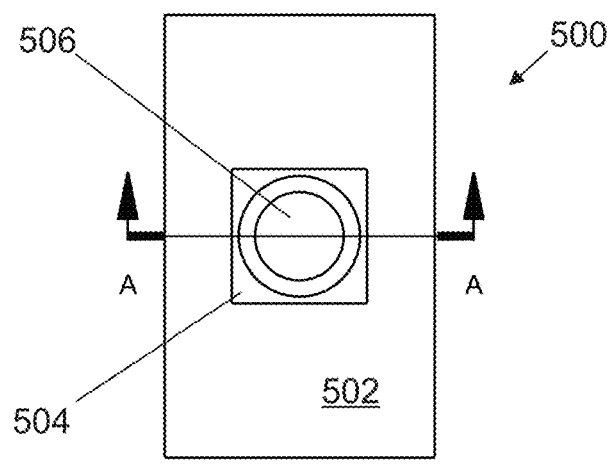
FIG. 49 is a plan view of a segment of the ejector plate of FIG. 48 containing a single upright, hereinafter used to depict subsequent steps of a lyophilizing method of the present invention.
Figure 50:
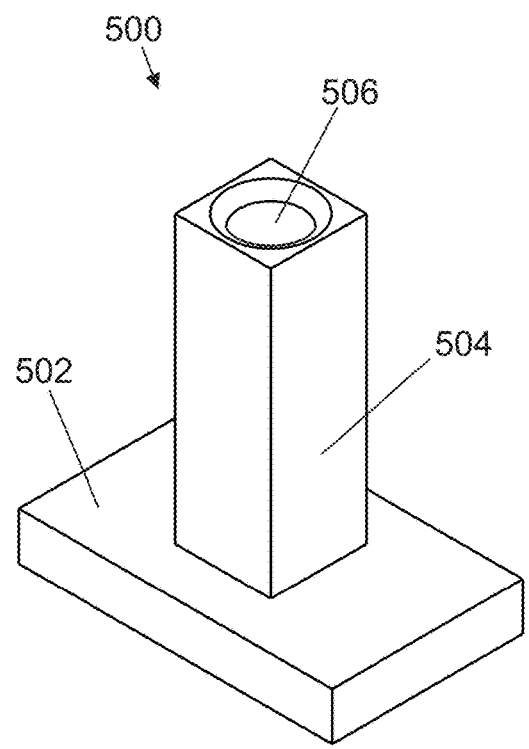
FIG. 50 is a perspective view of the objects of FIG. 49.
Figure 51:
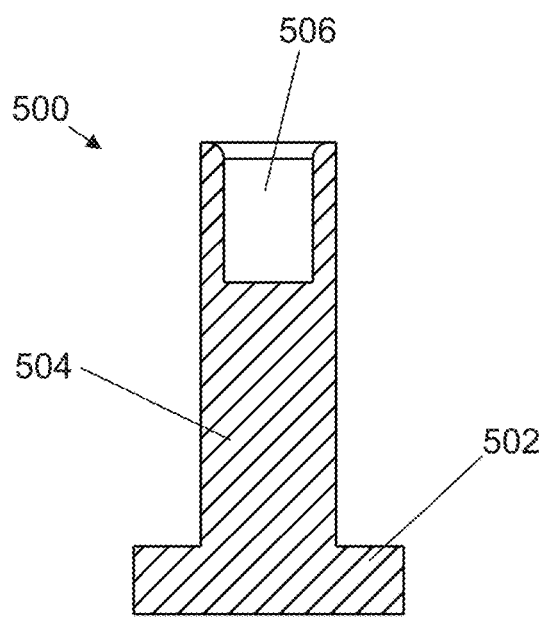
FIG. 51 is a sectional view of the objects of FIG. 49 at location A-A.
Figure 52:
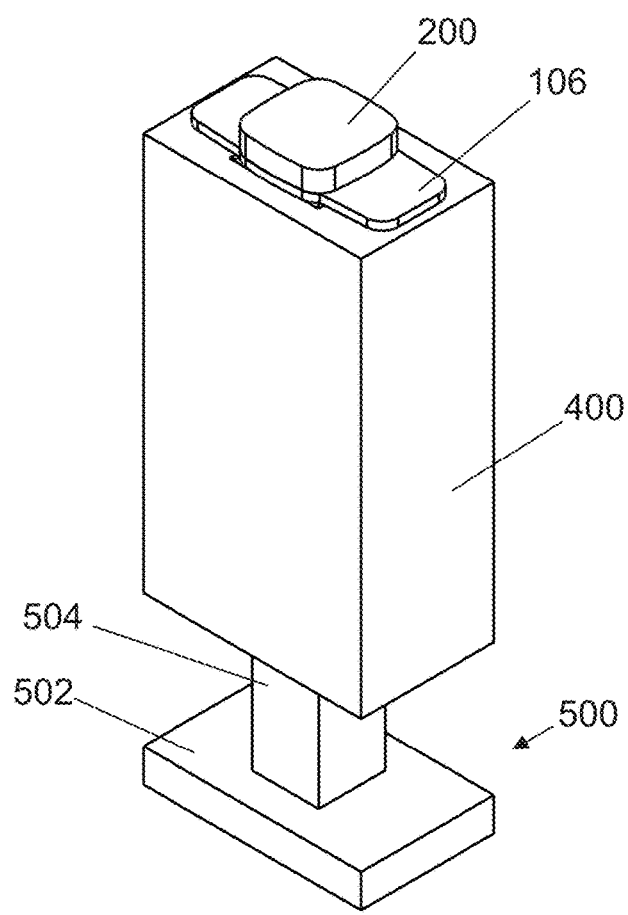
FIG. 52 is an upper perspective view of an eighth step in the exemplary method of the present invention, wherein the block and syringe barrel are positioned on the upright of the ejector segment of FIG. 49.
Figure 53:
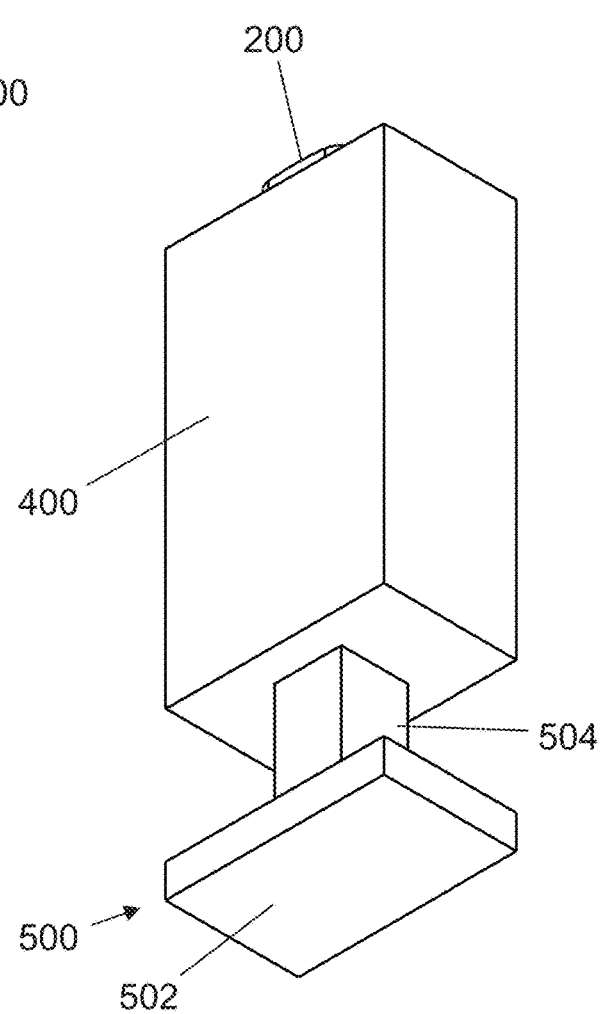
FIG. 53 is a lower perspective view of the objects of FIG. 52.
Figure 54:
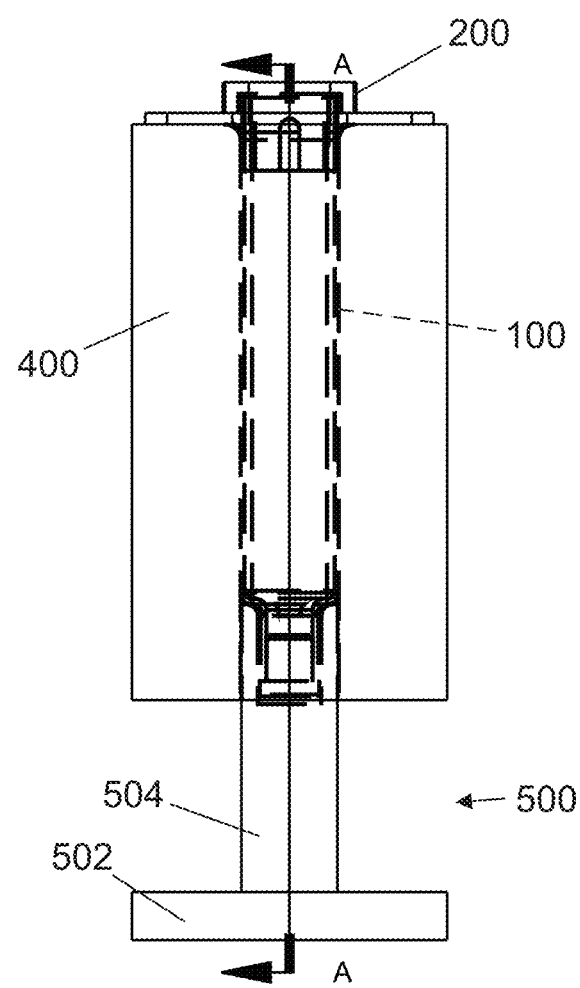
FIG. 54 is a side elevational view of the objects of FIG. 52.
Figure 55:
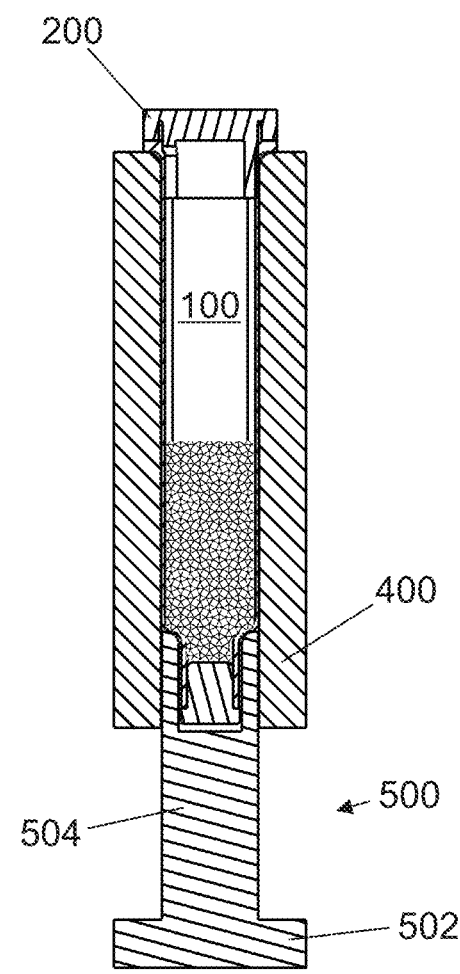
FIG. 55 is a sectional view of the objects of FIG. 54 at location A-A.

FIG. 48 depicts an ejector plate 520 that may be used to assist in the removal of the plurality of syringes 300 from the wells of block 420 (FIGS. 31 through 33). Ejector plate 520 has a planar base 502 from which protrude vertical portions 504. Vertical portions 504 have formed in their top surface's recesses 506, recesses 506 being configured to accommodate distal portions 114 of syringe barrel 100, and cap 250 positioned thereon. FIGS. 49 through 51 depict a segment 500 of ejector plate 520 containing a single vertical portion 504. Hereinafter the function of ejector plate 520 will be described using segment 500. For simplicity, segment 500 of ejector plate 520 will be referred to as "ejector 500" in the following descriptions. It will be understood that descriptions of the ejector functions so described are applicable to all segments of ejector plate 520.

Figure 56:
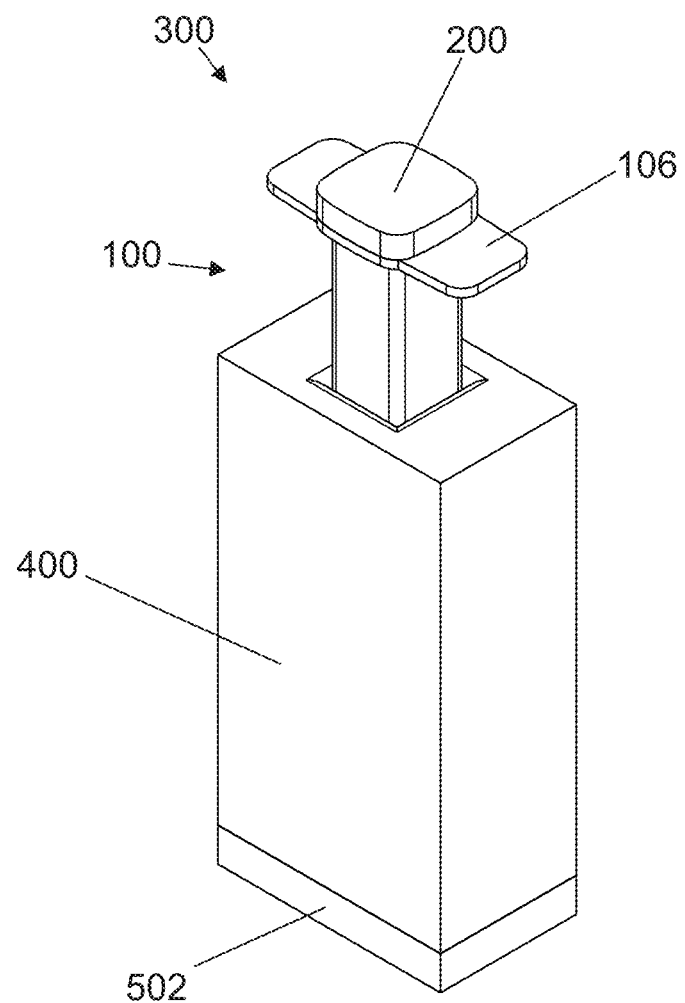
FIG. 56 is a perspective view of a ninth step in the exemplary method of this invention in which the syringe barrel is partially ejected from the block segment.
Figure 57:
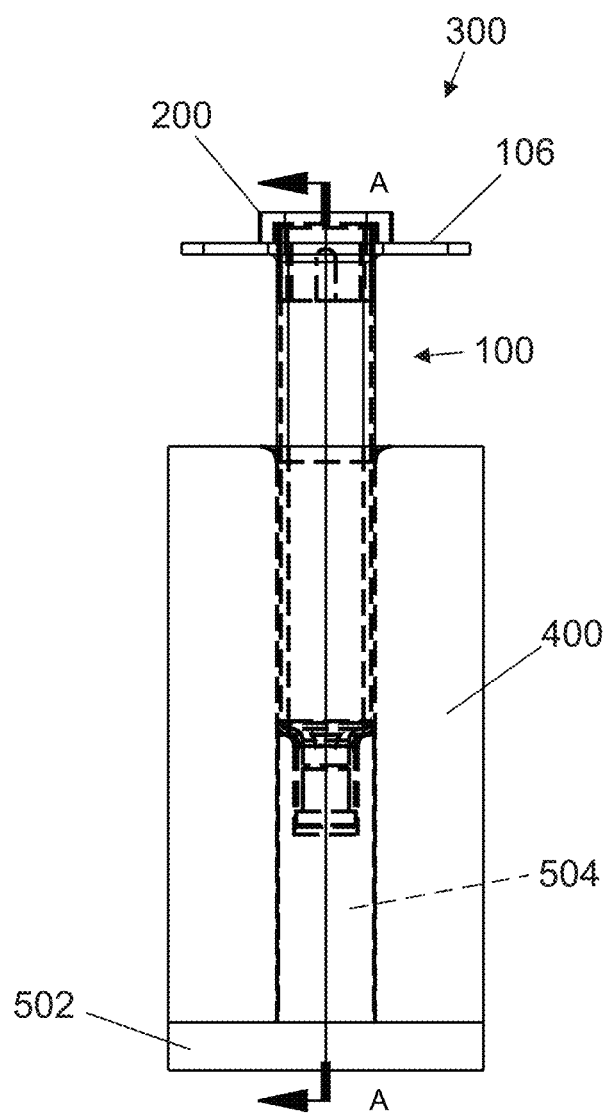
FIG. 57 is a side elevational view of the objects of FIG. 56.
Figure 58:
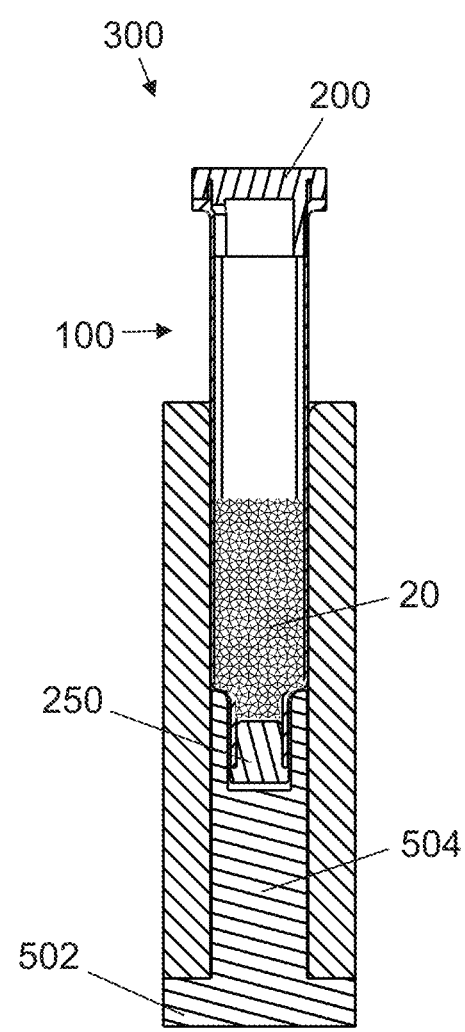
FIG. 58 is a sectional view of the objects of FIG. 57 at location A-A.

Block 400 with syringe assembly 300 therein may be positioned on ejector 500 as depicted in FIGS. 52 through 55. Moving block 400 downward as depicted in FIGS. 56 through 58 causes syringe assembly 300 to be partially dislodged from block 400 so as to allow easy manual removal of syringe assembly 300 from block 400.

FIGS. 59 and 60 depict lyophilized product 20 in sealed syringe assembly 300 at the completion of lyophilization using methods and devices of the present invention.

In methods and devices previously herein described, at completion the product is contained in a syringe assembly sealed with a cap. Before use of the product, the cap must be removed and a diluent added to the syringe for reconstitution of the lyophilized product. Thereafter, a combination of piston and plunger may be inserted into the syringe body and the medication may be administered to the patient. In other methods of the present invention the lyophilized product is contained within a syringe wherein the piston component is already in place and provides the proximal seal. This is advantageous as it minimizes steps required before administration of the product with their associated potential for compromised product or wastage.

An exemplary method for producing lyophilized product in a syringe ready for solubilization and administering to a patient is hereafter described.

Figure 61:
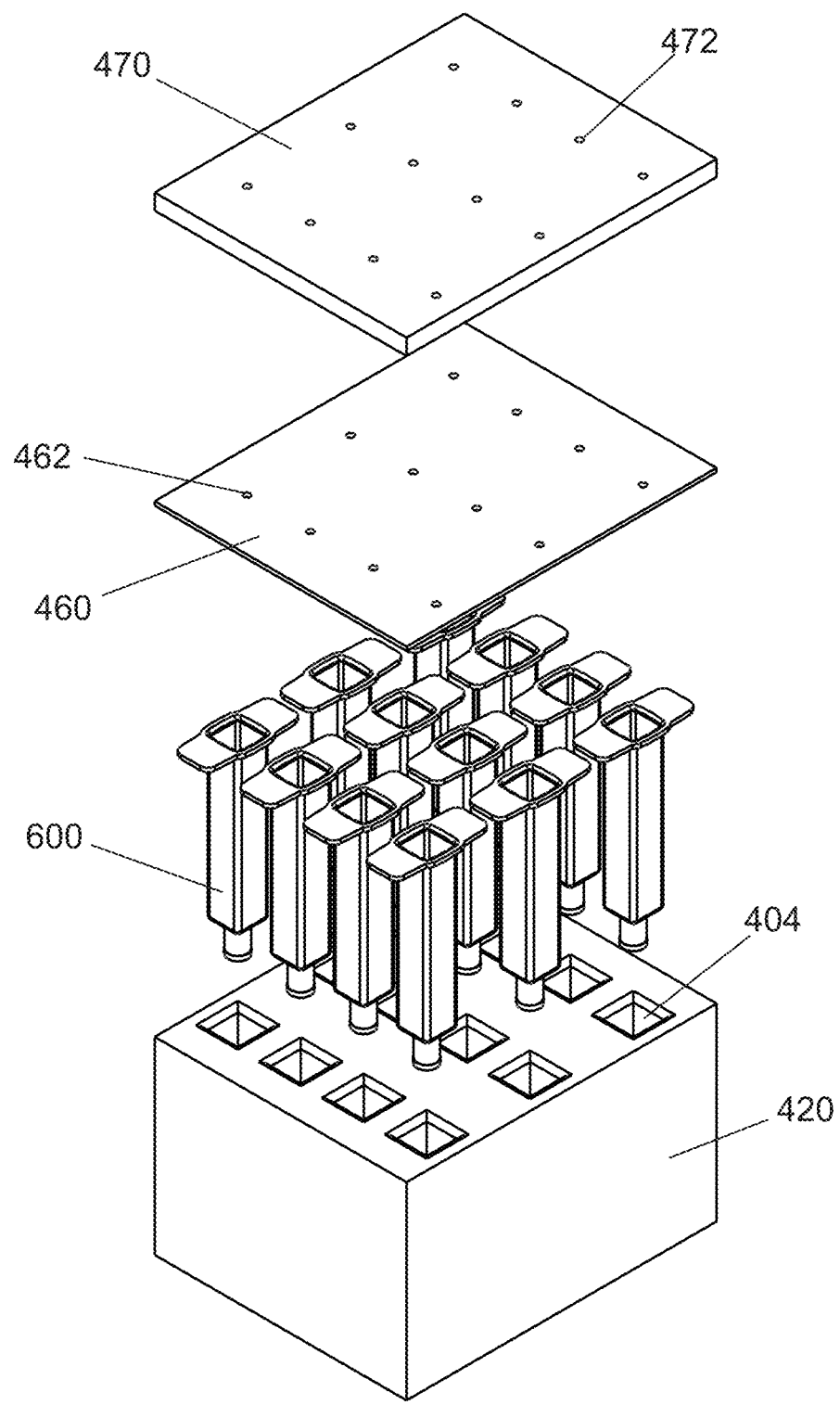
FIG. 61 is a perspective view of an exploded assembly useful in an alternate embodiment lyophilization method of the present invention.
Figure 62:
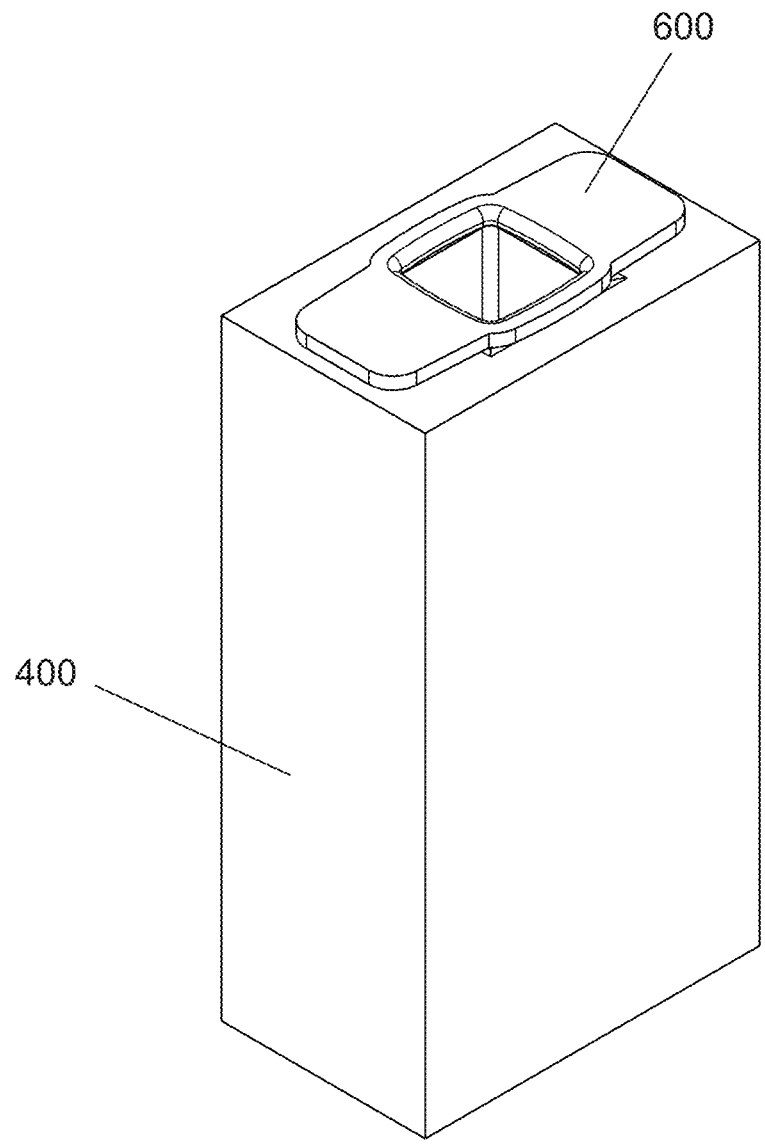
FIG. 62 depicts a second syringe barrel of the present invention containing fluid for lyophilization is inserted into a thermal block segment in a first step of an alternate lyophilization method of the present invention.
Figure 63:
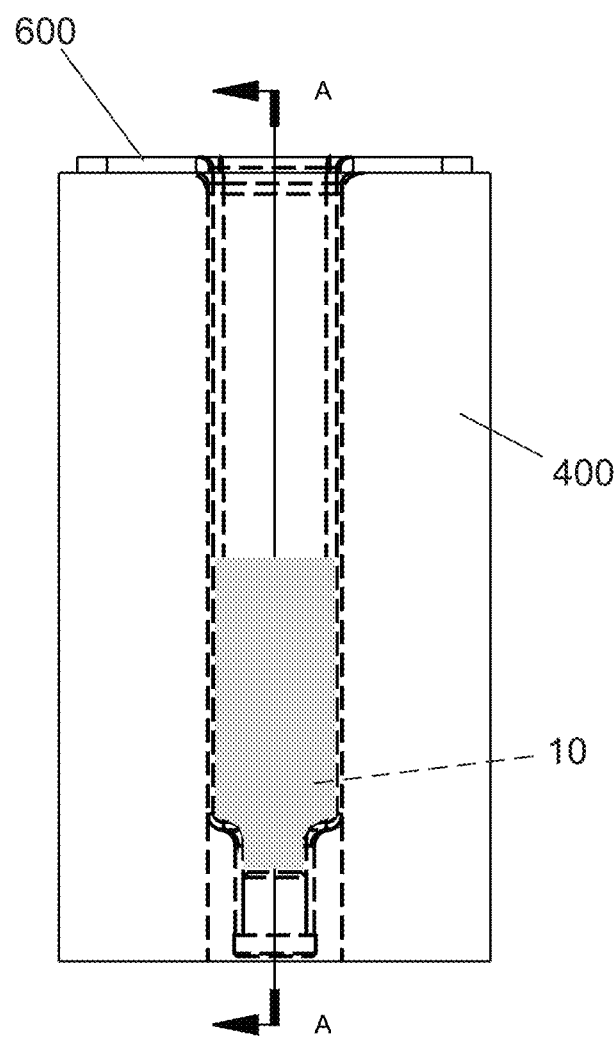
FIG. 63 is a side elevational view of the objects of FIG. 62.
Figure 64:
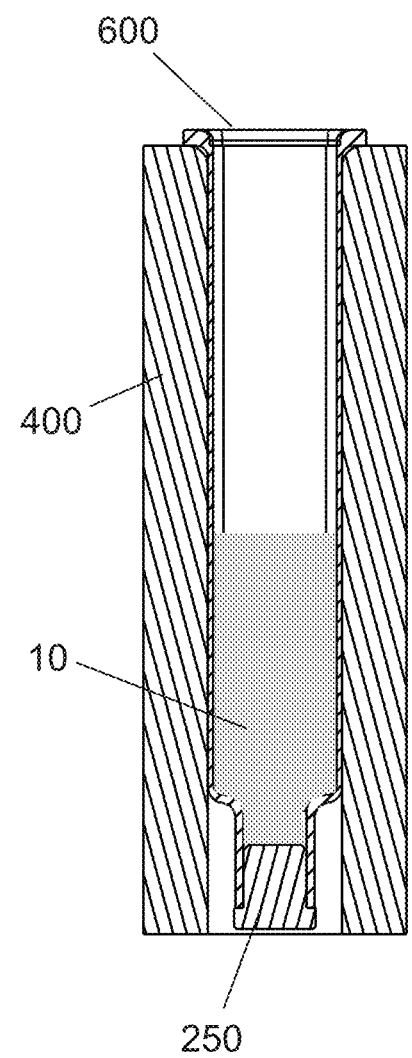
FIG. 64 is a sectional view of the objects of FIG. 63 at location A-A.
Figure 67:
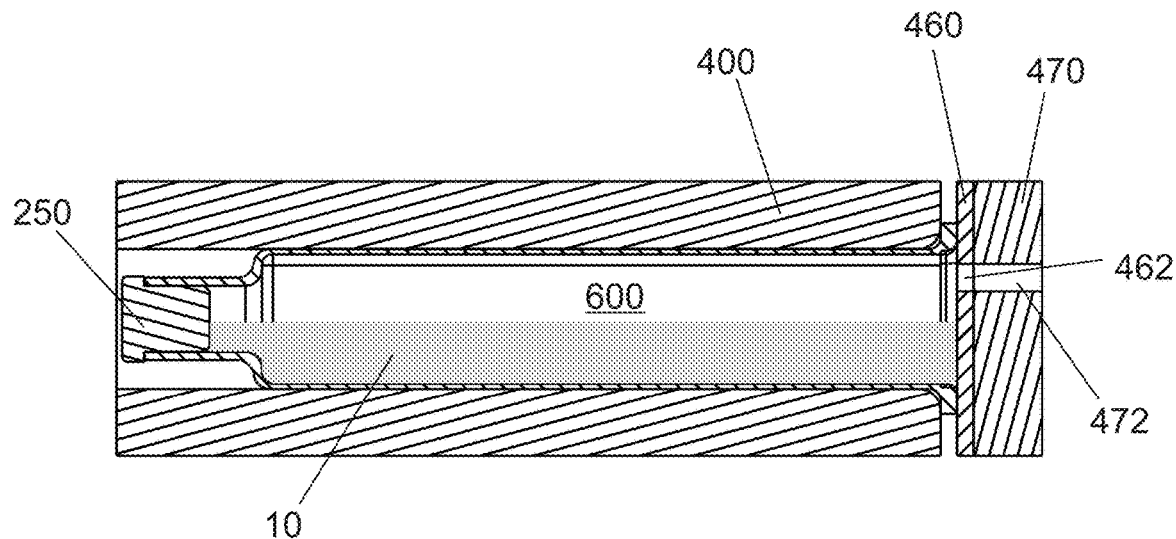
FIG. 67 depicts a third step in which the objects of FIG. 65 are reoriented into a horizontal position.
Figure 68:
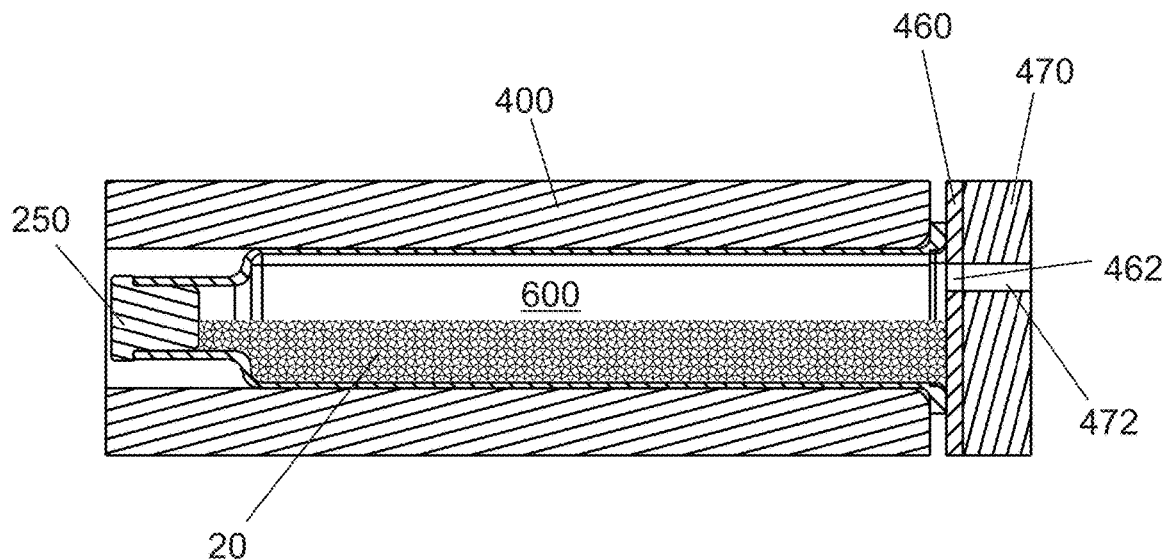
FIG. 68 depicts a fourth step in which the fluid has been fully lyophilized.
Figures 69, 70:
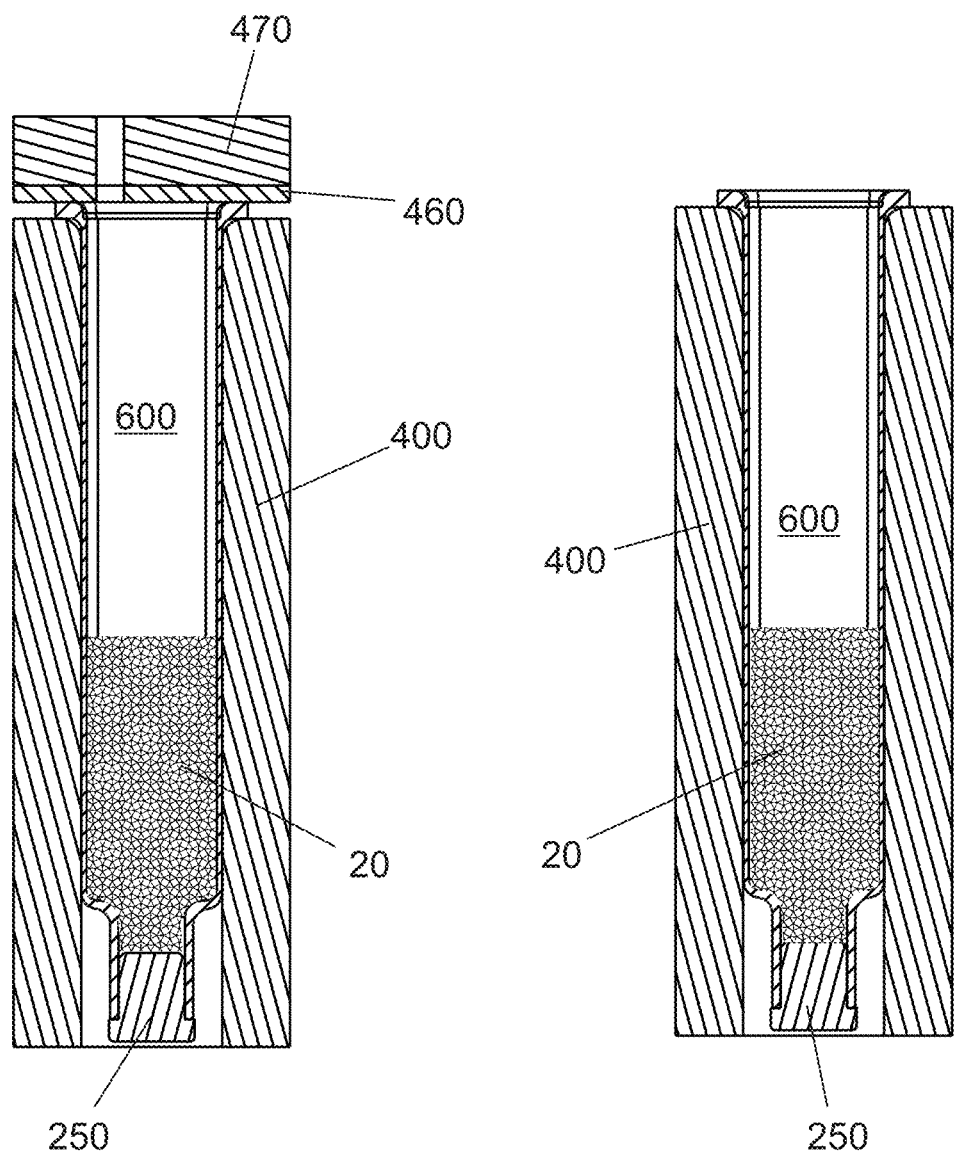
FIG. 69 depicts a fifth step in which the syringe barrel and block have been returned to a vertical position.
FIG. 70 depicts a sixth step in which the plate and gasket have been removed.
Figure 71:
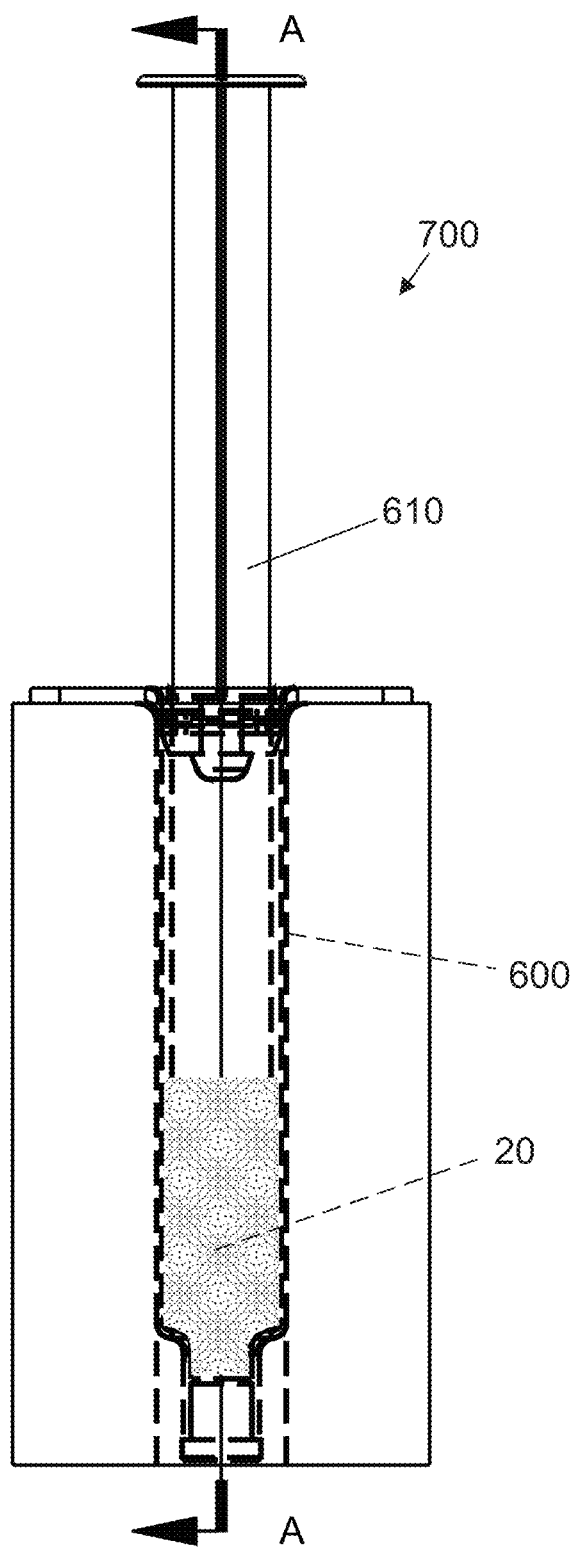
FIG. 71 depicts a seventh step in the alternate lyophilization method in which a plunger is axially inserted into the syringe barrel until a seal is formed between the barrel and the plunger stopple (or stopper) so as to seal the lyophilized material within the plunger barrel.
Figure 72:
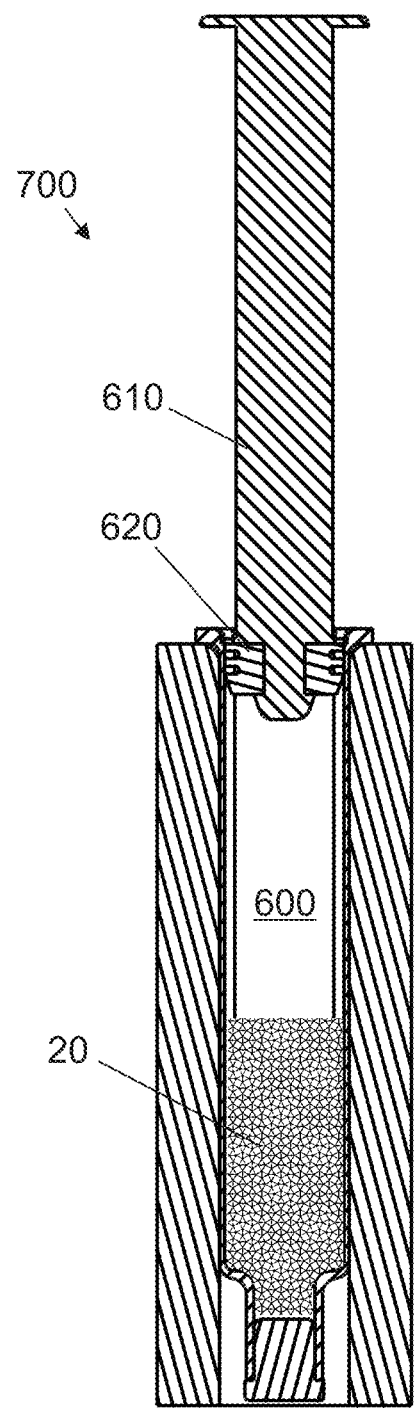
FIG. 72 is a sectional view of the objects of FIG. 71 at location A.
Figure 75:
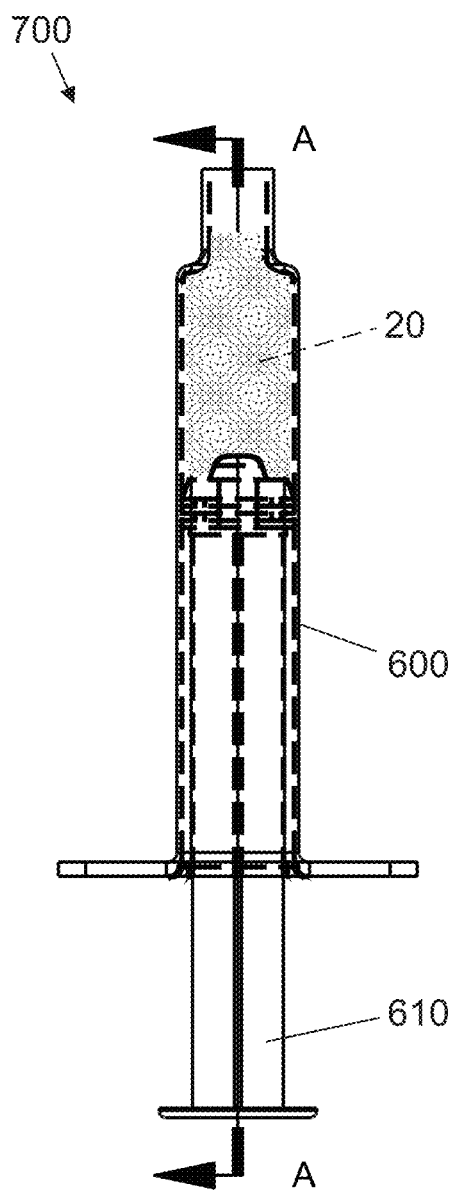
FIG. 75 depicts a ninth step in which the distal cap is removed and the plunger is axially advanced with the distal end elevated, in the vertical orientation.
Figure 76:
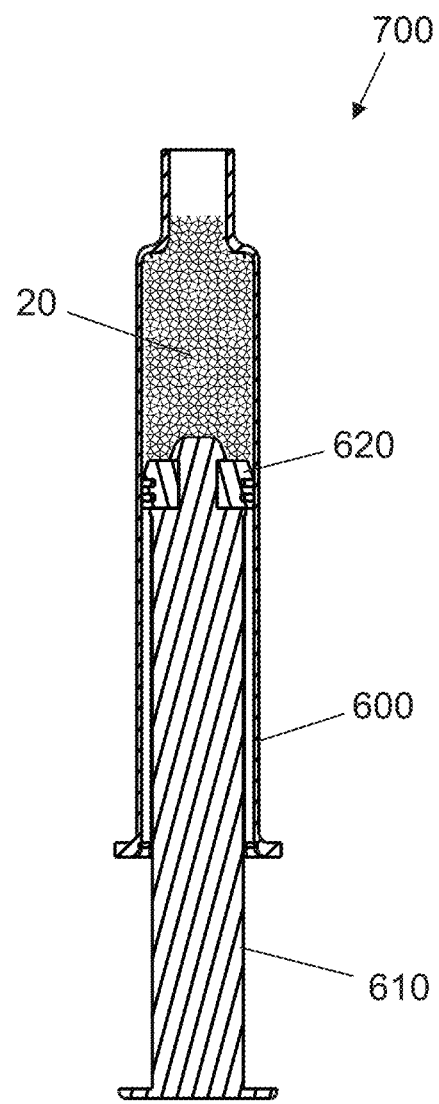
FIG. 76 is a sectional view of the objects of FIG. 75 at location A-A.
Figure 77:
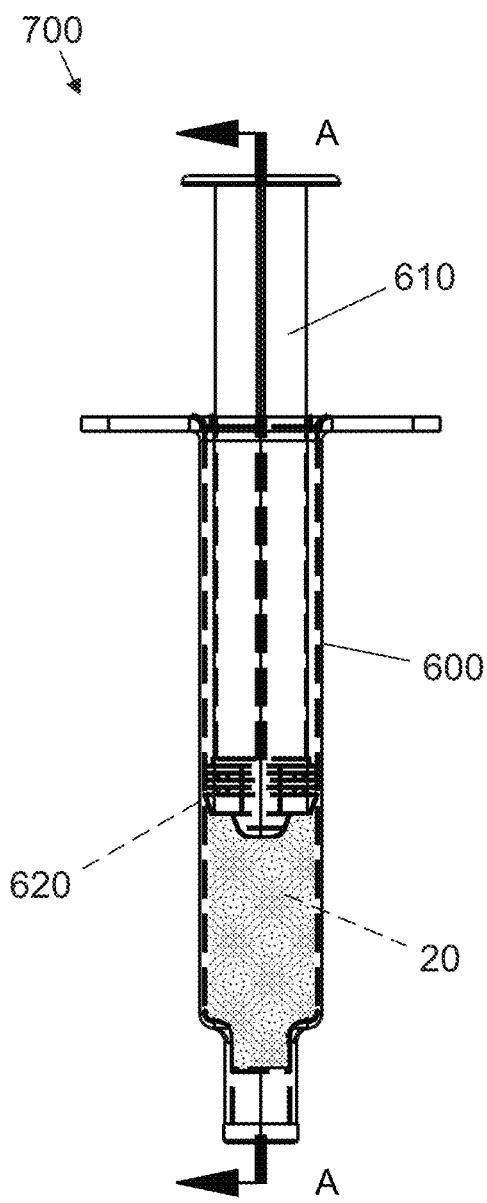
FIG. 77 depicts a syringe of the present invention wherein is formed lyophilized material using methods of the present invention.
Figure 78:
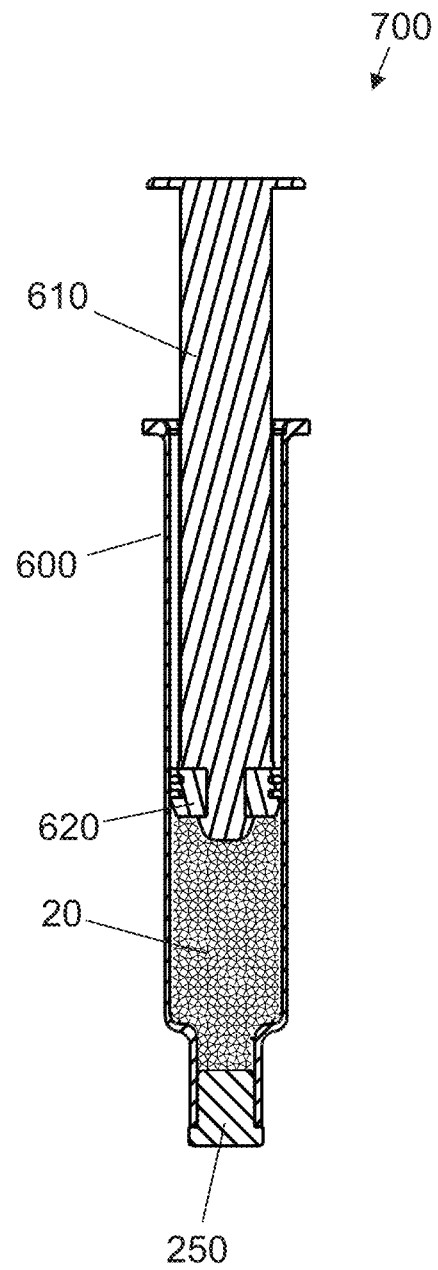
FIG. 78 is a sectional view of the objects of FIG. 77 at location A-A.

FIG. 61 depicts elements of a system for lyophilizing product in a syringe assembly wherein at completion the product is contained in a syringe with plunger, ready for solubilization and administering to a patient. A plurality of syringe barrels 600 are inserted into block 420. Thereafter, gasket 460 with openings 462 and plate 470 with openings 472 are affixed to block 420 by a suitable securing method, not shown. Hereafter details of the method will be described as previously done using block segment 400 and syringe body 600 positioned therein. Syringe barrel 600 is identical to syringe barrel 100 (FIGS. 1 through 7) in all aspects of form and function except as specifically subsequently specified, namely rim 110 is eliminated. FIGS. 62 through 64 depict a first step in a lyophilization method of the present embodiment wherein syringe barrel 600 containing product 10 for lyophilization is inserted into block 400. In a second step, gasket 460 and plate 470 are affixed to block 400 wherein aligned openings 462 and 472 are offset from the axis of barrel 600 as shown in FIG. 66. Block 400 with syringe barrel 600 positioned therein and plate 470 and gasket 460 affixed thereto is reoriented to a horizontal position as depicted in FIG. 67 in a third step of the method. Aligned openings 462 and 472 provide a path for venting during sublimation of product 10. In FIG. 68, sublimation is complete and liquid product 10 has become lyophilized product 20. Thereafter, in a fourth step of the method, block 400 with syringe barrel 600 containing product 20 and gasket 460 and plate 470 affixed thereto is reoriented to the vertical position as depicted in FIG. 69. Plate 470 and gasket 460 are then removed in a fifth step of the method after which block 400, syringe barrel 600 and product 20 are as shown in FIG. 70. Syringe plunger 630 with piston seal 640 is then assembled to syringe body 600 as depicted in FIGS. 71 and 72 in a sixth step of the method to create syringe assembly 700. Plunger 630 is inserted until seal 640 of plunger 630 effectively seals off the interior of syringe barrel 600 and product 20 contained therein from outside contamination. Syringe assembly 600 is then partially ejected from block 400 using ejector 500 in the manner previously herein described (FIGS. 73 and 74) after which sealed syringe assembly 600 is removed manually (seventh step). Thereafter syringe assembly 700 is reoriented as depicted in FIGS. 75 and 76 and stopper 250 is removed. Plunger 630 is advanced to remove excess air from syringe assembly 700, after which stopper 250 is reinserted. FIGS. 77 and 78 depict lyophilized product 20 in syringe assembly 700 ready for the addition of a diluent and administration to a patient. Because product 20 is lyophilized, special storage conditions are not required.

In embodiments previously described, the syringe barrel has four deformable walls that afford the barrel a substantially square cross-section. In the context of this square design, significant benefits are derived from conduction through the syringe walls which, in turn, is enabled by intimate contact between these deformable walls and the block into which it is inserted. This benefit may also be realized with conventional "round-barreled" syringes, or with another vessel formed from a resiliently deformable material, wherein a mid-portion of the vessel is slightly larger than the diameter of the well into which it is inserted. The intimate contact between this mid-portion and the well enables conduction of heat in the manner previously described and a related reduction in lyophilization time. A block of the present invention 1720 with a plurality of round wells 1704 is depicted in FIG. 149.

Figure 80:
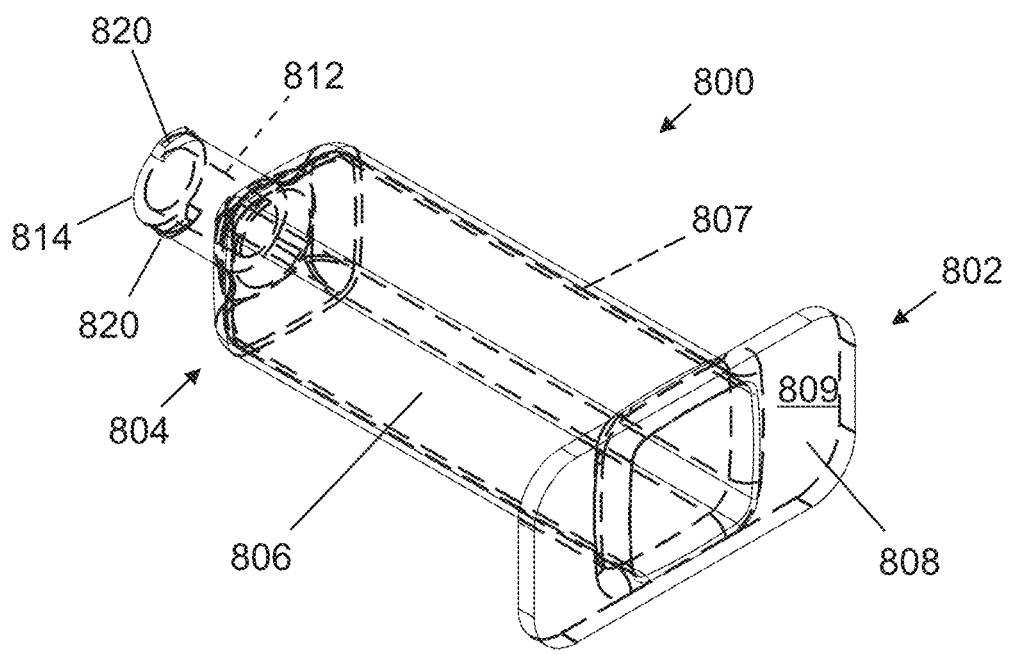
FIG. 80 is a proximal perspective view of the barrel of FIG. 79.
Figure 82:
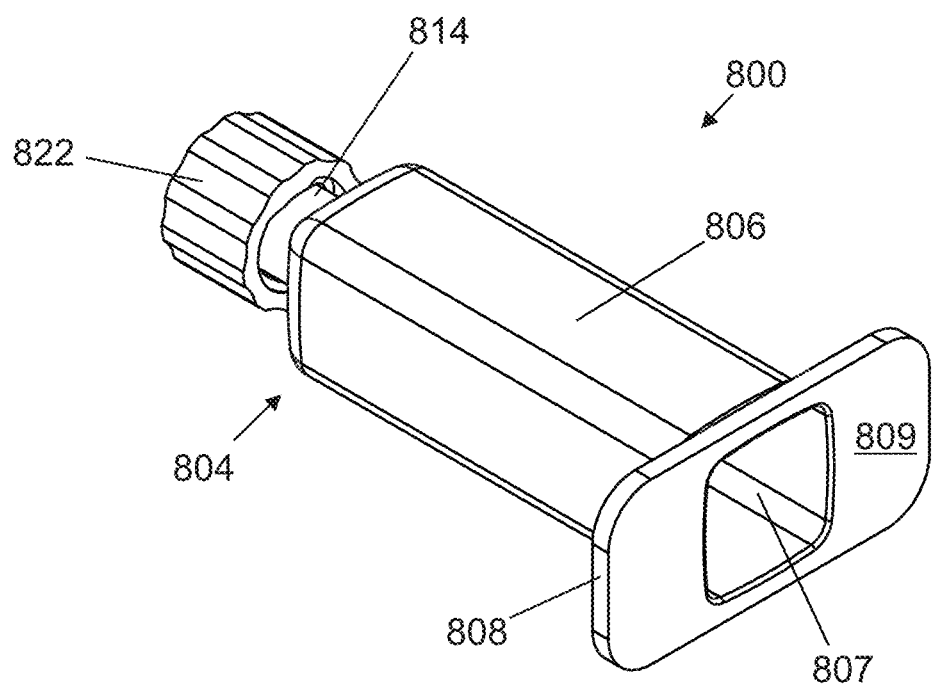
FIG. 82 is a proximal perspective view of the objects of FIG. 81.

A barrel 800 for a lyophilization syringe of the present invention is depicted in FIGS. 79 and 80. Barrel 800 is identical in form and function to barrel 100 (FIGS. 1 through 7) except as specifically described hereafter. Proximal rim 110 is eliminated. In some embodiments, walls 806 with inner surfaces 807 are convex as in barrel 100. Inner surfaces 807 surround and define an interior space (or cavity) 811. In others walls 806 are planar. Both fall within the scope of this invention. Distal flanges 820 are positioned at the distal end of outer surface 814 of output portion 812, flanges 820 being configured for mounting a Luer cap thereto. Barrel FIGS. 81 and 82 depict barrel 800 with Luer cap 822 mounted thereto in preparation for use. In some embodiments, walls syringe barrel 800 is formed of a resiliently deformable polymeric material. In other embodiments barrel 800 is formed of a rigid material such as, for instance, glass.

With respect to FIGS. 83 through 87, stopper 900 for lyophilization syringes of the present invention has a proximal end 902 with proximal surface 904 in which is form threaded socket 906. Stopper 900 has a distal end 910 with distalmost surface 911. Circumferential sealing ribs 916 and 918 are configured to match the contours formed by inner surfaces 807 of walls 806 of barrel 800, but expanded slightly so as to form a seal with the contours formed by surfaces 807. Distal ribs 916 are positioned on the distal half of stopper 900. Proximal ribs 918 are positioned on the proximal half of stopper 900. Channel 914 formed in surface 912 extends proximally from distal end 910 of stopper 900 to the distal side of the distal rib 918 of proximal ribs 918. Stopper 900 is preferably formed of a suitable resilient polymeric material. Syringes suitable for use in the context of the present invention require no special properties beyond those of materials commonly used for syringe seals, and the choice of a particular material is left to the designer. To wit, in certain embodiments, the present invention contemplates both the conventional "round-barreled" syringes of the prior art and the non-uniform and/or non-circular cross-sectioned syringes of the present invention, with or without resiliently deformable side walls.

Figure 88:
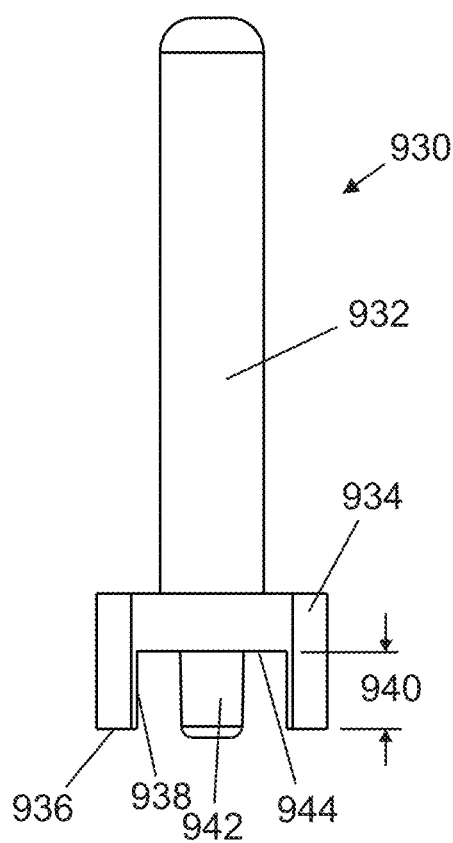
FIG. 88 is a side elevational view of an illustrative insertion tool suitable for mounting the stopper of FIG. 83 to the proximal end of the syringe barrel of FIG. 79.
Figure 89:
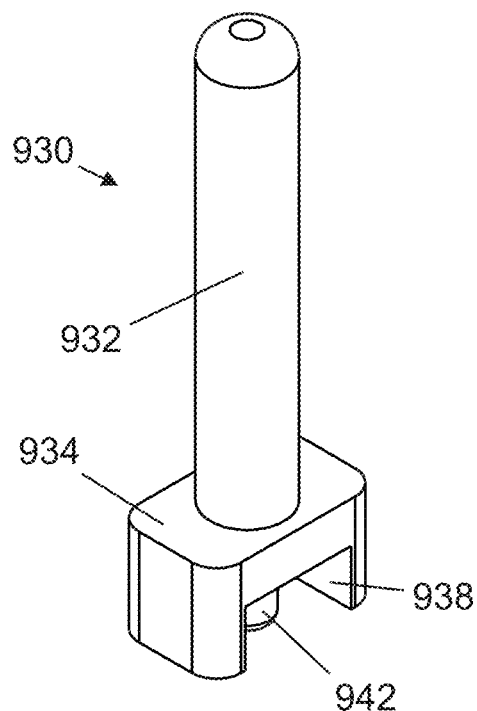
FIG. 89 is an upper perspective view of the insertion tool of FIG. 88.
Figure 90:
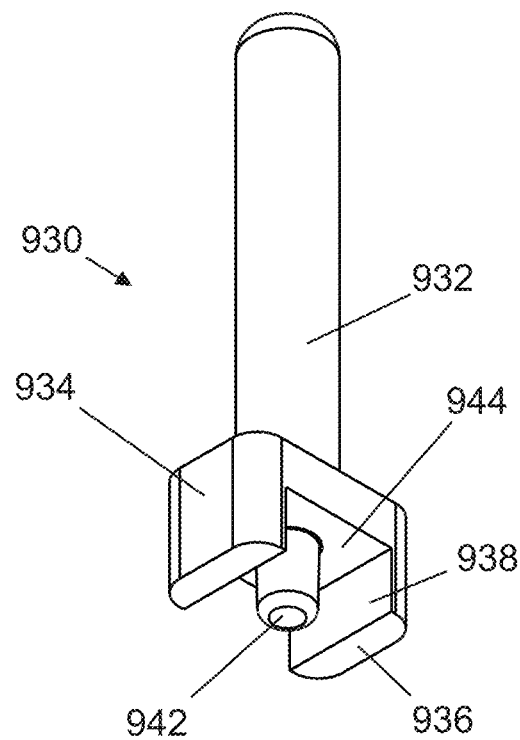
FIG. 90 is a lower perspective view of the insertion tool of FIG. 88.

Insertion tool 930, depicted in FIGS. 88 through 90, has an elongate proximal handle portion 932, and a distal portion 934 with a distal most surface 936. Channel 938 formed in distal portion 934 has a proximal surface 944 displaced distance 940 from distal surface 936. Cylindrical distal protrusion 942 has a diameter and length configured to allow protrusion 942 to be easily removably inserted into threaded socket 906 of stopper 900. Stopper 900 is retained on protrusion 942 during use of tool 930.

Stopper 900 is positioned on tool 930 as depicted in FIGS. 91 and 92, and retained there as shown in FIGS. 93 and 94. Channel 914 faces outward from channel 938 as shown in FIG. 93.

Insertion tool 930 is used to position stopper 900 in barrel 800 in a first axial position as depicted in FIGS. 95 through 97, distal surface of 944 of tool 930 contacting proximal surface 809 of proximal flange 808 of barrel 800. The proximal end of channel 914 extends proximally beyond the proximal end of barrel 800. Distal ribs 916 form a seal on inner surfaces 807 of barrel 800 that they contact.

After stopper 900 is properly positioned, tool 930 is removed, and barrel 800 and stopper 900 are as depicted in FIGS. 98 through 101, hereinafter referred to as the "venting" position. Venting (indicated by arrows 870) of the portion of interior space 811 of barrel 800 distal to stopper 900 is provided by channel 914, channel 914 providing a passage to the exterior of barrel 800. The portions of distal seals 916 in contact with surfaces 807 seal against those surfaces.

Figure 105:
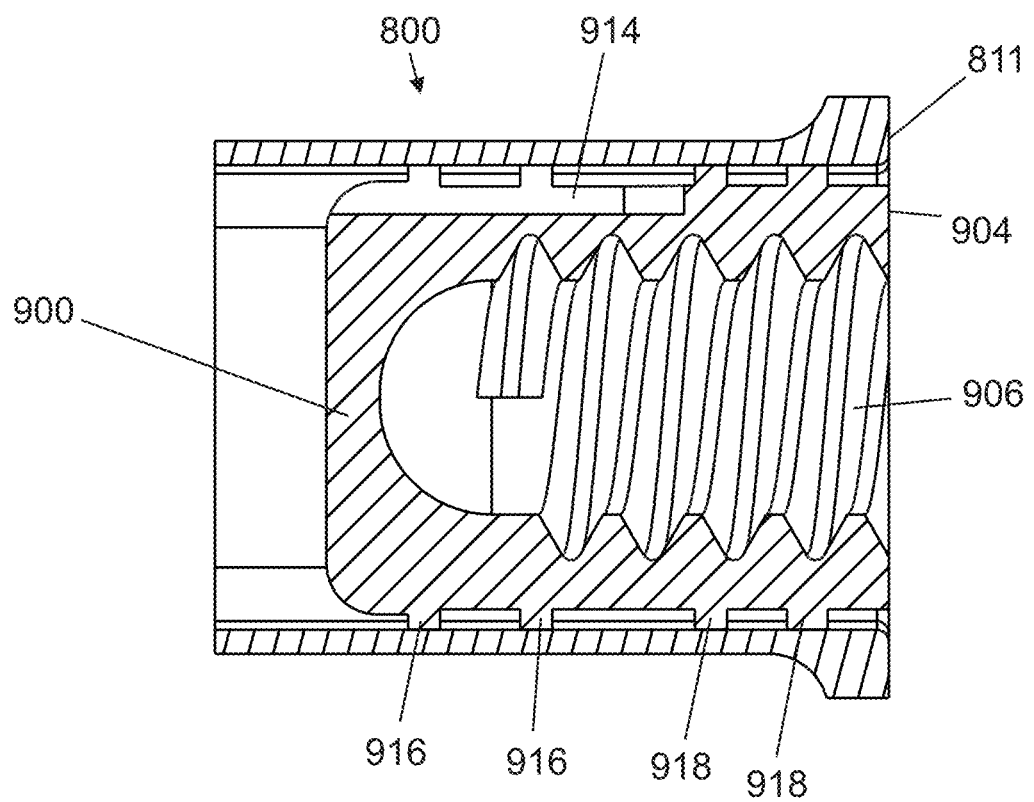
FIG. 105 is an expanded sectional view of the objects of FIG. 103 at location A-A.

FIGS. 102 through 105 depict barrel 800 and stopper 900 in their "sealed" position, seal 900 being advanced distally until proximal surface 904 of stopper 900 is coplanar with proximal surface 811 of flange 810 of barrel 800. As best seen in FIG. 105, proximal ribs 918 prevent flow through channel 914 thereby isolating interior space 811 from the exterior atmosphere.

In preferred embodiments syringes of the present invention, a plunger mechanism is fabricated from the assembly of stopper 900 to a demountable stem 950 as depicted in FIGS. 106 and 107. Stem 950 has an elongate portion 952 with a proximal flange 954 and a distal flange 956. Distal to distal flange 956, threaded portion 958 protrudes therefrom. Threads on portion 958 are configured to match those of threaded socket 906 of stopper 900 allowing seal 900 to be removably mounted to stem 952.

An exemplary syringe 1000 of the present invention is depicted in FIGS. 108 through 111, stem 950 and stopper 900 forming the plunger. As depicted, interior space 811 is sealed. Hereafter, the syringe functions in the same manner as prior art syringes.

When using lyophilization devices and methods of the present invention, lyophilization occurs in the syringe that is shipped to the user. The lyophilized material remains in the syringe and is not exposed to the outside atmosphere after lyophilization. The user re-hydrates the lyophilized material in that same syringe. Unique features of lyophilization devices and methods of the present invention significantly decrease the time required for lyophilization.

The lyophilization methods of the present invention include placing material 880 to be lyophilized in barrel 800 with Luer cap 822 mounted as depicted in FIGS. 112 and 113. Using insertion tool 830, stopper 900 is positioned as shown in FIGS. 114 and 115 and FIGS. 95 through 97 in the "venting" position as shown in FIGS. 98 through 101. Thereafter barrel 800 with stopper 900 in the venting configuration is reoriented to axis horizontal with slot 914 directed upward as depicted in FIG. 116. Thereafter the assembly is placed in a lyophilization machine and the processing cycle performed. Water in material 880 is removed by sublimation resulting in lyophilized material 882 as depicted in FIG. 117. The volume of material 882 being significantly less than material 880. Barrel 800 and stopper 900 are then reoriented to an axis vertical position as shown in FIG. 118, and stopper 900 is advanced distally to its "sealed" position as shown in FIG. 119 without material 882 being exposed to surrounding atmosphere. The sealed assembly is ready for packaging and shipment. Stem 950 is attached to stopper 900 by the user as shown in FIGS. 120 and 121, and FIGS. 108 through 111 to create syringe assembly 1000. Stem 950 and stopper 900 are mounted thereto forming the plunger of syringe 1000.

During lyophilization, water is removed from material 880 by sublimation, a process that occurs only at the free surface of material 880. One factor determining the rate of sublimation is the area of the free surface. Lyophilization devices and methods of the present invention significantly shorten the process time by dramatically increasing the free surface available for sublimation. This is shown graphically in FIGS. 124 through 126. FIG. 124 depicts barrel 800, Luer cap 822 and stopper 900 in their venting configuration. FIG. 126 depicts the free surface area 881 of material 888 with the assembly in the axis vertical orientation as in FIG. 115. FIG. 125 depicts the free surface area 881 of material 888 in the axis horizontal orientation as shown in FIG. 116. The free surface area 881 in the axis horizontal orientation (FIG. 125) is approximately three times the free surface area 881 in the axis vertical oriental orientation (FIG. 126). This increased free surface allows sublimation to occur at a much faster rate resulting in decreased lyophilization time.

In embodiments previously disclosed herein in which a sealing stopper is present during lyophilization, the venting channel in the stopper is formed in a "flat" lateral surface of the stopper. This establishes alignment between the syringe barrel and the venting channel so as to ensure that when the barrel with the stopper is brought to the horizontal orientation, the venting channel is oriented upwards to prevent loss of product. It is essential that any syringe or vial used for lyophilization in an axis horizontal orientation have an alignment feature to ensure the venting channel is oriented toward the top surface (i.e., above the liquid fill line).

In an alternate embodiment, a conventional cylindrical or "round barreled" syringe body 1100 may be used with a stopper of the present invention as a lyophilization container, whereby the processing occurs with the barrel axis horizontally oriented. Referring to FIGS. 127 and 128, barrel 1100 has mounted thereto Luer cap 1122, and a proximal flange 1108 with proximal-most surface 1109.

Stopper 1200 (FIGS. 129 through 133) has a distal end 1210 with distal-most surface 1211, and a proximal end 1202. Proximal flange 1203 with distal-most surface 1204 has an alignment surface 1226 parallel to the bottom surface of venting channel 1214 and oriented 180 degrees therefrom on stopper 1200. Venting channel 1214 extends proximally from proximal-most surface 1211, through distal ribs 1216, and ending a short distance distal to the distal-most rib of proximal ribs 1218.

FIGS. 134 and 135 depict lyophilization assembly 1290 consisting of barrel 1100 with stopper 1200 positioned therein in the venting position as previously described. Assembly 1290 is oriented and positioned using mounting fixture 1300 depicted in FIGS. 136 through 138. Fixture 1300 had a horizontal base portion 1302 with top surface 1304, and a vertical portion 1306 with semicircular cradle portion 1308 formed therein, cradle portion 1308 having a radius 1310. Radius 1310 is slightly larger than half the diameter of barrel 1100 so that barrel 1100 may be positioned loosely therein.

The height of cradle portion 1308 above top surface 1304 is chosen such that when lyophilization assembly 1290 is positioned on fixture 1300 as shown in FIGS. 139 through 141, the axis of vessel 1290 is horizontal, alignment surface 1226 of stopper 1200 resting on top surface 1304 of base portion 1302 of fixture 1300. Channel 1214 in stopper 1200 is oriented upward. Lyophilization using assembly 1290 with mounting fixture 1300 is accomplished in the same manner as previously herein described. With barrel 1100 oriented vertically, material to be lyophilized is loaded into assembly 1290. Thereafter stopper 1200 is inserted axially into barrel 1100 to the venting position creating assembly 1290. Assembly 1290 is placed in fixture 1300, the free surface 1190 of liquid within assembly 1290 as shown in FIG. 139. Lyophilization is accomplished in the conventional manner using a suitable machine. When the process is complete, assembly 1290 is removed from fixture 1300, rotated to an axis vertical position, and stopper 1200 fully inserted until proximal flange 1203 contacts distal-most surface 1109 of flange 1108 of barrel 1100 as depicted in FIG. 142. Free surface 1192 of the lyophilized material (a powder) indicates the substantial volume reduction achieved by lyophilization. Assembly 1290 is now sealed and ready for storage or shipping. Prior to solubilization, stopper 1200 is removed and a suitable plunger stem (not shown) is inserted into barrel 1200 to create a syringe that is configured and used thereafter in the same manner as prior art syringes. When stopper 1200 is removed for replacement by the plunger, contents of assembly 1290 are exposed to external atmosphere. Due to the presence of proximal flange 1203, stopper 1200 cannot be used as a seal for a plunger as in previous embodiments.

It may be desirable to increase the distance between the free surface of the material being lyophilized and the venting channel (914 in FIGS. 83 through 87, 1214 in FIGS. 129 to 133) distal end so as to prevent clogging of the channel or loss of material. This may be accomplished by inclining the lyophilization assembly using an alternate mounting fixture 1400 of the present invention. Referring now to FIGS. 143 and 144, alternate fixture 1400 has a surface 1404 inclined angle 1402 to horizontal, and a distal portion 1412 wherein is formed locating cradle 1414. Positioning lyophilization assembly 1290 in alternate fixture 1400 as shown in FIGS. 142 and 143 increases the distance between the venting channel and free surface 1190. The size of free surface 1190 is diminished due to inclination of assembly 1290, however it is still much greater than the free surface present when assembly 1290 is vertically oriented during lyophilization. In a preferred embodiment angle 1402 is less than five degrees. In other embodiments angle 1402 is between five and fifteen degrees. In still other embodiments angle 1402 is between 15 and 45 degrees.

In assembly 1290, positioning channel 1214 vertically upward is accomplished using reference surface 1226 of stopper 1204, cylindrical barrel 1100 providing no features for rotational alignment. In other embodiments, the barrel cross-section provides an internal reference surface that aligns the stopper with the barrel, and an external reference surface that aligns the barrel with a fixture or other external locating feature. A benefit of this design is that the stopper can also function as the stopple on a plunger eliminating the need to expose the lyophilized contents to external atmosphere.

Referring now to FIGS. 145 and 146, syringe barrel 1500 is neither rounded nor squared but rather a non-uniform "D" shape, the cross-section of which is defined by a cylindrical portion 1550 and a planar portion 1552. Stopper 1600 has a complementary shape configured to seal on the internal surfaces of barrel 1500 with cylindrical portion 1660 and planar portion 1662, and a threaded socket 1606 formed in its proximal end. Channel 1614 is positioned on the top of cylindrical portion 1660 opposite to planar portion 1662. Syringe barrel 1500 and stopper 1600 are used in the same manner as barrel 800 (FIGS. 79 and 80) and stopper 900 (FIGS. 83 through 87), forming a lyophilization syringe that can be sealed after processing, shipped to a user, and solubilized in preparation for use, the process occurring without the lyophilized product being exposed to external atmosphere.

INDUSTRIAL APPLICABILITY

As discussed above, lyophilization is ubiquitous in the chemical, pharmaceutical, and food industries. However, there is an ongoing need in the art to improve the efficiency and economy of the lyophilization process. The instant invention addresses this continuing need by providing a readily scalable lyophilization syringes, assemblies, apparatus, and methods that impart a shorter lyophilization cycle timeline and affords uniformity in all units of a lyophilization batch.

While the invention is herein described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention. For example, this disclosure includes and contemplates combinations with features and elements known to the average artisan in the art. Thus, the novel embodiments, features, and elements that have been disclosed may also be combined with any conventional features or elements to form a distinct invention as defined by the claims. Likewise, any feature or element of any embodiment may also be combined with features or elements from other inventions to form another distinct invention as defined by the claims. Therefore, it will be understood that any of the features shown and/or discussed in the present disclosure may be implemented singularly or in any suitable combination.

Other advantages and features will become apparent from the claims filed hereafter, with the scope of such claims to be determined by their reasonable equivalents, as would be understood by those skilled in the art. Thus, the invention is intended to be defined not by the above description, but by the following claims and their equivalents.

All publications, patent applications, patents and other references mentioned herein are incorporated by reference in their entirety. However, nothing herein should be construed as an admission that the invention is not entitled to antedate such disclosure by virtue of prior invention.

What is claimed:

1. A lyophilization syringe configured for both in situ lyophilization of an initial liquid preparation into a lyophilized product and subsequent reconstitution and dispensing of the lyophilized product in rehydrated form, said syringe comprising an elongate central barrel characterized by:
   a. a plurality of distinct lateral walls joined together to define an exterior surface, an interior surface, and a hollow interior bore configured to retain both an initial product and a product in lyophilized forms,
   b. an open distal tip configured to engage a hypodermic needle assembly; and
   c. an open proximal end configured to removably receive a stopper; wherein said central barrel has a non-uniform or non-circular cross-section.

2. The lyophilization syringe of claim 1, wherein central barrel has a substantially square cross-section.

3. The lyophilization syringe of claim 1, wherein central barrel has an irregular curvilinear cross-section.

4. The lyophilization syringe of claim 3, wherein said irregular curvilinear cross-section is D-shaped.

5. The lyophilization syringe of claim 1, wherein said plurality of distinct lateral walls are resiliently deformable.

6. The lyophilization syringe of claim 5, wherein said central barrel comprises four of said deformable lateral walls, each of which bows outward to define a convex exterior surface.

7. A lyophilization syringe assembly comprising the:
   a. a lyophilization syringe comprising an elongate central barrel characterized by an exterior surface, an interior surface, and a hollow interior bore configured to retain both an initial product in liquid and lyophilized forms, an open distal tip configured to engage a hypodermic needle assembly; and an open proximal end configured to removably receive a stopper; and
   b. stopper removably mounted to the open proximal end of the elongate central barrel of said syringe, wherein said stopper includes (i) at least one vent channel disposed along a lateral surface, and (ii) at least one circumferential sealing rib proximal to a distal end of said stopper at least one vent channel that engages said interior surface to form a gas and fluid tight seal that guards against contamination and leakage of syringe barrel contents.

8. The lyophilization syringe assembly of claim 7, wherein said stopper further includes (iii) a threaded socket formed in a proximal surface of the stopper.

9. The lyophilization syringe assembly of claim 7, wherein said central barrel has a non-uniform or non-circular cross-section.

10. The lyophilization syringe assembly of claim 7, wherein the open proximal end of said central barrel is further characterized by a wide radial flange and the open distal tip is sealed by a distal cap.

11. The lyophilization syringe assembly of claim 9, wherein said open distal tip comprises a Luer taper and said distal cap comprises a Luer cap.

12. The lyophilization syringe assembly of claim 7, wherein when said stopper is partially inserted into said open proximal end, said vent channel forms a passage for gaseous outflow from the central barrel, thereby providing an escape path for outgassing during said in situ lyophilization, further wherein said vent channel is closed when said stopper is distally inserted into said open proximal end, such that said lyophilized product is sealed within said central barrel.

13. A method of using a single syringe to both lyophilize a liquid preparation into a lyophilized product and subsequently rehydrate and dispense the lyophilized product in rehydrated form, said method comprising the steps of:

a. introducing said liquid preparation into a hollow interior bore of a lyophilization syringe comprising an elongate central barrel characterized by an exterior surface, an interior surface, and a hollow interior bore configured to retain said liquid preparation and said lyophilized product, an open distal tip configured to engage a hypodermic needle assembly; and an open proximal end configured to removably receive a stopper; and
   b. affixing a distal cap to said open distal tip;
   c. partially inserting a stopper into the open proximal end of said elongate central barrel to a first axial position so as to form a passage whereby gas may flow out from the central barrel and through a member, wherein said stopper comprises (i) at least one vent channel disposed along a lateral surface that serves as said passage whereby gas may flow out from the central barrel and through said member, (ii) at least one sealing rib circumferentially disposed about said lateral surface at a position that is proximal to a distal end of said at least one vent channel; and (iii) optionally a threaded socket formed in a proximal surface of the stopper;
   d. lyophilizing said liquid preparation into said lyophilized product in situ;
   e. axially sliding the stopper along the barrel in a distal direction to a second axial position wherein said at least one vent channel is closed and said lyophilized product is sealed within said central barrel.

14. The method of claim 13, further comprising the step of attaching a demountable stem to the threaded socket of said stopper whereby said stopper forms the piston element of a plunger mechanism.

15. The method of claim 14, further comprising the step of manipulating the plunger mechanism to draw liquid into the central barrel via the open distal tip so as to rehydrate the lyophilized product.

16. The method of claim 15, further comprising the step of manipulating the plunger to dispense the rehydrated contents from said central barrel.

17. The method of claim 13, wherein in step c, the central barrel is vertically oriented with the distal cap pointing down.

18. The method of claim 17, wherein between steps c and d, the central barrel is rotated to a horizontal orientation.

19. The method of step 13, wherein in said step d, heat is applied to said lyophilization syringe until all water is removed from the liquid preparation being lyophilized.

20. The method of step 19, wherein heat is applied to said lyophilization syringe by means of a block made from a heat conductive material, said block having a plurality of wells arranged on a top side configured to receive said lyophilization syringe.

* * * * *